(12) United States Patent
Giasolli et al.

(10) Patent No.: US 11,123,527 B2
(45) Date of Patent: *Sep. 21, 2021

(54) WEDGE DISSECTORS FOR A MEDICAL BALLOON

(71) Applicant: CAGENT VASCULAR, INC., Wayne, PA (US)

(72) Inventors: Robert M. Giasolli, Orange, CA (US); Peter Schneider, Honolulu, HI (US); Peter Johansson, Wayne, PA (US)

(73) Assignee: Cagent Vascular, Inc., Wayne, PA (US)

( * ) Notice: Subject to any disclaimer, the term of this patent is extended or adjusted under 35 U.S.C. 154(b) by 8 days.

This patent is subject to a terminal disclaimer.

(21) Appl. No.: 16/234,422

(22) Filed: Dec. 27, 2018

(65) Prior Publication Data

US 2019/0240464 A1  Aug. 8, 2019

Related U.S. Application Data

(63) Continuation of application No. 15/268,407, filed on Sep. 16, 2016, now Pat. No. 10,166,374.
(Continued)

(51) Int. Cl.
*A61M 25/10* (2013.01)
*B65D 19/42* (2006.01)
(Continued)

(52) U.S. Cl.
CPC ...... *A61M 25/104* (2013.01); *A61M 25/1027* (2013.01); *B65D 19/42* (2013.01); *B65D 19/44* (2013.01); *B65D 85/48* (2013.01); *B65G 1/02* (2013.01); *A61B 2017/22001* (2013.01); *A61M 2025/105* (2013.01); *A61M 2025/109* (2013.01); *A61M 2025/1031* (2013.01); *A61M 2025/1086* (2013.01); *B65D 2519/00024* (2013.01);
(Continued)

(58) Field of Classification Search
CPC .......... A61M 25/104; A61M 2025/107; A61M 2025/1086; A61M 2025/1031; A61B 2017/22001
See application file for complete search history.

(56) References Cited

U.S. PATENT DOCUMENTS 4,665,906 A   5/1987  Jervis
4,699,611 A  10/1987  Bowden
(Continued)

FOREIGN PATENT DOCUMENTS

AU   2009226025   9/2009
AU   2015343272   7/2020
(Continued)

OTHER PUBLICATIONS

U.S. Appl. No. 15/316,067, dated Dec. 2, 2016, Giasolli et al.

*Primary Examiner* — Anh T Dang
(74) *Attorney, Agent, or Firm* — Knobbe, Martens, Olson & Bear, LLP

(57) ABSTRACT

A cage can be positioned around a medical balloon, such as an angioplasty balloon, to assist in a medical procedure. The cage can include a plurality of strips, each extending between a set of rings including first and second rings. As the balloon expands, the first and second rings move closer together and allow the strips to expand outward. The cage may have wedge dissectors on the strips.

16 Claims, 60 Drawing Sheets

Related U.S. Application Data

(60) Provisional application No. 62/220,195, filed on Sep. 17, 2015.

(51) Int. Cl.
  *B65D 19/44* (2006.01)
  *B65D 85/48* (2006.01)
  *B65G 1/02* (2006.01)
  *A61B 17/22* (2006.01)

(52) U.S. Cl.
  CPC .............. *B65D 2519/00059* (2013.01); *B65D 2519/0081* (2013.01); *B65D 2519/00094* (2013.01); *B65D 2519/00273* (2013.01); *B65D 2519/00293* (2013.01); *B65D 2519/00323* (2013.01); *B65D 2519/00333* (2013.01); *B65D 2519/00373* (2013.01); *B65D 2519/00562* (2013.01); *B65D 2519/00572* (2013.01); *B65D 2519/00741* (2013.01); *B65D 2519/00781* (2013.01); *B65D 2519/00796* (2013.01); *B65D 2519/00805* (2013.01); *B65D 2519/00815* (2013.01)

(56) References Cited

U.S. PATENT DOCUMENTS

| | | | |
|---|---|---|---|
| 4,795,458 A | 1/1989 | Regan | |
| 4,856,516 A | 8/1989 | Hillstead | |
| 5,078,736 A | 1/1992 | Behl | |
| 5,397,355 A | 3/1995 | Marin et al. | |
| 5,484,411 A | 1/1996 | Inderbitzen et al. | |
| 5,514,154 A | 5/1996 | Lau et al. | |
| 5,591,197 A | 1/1997 | Orth et al. | |
| 5,593,434 A | 1/1997 | Williams | |
| 5,718,684 A | 2/1998 | Gupta | |
| 5,824,053 A | 10/1998 | Khosravi et al. | |
| 6,254,642 B1 | 7/2001 | Taylor | |
| 6,485,496 B1 | 10/2002 | Suyker et al. | |
| 7,204,847 B1 | 4/2007 | Gambale | |
| 7,291,158 B2 | 11/2007 | Crow | |
| 7,691,116 B2 | 4/2010 | Goodin | |
| 9,204,893 B2 | 12/2015 | Rizk et al. | |
| 10,166,374 B2 | 1/2019 | Giasolli et al. | |
| 10,172,729 B2 | 1/2019 | Fulkerson et al. | |
| 10,258,487 B2 | 4/2019 | Fulkerson et al. | |
| 10,463,842 B2 | 11/2019 | Giasolli et al. | |
| 10,471,238 B2 | 11/2019 | Schneider et al. | |
| 10,689,154 B2 | 6/2020 | Giasolli et al. | |
| 2001/0020151 A1 | 9/2001 | Reed et al. | |
| 2002/0010489 A1* | 1/2002 | Grayzel ............... | A61F 2/958 606/194 |
| 2005/0137618 A1* | 6/2005 | Kunis .................. | A61B 17/22 606/192 |
| 2005/0177130 A1 | 8/2005 | Konstantino et al. | |
| 2005/0228343 A1 | 10/2005 | Kelley | |
| 2006/0015134 A1* | 1/2006 | Trinidad ......... | A61B 17/320725 606/194 |
| 2006/0085023 A1 | 4/2006 | Davies et al. | |
| 2006/0129093 A1 | 6/2006 | Jackson | |
| 2006/0149308 A1 | 7/2006 | Melsheimer | |
| 2006/0184191 A1 | 8/2006 | O'Brien | |
| 2006/0271093 A1 | 11/2006 | Holman | |
| 2007/0016232 A1* | 1/2007 | St. Martin ............. | A61L 29/14 606/159 |
| 2008/0275483 A1 | 11/2008 | Makower et al. | |
| 2009/0240270 A1 | 9/2009 | Schneider et al. | |
| 2011/0178503 A1 | 7/2011 | Kangas | |
| 2012/0172901 A1* | 7/2012 | Manderfeld ...... | A61M 25/1027 606/159 |
| 2013/0018396 A1* | 1/2013 | Gunderson .... | A61B 17/320725 606/159 |
| 2013/0110142 A1 | 5/2013 | Bence et al. | |
| 2013/0165958 A1 | 6/2013 | Schneider et al. | |
| 2013/0190725 A1 | 7/2013 | Pacetti et al. | |
| 2016/0346506 A1 | 12/2016 | Jackson et al. | |
| 2017/0080192 A1 | 3/2017 | Giasolli et al. | |
| 2017/0100570 A1 | 4/2017 | Giasolli et al. | |
| 2017/0106174 A1 | 4/2017 | Schneider et al. | |
| 2017/0333686 A1 | 11/2017 | Schneider et al. | |
| 2018/0200491 A1 | 7/2018 | Giasolli et al. | |
| 2018/0304052 A1 | 10/2018 | Schneider et al. | |
| 2020/0140141 A1 | 5/2020 | Giasolli et al. | |
| 2020/0147355 A1 | 5/2020 | Schneider et al. | |
| 2020/0155815 A1 | 5/2020 | Giasolli et al. | |
| 2020/0188641 A1 | 6/2020 | Giasolli et al. | |

FOREIGN PATENT DOCUMENTS

| | | |
|---|---|---|
| CN | 1642593 A | 7/2005 |
| CN | 101420913 | 3/2012 |
| CN | 102512747 | 6/2012 |
| CN | 102781508 A | 11/2012 |
| CN | 102939125 A | 2/2013 |
| CN | 203379465 | 1/2014 |
| CN | 103582508 | 2/2014 |
| CN | 103764218 | 4/2014 |
| CN | 203564643 | 4/2014 |
| CN | 103948972 | 6/2016 |
| CN | 103930158 | 8/2016 |
| CN | 107405158 A | 11/2017 |
| CN | 107405475 A | 11/2017 |
| CN | 108348734 A | 7/2018 |
| CN | 110114108 A | 8/2019 |
| CN | ZL 201080051844.9 | 7/2020 |
| CN | ZL 201580071624.5 | 9/2020 |
| EP | 2254641 | 9/2016 |
| EP | 3215030 | 9/2017 |
| EP | 3215212 | 9/2017 |
| EP | 3349837 | 7/2018 |
| EP | 3541464 | 9/2019 |
| WO | WO 2002/043796 | 6/2002 |
| WO | WO 2003/051442 | 6/2003 |
| WO | WO 2003/068307 | 8/2003 |
| WO | WO 2005/076833 | 8/2005 |
| WO | WO 2009/117158 | 9/2009 |
| WO | WO 2011/035132 | 3/2011 |
| WO | WO 2013/012714 | 1/2013 |
| WO | WO 2016/116821 | 7/2016 |
| WO | WO 2018/094077 | 5/2018 |
| WO | WO 2020/023749 | 1/2020 |

* cited by examiner

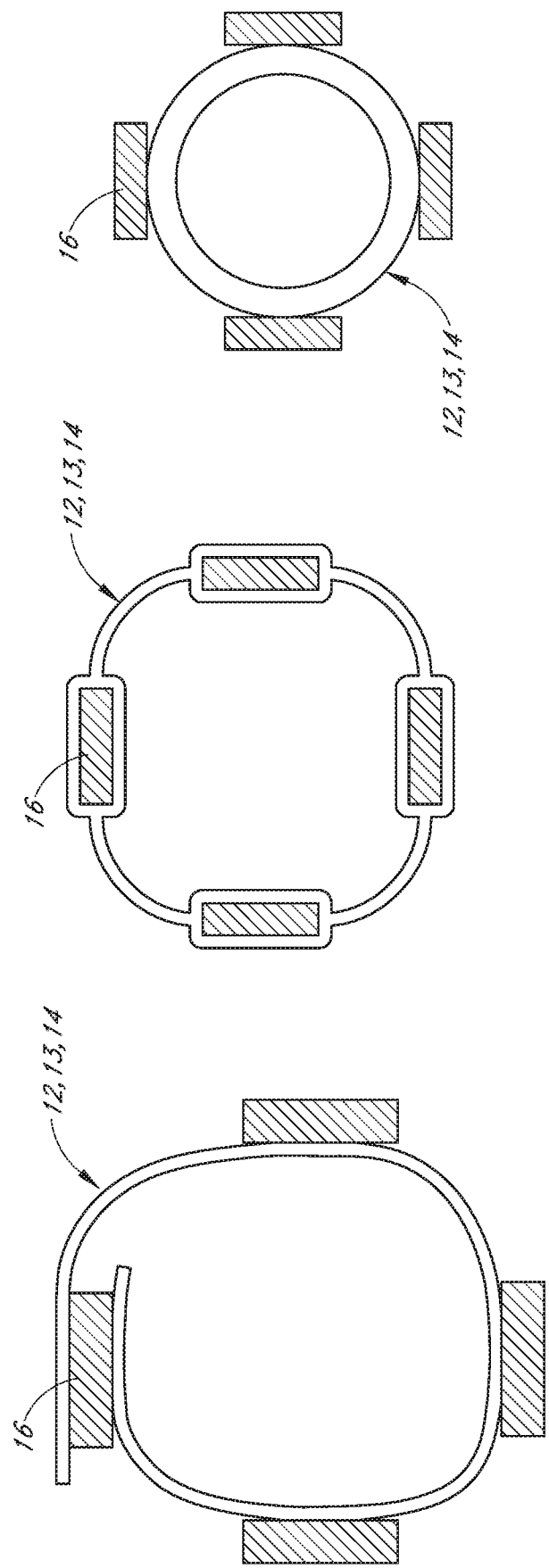

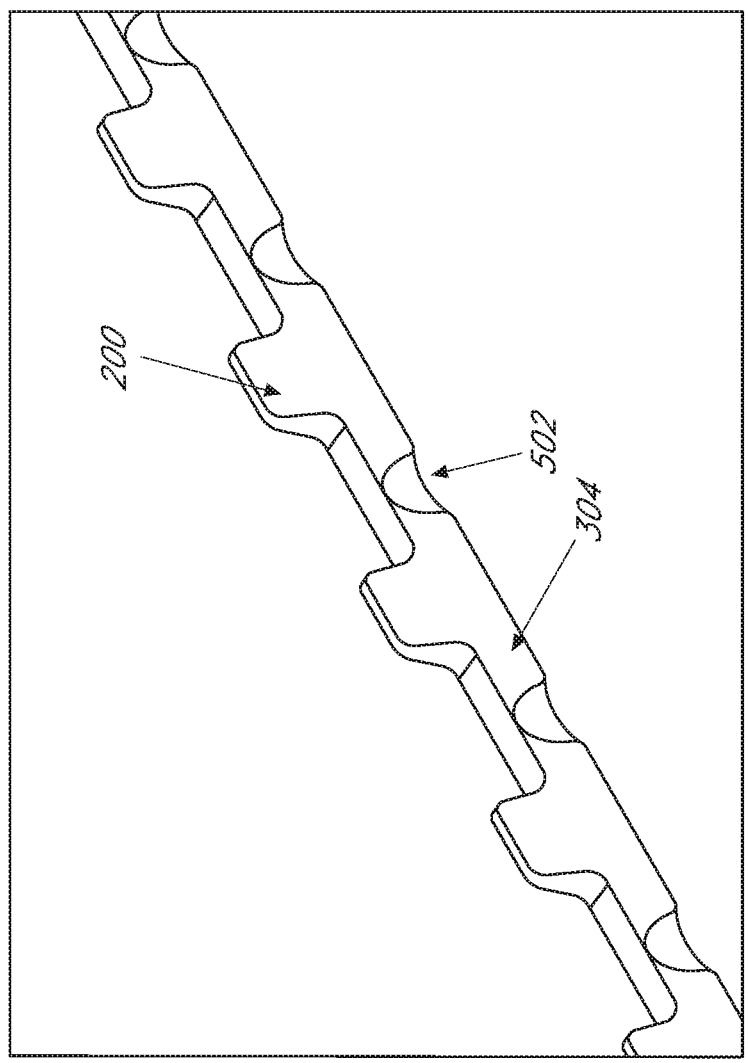

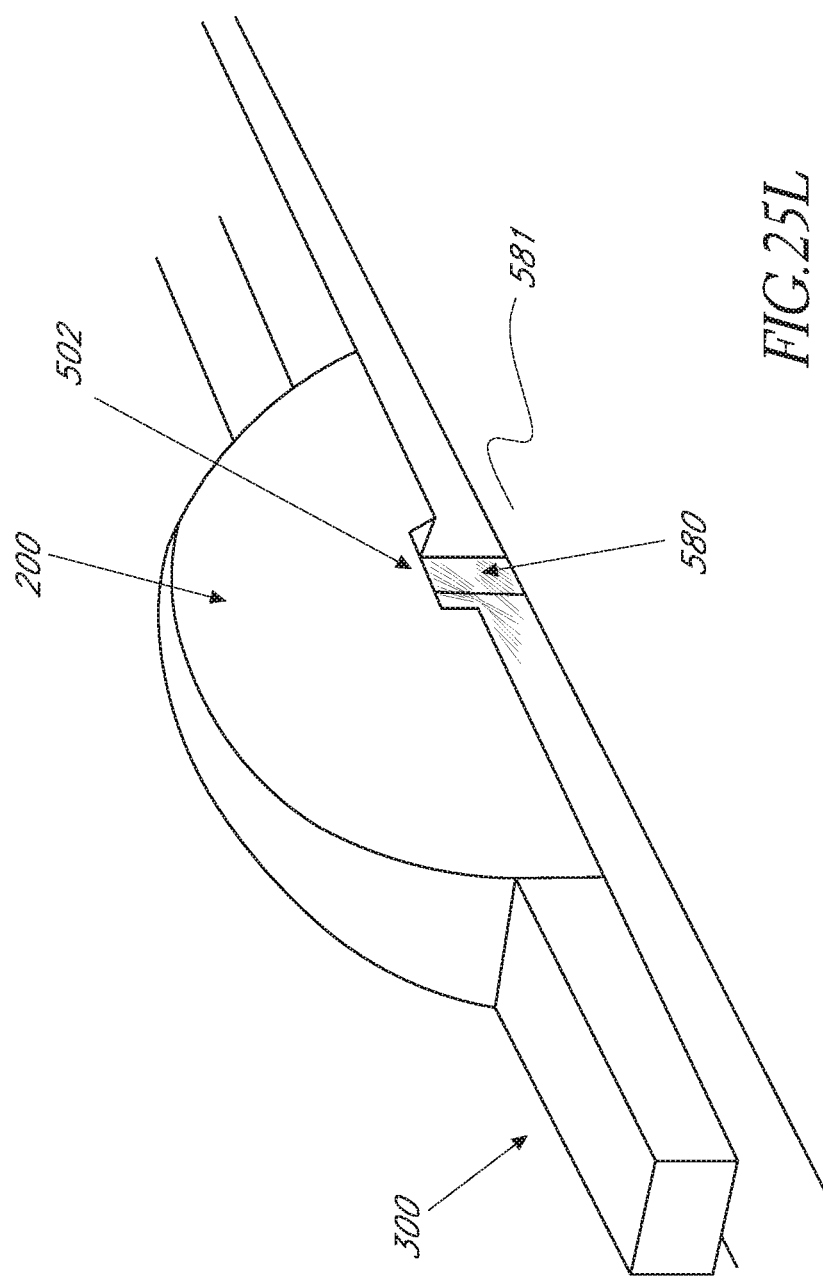

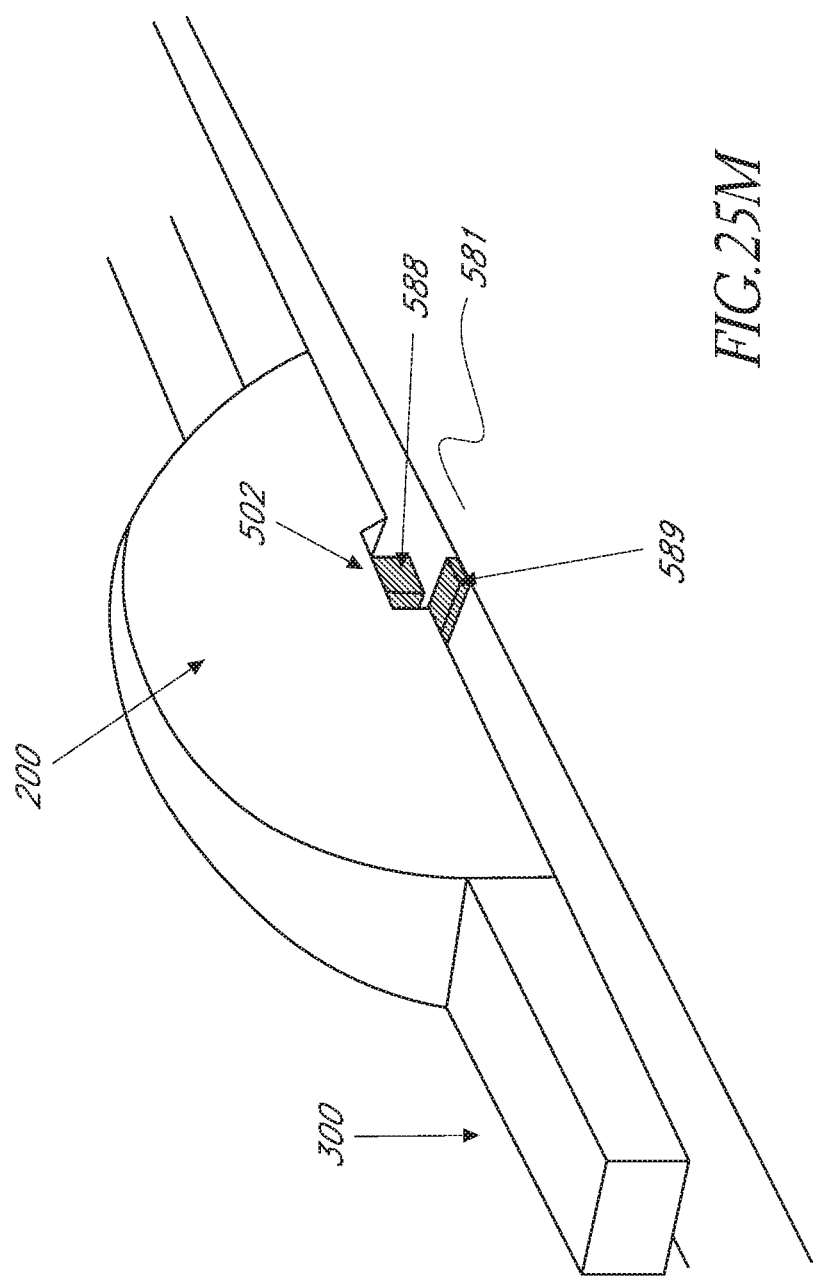

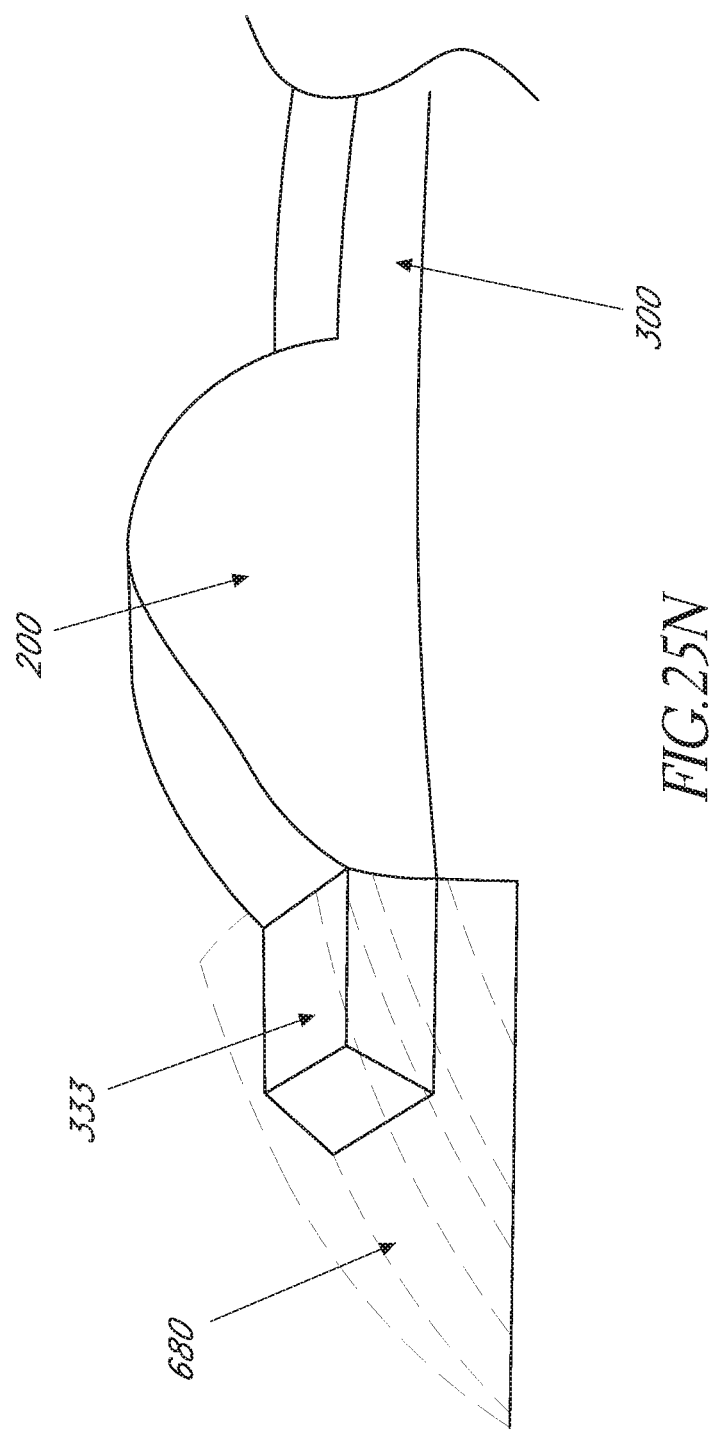

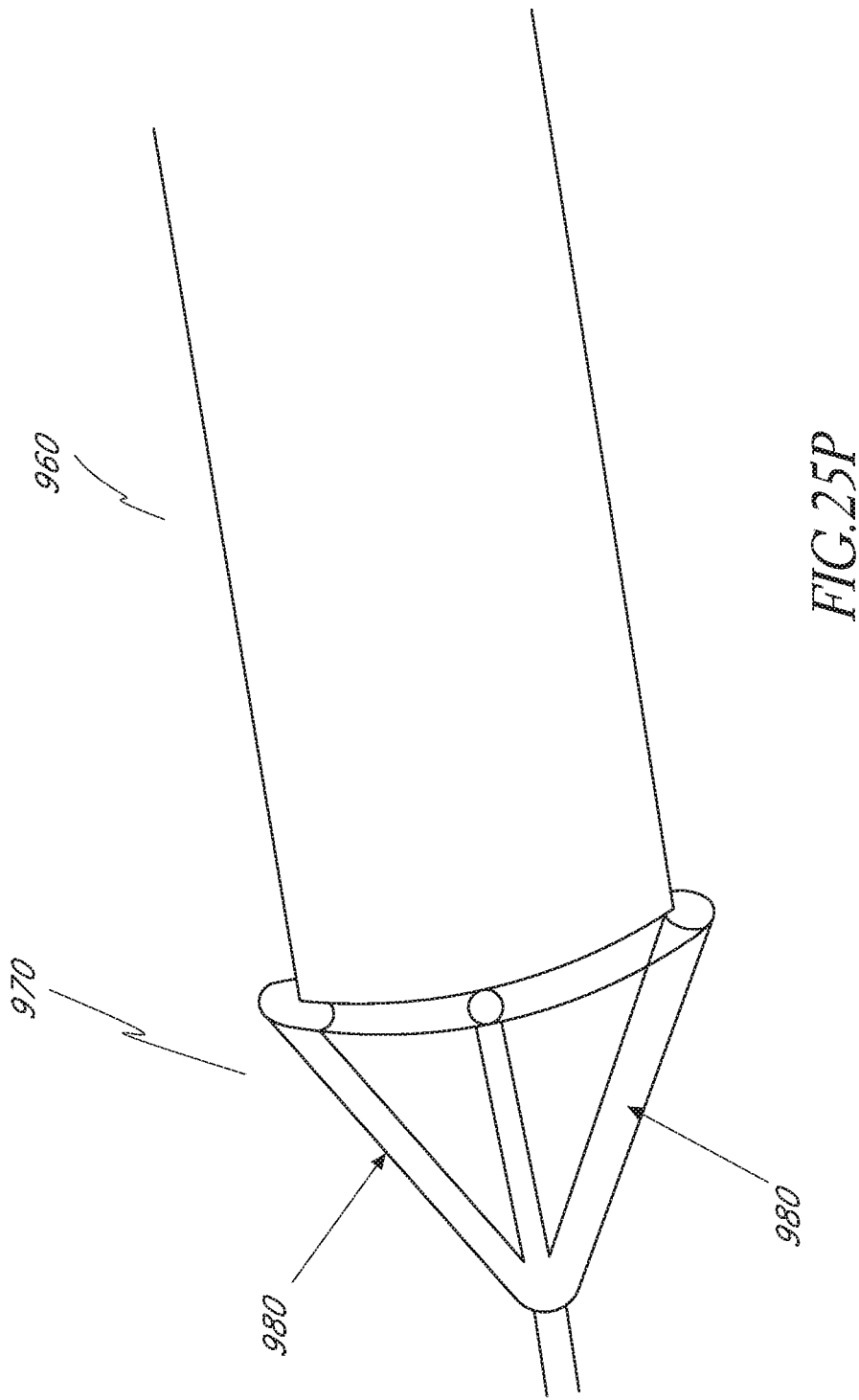

WEDGE DISSECTORS FOR A MEDICAL BALLOON

CROSS-REFERENCE TO RELATED APPLICATIONS

This application claims the benefit under 35 U.S.C. § 120 as a continuation application of U.S. patent application Ser. No. 15/268,407 filed on Sep. 16, 2016, which in turn claims the benefit under 35 U.S.C. § 119(e) as a nonprovisional application of U.S. Prov. App. No. 62/220,195 filed on Sep. 17, 2015. Each of the foregoing applications are hereby incorporated by reference in its entirety. Any and all applications for which a foreign or domestic priority claim is identified in the Application Data Sheet as filed with the present application are hereby incorporated by reference under 37 CFR 1.57.

BACKGROUND

Field of the Invention

Certain embodiments disclosed herein relate generally to a cage for use with a medical balloon, such as an angioplasty balloon. Methods of manufacturing the cage and treatment methods involving the cage are also disclosed, as well as various wedge dissectors and features of splines that can be used with the cages. Among other things, the wedge dissectors can be used to create perforations in plaque in a blood vessel in an effort to control crack propagation and to reduce flow limiting dissections.

Description of the Related Art

Atherosclerotic occlusive disease is the primary cause of stroke, heart attack, limb loss, and death in the United States and the industrialized world. Atherosclerotic plaque forms a hard layer along the wall of an artery and is comprised of calcium, cholesterol, compacted thrombus and cellular debris. As the atherosclerotic disease progresses, the blood supply intended to pass through a specific blood vessel is diminished or even prevented by the occlusive process. One of the most widely utilized methods of treating clinically significant atherosclerotic plaque is balloon angioplasty.

Balloon angioplasty is a method of opening blocked or narrowed blood vessels in the body. The balloon angioplasty catheter is placed into the artery from a remote access site that is created either percutaneously or through open exposure of the artery. The catheter is passed along the inside of the blood vessel over a wire that guides the way of the catheter. The portion of the catheter with the balloon attached is placed at the location of the atherosclerotic plaque that requires treatment. The balloon is generally inflated to a size that is consistent with the original diameter of the artery prior to developing occlusive disease.

When the balloon is inflated, the plaque is stretched, compressed, fractured, or broken, depending on its composition, location, and the amount of pressure exerted by the balloon. The plaque is heterogeneous and may be soft in some areas or hard in others causing unpredictable cleavage planes to form under standard balloon angioplasty. Balloon angioplasty can cause plaque disruption and sometimes even arterial injury at the angioplasty site.

SUMMARY

There is a continuing need to improve the methods for treating occlusive disease, including balloon angioplasty and other related treatment systems. In some embodiments a cage can be positioned around a medical balloon, such as an angioplasty balloon, to assist in a medical procedure. The cage can include at least first and second rings and a plurality of strips. Each strip can extend longitudinally between the first and second rings. Moving the cage to an expanded position can move the first and second rings closer together while expanding the strips. In some examples, the cage may further include spikes on the strips that can be used as wedge dissectors to dissect plaque in a vessel, among other things.

In some embodiments, disclosed herein is a medical balloon catheter, and wedge dissectors and strips that can be configured to be attached to a medical balloon catheter or other expandable member. The balloon catheter can include any number of the following: an elongate member having an inner lumen, the elongate member defining a longitudinal axis; an expandable balloon connected to the elongate member at a distal end of the elongate member; and a plurality of strips, each strip of the plurality of strips including a plurality of wedge dissectors spaced apart along a surface of each strip, each strip extending longitudinally along an outer surface of the balloon. The wedge dissectors can include a strip-facing base surface directly adjacent a surface of each of the strips and an unhoned radially outward facing surface having a length between a proximal edge of the radially outward facing surface and a distal edge of the radially outward facing surface and defining a height of each wedge dissector. The radially outward facing surface has a first width at the proximal edge, a second width smaller than the first width between the proximal edge and the distal edge, and a third width at the distal edge larger than the second width. In some embodiments, the second width corresponds to a single point along the length of the radially outward facing surface. The second width can correspond to a central segment having a central length in between the proximal edge and the distal edge. The length of each strip can be less than a length of the outer surface of the balloon coaxial to the length of each strip. The length of each strip can also be between about 3% and about 6% less than the length of the outer surface of the balloon coaxial to the length of each strip. The total length of the radially outward facing surface of each wedge dissector can be less than a total length of the strip-facing base surface of each wedge dissector. The radially outward facing surface can be, for example, one or more curved and/or chamfered surfaces. The radially outward facing surface can have a first height at the proximal edge and a second height between the proximal edge and the distal edge, wherein the second height is greater than the first height. In some cases, a maximal height of the radially outward facing surface is at a midpoint between the first unbounded edge and the second unbounded edge. In some cases, a maximal height of the unbounded surface can be offset from a midpoint between the proximal edge and the distal edge. In some embodiments, a lateral surface segment of the wedge dissector from the strip-facing base surface to the proximal edge has a first segment with a first slope and a second segment with a second slope different from the first slope. The strip can include a textured surface. In some embodiments, the strip can include a plurality of tabs on an inferior-facing surface of the strip opposite the wedge dissectors. A plurality of reliefs on the strip can also be included. The strips can in some cases include an elongate length and first and second lateral edges. The first and second lateral edges of the plurality of strips can be circumscribed by an adhesive. In some embodiments, a hydrophilic slip layer can surround the outer surface of the balloon, the strips, and the wedge dissectors. In some embodiments, at least one polymer retention layer surrounds the outer surface of the balloon, the strips, and the wedge dissectors. The balloon can also include cones about the lateral ends of the balloon. The cones can have a maximal outer diameter that is greater than about 5% of the maximal outer diameter of the balloon. In some cases, the cones comprise rails oriented with longitudinal axes of the strips.

The cage can be assembled and/or manufactured in many ways, including, in some examples, an extrusion process, material removal from a tube, or by splitting a wire to form the strips.

The cage can assist a medical procedure in many ways. For example, the cage may cover a drug coating on the balloon pre-deployment. In some variants, when the cage is expanded, the cage may allow access to the drug coating on the surface of the balloon. In this way, the cage can prevent or reduce the chances that the drug will become diluted during delivery or will treat areas of the body not intended for treatment.

As another example, the cage can prevent or reduce dog boning of the balloon by increasing the resistance to expansion of the combined balloon and cage at the ends of the cage as compared to the center of the cage.

In some embodiments, a balloon catheter can comprise an elongate member, a balloon, and a cage. The elongate member can have an inner lumen, the elongate member defining a longitudinal axis. The balloon can be connected to the elongate member at a distal end of the elongate member. The cage can be for positioning about the balloon. The cage can comprise a plurality of strips and a plurality of rings. The plurality of rings can be configured to secure the plurality of strips to the balloon catheter. Each strip of the plurality of strips can have a first ring of the plurality of rings at a distal end, a second ring of the plurality of rings at a proximal end. At least a portion of the strip between the distal and proximal ends remains uncovered by and/or unconnected to any ring. The balloon and cage are configured to have an initial state and an expanded state, the plurality of strips configured to move with the balloon as it moves toward the expanded state.

According to some embodiments of the balloon catheter, at least some of the rings of the plurality of rings comprise a heat shrink material. Further each strip of the plurality of strips can include a plurality of wedge dissectors spaced along a surface of the strip, each strip extending longitudinally along an outer surface of the balloon. The plurality of rings can secure the plurality of strips to distal and proximal ends of the balloon. At least some of the strips of the plurality of strips can be secured with rings at intermediate points of the balloon. The strip may be secured at intermediate points and/or at the ends.

In some embodiments, at least some of the rings of the plurality of rings comprise a part ring having a top layer of heat sink material and a bottom layer, an end of a strip of the plurality of strips sandwiched between the top layer and the bottom layer. Some embodiments can include hooks on the strips, grooves on the strips or rings, springs, and other features.

In some embodiments, a plurality of polyurethane coatings in combination with a series of strips collectively produce a cage. In one such embodiment the cage is comprised as a full or partial single top layer or multiple layers of urethane, polyurethane, or other polymer material and a bottom layer of urethane, polyurethane, or other polymer material, and a plurality of strips sandwiched between the top layer/s and the bottom layer. Some embodiments can include hooks on the edges of strips, grooves on the strips or rings, springs, and other features.

A method of retrofitting a balloon catheter with a cage can comprise any of the below steps. Positioning a plurality of strips around an inflated balloon of a balloon catheter, the strips being positioned equally spaced around the inflated balloon. Advancing rings of heat shrink material over the balloon so that each end of the strips of the plurality of strips is covered by a ring heat shrink material. Heating the rings of heat shrink material to shrink the rings of heat shrink material to thereby secure the plurality of strips to the balloon, at least a portion of each strip of the plurality of strip between distal and proximal ends of the strip remaining uncovered by and/or unconnected to any ring of heat shrink material.

A method may further include positioning the strips to extend primarily longitudinally, and/or positioning the strips serially in rows around the balloon with 4 rows, each having between 2-6 strips per row. The strips can be attached either permanently or temporarily to the balloon with an adhesive.

Advancing rings of heat shrink material over the balloon further may comprise covering a distal end of distal-most strips of the plurality of strips with a single ring of heat shrink material. Further, advancing rings of heat shrink material may include covering a proximal end of proximal-most strips of the plurality of strips with a single ring of heat shrink material. Still further, it can include covering a proximal end of distal-most strips of the plurality of strips and a distal end of proximal-most strips with a single ring of heat shrink material.

In some embodiments, a cage can be positioned around an angioplasty balloon. The cage can include first and second rings and a plurality of strips. Each strip of the plurality of strips can extend longitudinally between the first and second rings. The cage can have a pre-expansion position and an expanded position, wherein moving to the expanded position moves the first and second rings closer together while expanding the strips.

A method of making a cage for an angioplasty balloon can comprise extruding a plastic tube with a plurality of spaced apart splines positioned longitudinally along the tube; cutting at least one of the splines of the plurality of splines to form a plurality of spikes positioned circumferentially around the tube; and cutting the tube to form a plurality of longitudinally extending strips, each strip including at least one spike of the plurality of spikes.

A method of making a cage for an angioplasty balloon can comprise splitting a wire into a plurality of longitudinally extending strips; cutting at least two longitudinally extending strips of the plurality of longitudinally extending strips to form a plurality of spikes spaced apart along the longitudinally extending strip; and connecting the at least two longitudinally extending strips to a first ring and a second ring such that each strip of the plurality of longitudinally extending strips extends between the first and second rings.

A method of protecting an angioplasty balloon with a drug coating can comprise providing an angioplasty balloon with a drug coating; providing a cage having a pre-expansion position and an expanded position, the cage comprising: first and second rings; and a plurality of strips, each strip of the plurality of strips extending between the first and second rings; wherein the cage is positioned over the angioplasty balloon such that in the pre-expansion position the cage covers the angioplasty balloon radially such that none, or substantially none, of the surface of the angioplasty balloon with the drug coating is exposed, and moving to the expanded position moves the first and second rings closer together while expanding the strips and exposing the angioplasty balloon surface.

A method of treating a diseased blood vessel can comprise advancing an angioplasty balloon, optionally with a drug coating, to a treatment site in a diseased blood vessel, the angioplasty balloon having a cage positioned over the angioplasty balloon, the cage having a pre-expansion position and an expanded position, the cage comprising: first and second rings; and a plurality of strips, each strip of the plurality of strips extending between the first and second rings; expanding the angioplasty balloon at the treatment site, where expanding the angioplasty balloon further comprises moving the first and second rings closer together while expanding the strips, the cage preventing or reducing dog boning of the angioplasty balloon by increasing the resistance to expansion of the combined angioplasty balloon and cage at the ends of the cage as compared to the center of the cage.

In some embodiments, a cage for positioning about an angioplasty balloon can include a plurality of rings and a plurality of strips. The plurality of rings can be non-expandable. At least one of the plurality of rings can be configured to be disposed about a first end of an angioplasty balloon, and at least one of the plurality of rings can be configured to be disposed about a second end of the angioplasty balloon. Each of the plurality of strips can include a plurality of protrusions positioned on the surface of each of the plurality of strips. Each of the plurality of rings can be configured to attach to each end of the plurality of strips. The plurality of strips can be attached to the plurality of rings through a coupling. In some embodiments, the cage can have a first length and a second length. The second length is shorter than the first length, and the plurality of rings are closer in proximity with each other such that each of the plurality of strips bends away from each of the plurality of strips.

BRIEF DESCRIPTION OF THE DRAWINGS

These and other features, aspects and advantages are described below with reference to the drawings, which are intended to illustrate but not to limit the invention. In the drawings, like reference characters denote corresponding features consistently throughout similar embodiments.

FIGS. 16A-C show a plurality of embodiments of strips secured by a ring.

FIGS. 25A-25K illustrate various embodiments of strips with reliefs in various locations.

FIGS. 25L and 25M illustrate embodiments of method of stabilizing strips during the laser cutting manufacturing process and involving temporary tabs, according to some embodiments.

FIG. 25N illustrates embodiments of an adhesive ramp for bonding lateral ends of a strip to the balloon surface, according to some embodiments.

FIG. 25P illustrates a series of cone rails or struts, according to some embodiments.

DETAILED DESCRIPTION

Figure 1A:
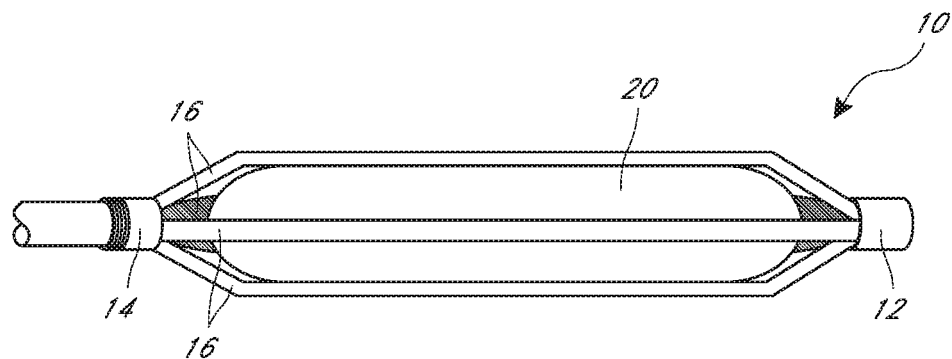
FIG. 1A illustrates a cage positioned on an angioplasty balloon in an expanded position.
Figure 1B:
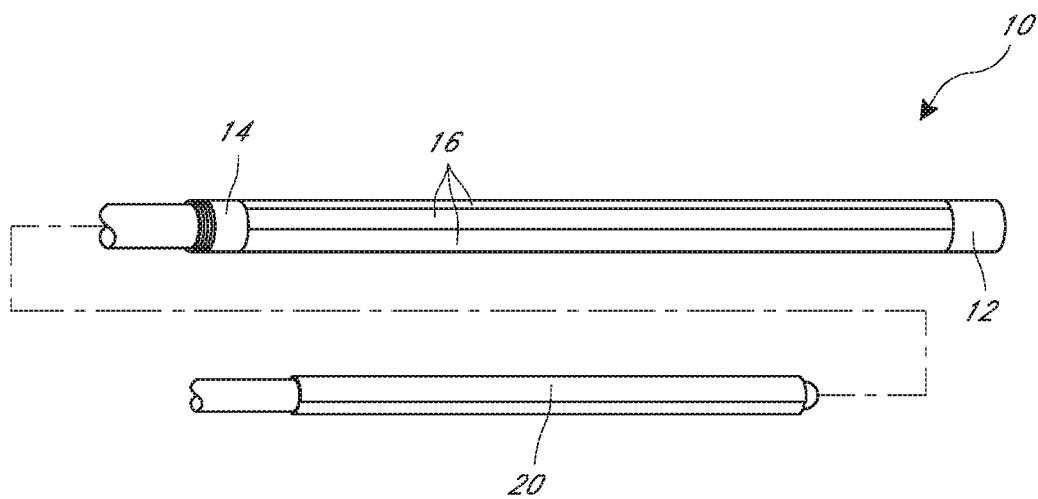
FIG. 1B shows an exploded view of an angioplasty balloon that can be positioned within a cage, both being shown in a pre-expanded position.

FIGS. 1A and 1B illustrate an embodiment of a cage 10 positioned on an angioplasty balloon 20. FIG. 1A shows an expanded position and FIG. 1B shows how the angioplasty balloon can be advanced into the cage. The cage 10 is described herein primarily with respect to an angioplasty balloon 20 and an angioplasty procedure. It is to be understood that the cage 10 can be used with other types of medical balloons and in other procedures.

The cage 10 can include a first ring 12 and second ring 14, and a plurality of strips 16. Each strip can extend longitudinally between the first ring 12 and the second ring 14. The strips and rings can be made of a monolithic part formed from a single piece of material. Thus, the first and second rings can be the ends of a cut tube, for example. The strips and rings can also be made of separate materials and be connected together. As shown the illustrated cage of FIGS. 1A and 1B has five strips 16, though other numbers of strips can be used such as 2, 3, 4, 5, 6, 7, 8, 9, 10, etc.

Figure 2:
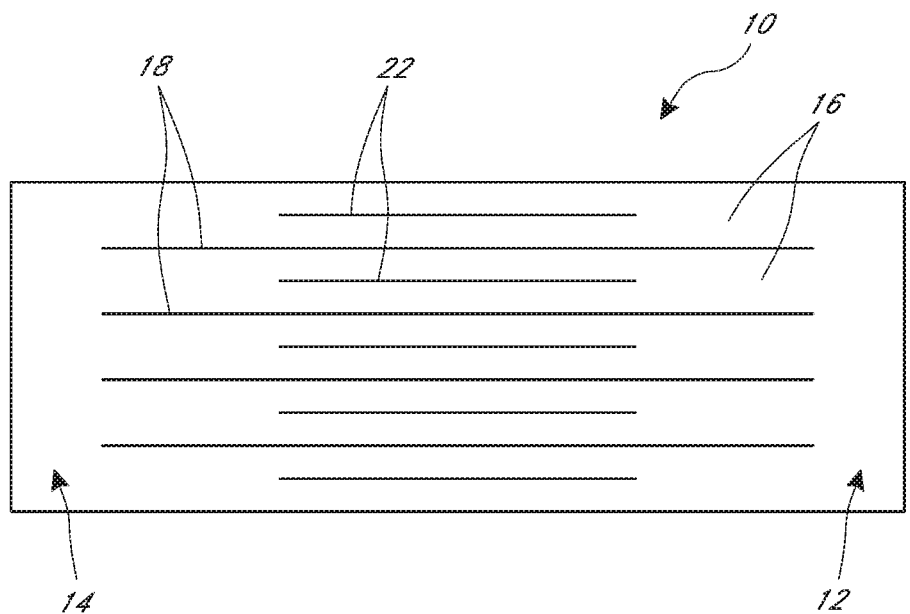
FIG. 2 shows a schematic representation of a cage laid flat showing both long and short slits.

FIG. 2 shows a plan view of a cut tube embodiment of cage, though some embodiments of cage can alternatively be made of a single flat piece of material. The material can be elastic or semi-elastic and made from a polymer, copolymer, a metal, alloy or combination of these. The strips are typically designed to enable the balloon 20 to be inflated multiple times. As well, the strips 16 can be configured such that the cage 10 can apply forces both longitudinally and axially or in orientations that enable the strips 16 to return to this original position.

In some embodiments the cage 10 is prefabricated, packaged, and sterilized separately from the balloon 20, allowing the physician to position the cage 10 around a medical balloon 20, such as an angioplasty balloon, to assist in a medical procedure at the time of the procedure. FIG. 1B shows the balloon 20 in a folded state prior to deployment and prior to placement within the cage 10. The folded balloon 20 can be advanced into the cage 10 without requiring expansion or change in shape of the cage 10. The cage 10 can completely surround and enclose the balloon 20 prior to balloon deployment or expansion. The cage 10 in the pre-expanded state can be longer than the balloon 20. This can allow for movement of one or both ends of the cage 10 towards each other while the device (e.g. balloon 20) expands. The cage 10 can be free floating over the balloon 20. One or both ends 12, 14 of the cage 10 may be fixed to the balloon 20 or another part of the delivery device. In some embodiments the cage 10 is not attached to any portion of the balloon 20 that expands. This can prevent the cage 10 from interfering with the balloon 20 as it expands.

In some examples, a cage 10 can be used with an angioplasty balloon 20 with a drug coating to can protect the drug coating. The cage 10 can prevent or reduce the premature exposure of the drug to the blood vessel. As will be understood with reference to FIG. 1B, the cage 10 can be positioned over a drug coated angioplasty balloon 20 in the pre-expansion state to prevent premature exposure of the drug to the blood vessel. The cage 10 can cover the balloon 20 radially such that a minimal amount, or substantially none, of the surface of the angioplasty balloon 20 with the drug coating is exposed. The balloon 20 and cage 10 can be advanced to a treatment location in this configuration. Though not shown, the system may be advanced over a guidewire within the vasculature.

As illustrated in FIG. 1A, the cage 10 can be moved to an expanded position. In the expanded position the first 12 and second rings 14 are closer together and the strips are expanded thereby exposing the angioplasty balloon surface. In this position, the drug can be placed into contact with diseased tissue in the blood vessel.

In currently available systems, it is generally difficult to predict how much drug will reach the diseased tissue. There are many factors that limit the ability to accurately predict how much drug will be transferred to the diseased tissue. For example, blood flow can dilute the drug on the balloon 20 as it is advanced to the treatment site. Furthermore, navigating the device through the blood vessel can cause the balloon 20 to rub against the endoluminal surface thereby removing some of the drug as the balloon 20 is being advanced to the treatment location. Therefore, in some examples, the cage 10 can offer a physical barrier to protect the drug covering of the balloon 20 during advancement to the treatment location. In this way the cage 10 can be used such that balloon 20 and drug covering are exposed to blood flow in a vessel only during expansion of the balloon 20 as the space between the strips increases. In this way, the cage 10 can prevent or reduce the chances that the drug will become diluted or that the drug will treat areas of the body that are not meant for treatment. In some variants, this can allow for more controlled delivery of the drug with a reduction in the amount of drug necessary to be coated on the balloon 20.

In some embodiments, the folded balloon 20 can be positioned entirely within the cage 10. As is illustrated in FIG. 1A, the cage 10 can have slits between each of the strips 16. In some variants, the slits can be formed by cutting between each of the strips 16 to separate them from a single piece of material. In other embodiments, the slits are really just the space between adjacent strips. The space between strips can be a minuscule amount, such as would formed by a laser cut, or much larger, such as equal to or greater than a width of the strip itself. Depending on the size of the slits, the exposed surface of the balloon 20 in the pre-expansion position is not more than 50% and can be as low as 25%, 10%, 5%, 1%, or less.

As has been described previously, expansion of the balloon 20 moves the first 12 and second rings 14 closer together while moving the strips 16 further apart radially. With the strips 16 in an expanded position, the balloon 20 is more exposed to and can interact with the vessel wall. In the expanded position, the balloon 20 can deliver a drug, stem cells, or other treatment to the vessel wall or to a diseased area of the vessel wall. When the balloon 20 is fully expanded, the exposed surface of the balloon 20 not covered by the strips 16 can be between 65% and 99%, 75% and 99%, more commonly 80% and 99%, or most commonly 90% and 99%, among other ranges.

Drug delivery using the cage 10 can be employed before, during, or after an angioplasty procedure. At the same time, it is not required that the cage cover the entire balloon, or be used to control or assist with drug delivery.

Figure 3:
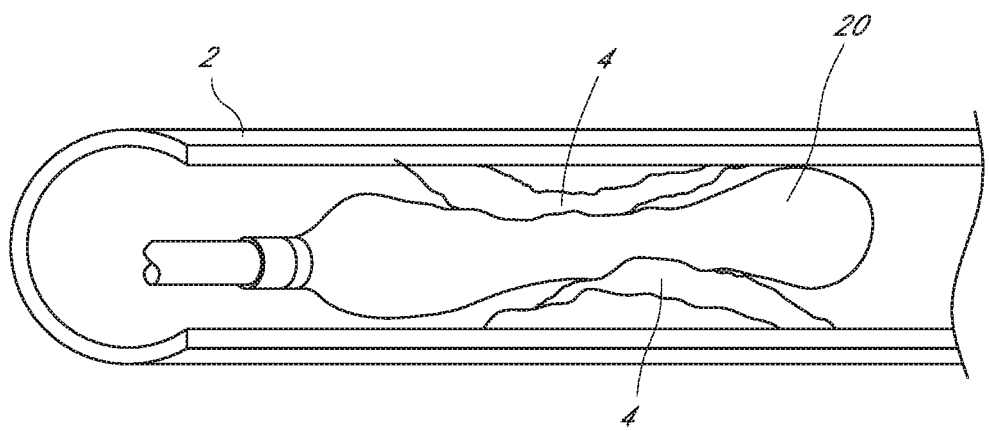
FIG. 3 shows an angioplasty balloon within a vessel at a treatment site that is experiencing dog boning.

In some embodiments, a cage 10 can be used to prevent or reduce dog boning of the balloon 20 in an angioplasty procedure. This may be in addition to, or instead of assisting with drug delivery. FIG. 3 shows an angioplasty balloon 20 within a blood vessel 2 at a treatment site. As illustrated, the angioplasty balloon 20 is experiencing dog boning as it is expanding. The plaque buildup 4 resists expansion of the balloon 20, forcing both ends of the balloon 20 to expand first, rather than focusing the expansion energy in the center of the balloon 20 at the plaque 4 where it is needed most.

To prevent dog boning, the cage 10 as shown in FIG. 1A, can constrain the balloon 20 upon expansion to encourage the middle of balloon 20 to expand first. This is because the middle area of the cage 10 can be designed to have the least resistance to expansion, being farthest away from the ends where the strips are confined by rings. This can prevent or reduce dog boning of the balloon 20 independent of the disease morphology or arterial topography the balloon 20 is expanding within.

Dog boning usually occurs where a balloon 20 expands in a vessel with plaque where the plaque resists expansion, forcing the ends of the balloon 20 to expand first (due to lack of resistance) such that the balloon 20 takes the shape of a dog bone. By enveloping a balloon 20 with a cage 10 and configuring the rings to display different expansion resistance, the ends of the balloon 20 can have the highest resistance and the center of the balloon 20 have the lowest resistance. Therefore, the cage 10 can help control and limit expansion of the balloon 20, as the balloon 20 will tend to expand more readily in the center which is typically the area of disease.

The pattern and orientation of the strips 16 can influence expansion and dog boning. Returning to FIG. 2, the short slits 22 positioned in the center of the strips 16 can reduce rigidity in the center of each of the strips 16. This can help reduce the likelihood of dog boning by further reducing resistance to expansion in the center of the cage 10.

The cage may further include spikes or wedge dissectors on the strips. The spikes can be used as a vessel preparation tool before a secondary treatment, or during a primary treatment. For example, the spikes can assist with cutting and/or perforating plaque before or during an angioplasty procedure. This may be in addition to, or instead of assisting with drug delivery and/or preventing dog boning. It will be understood that any of the embodiments described herein can provide any of these benefits and/or be used in any of these procedures, as well as the other benefits and procedures described herein.

Spikes can be positioned on the strips in any number of different orientations and configurations as will be described further below. The spikes can be any of the spikes discussed in U.S. Pat. No. 8,323,243 to Schneider et al., issued Dec. 4, 2012 and incorporated by reference herein in its entirety. The spikes and cage can also be used in accordance with the plaque serration methods and other methods also described therein.

Figure 4A:
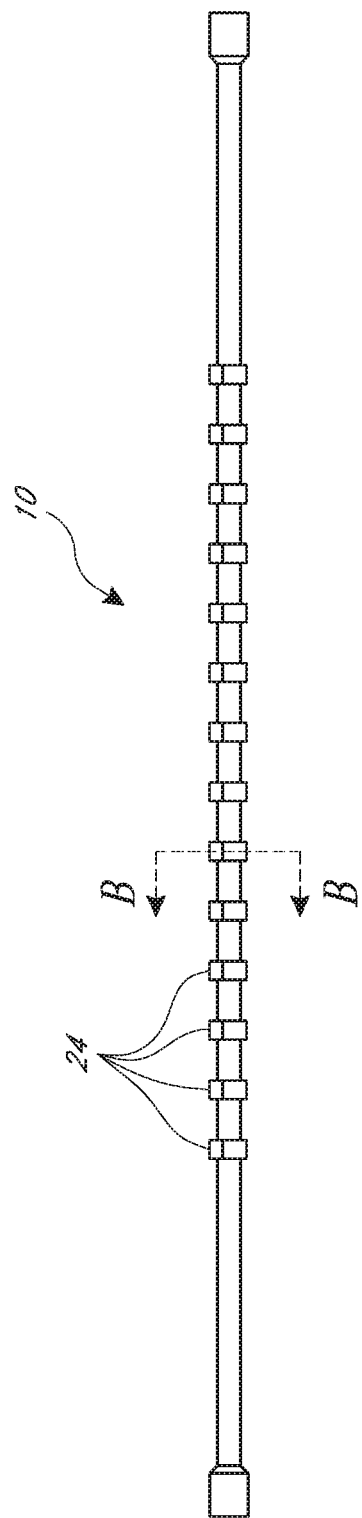
FIG. 4A shows an unfinished cage during manufacturing being cut from a tube.
Figure 4B:
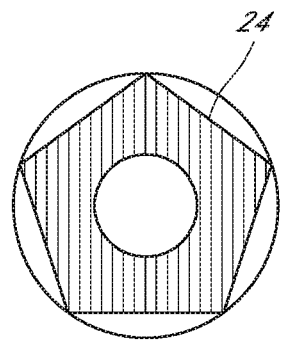
FIG. 4B is a cross-section of the unfinished cage of FIG. 4A taken along line B-B.
Figure 4C:
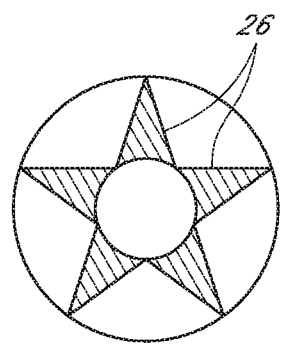
FIG. 4C shows the cross-section of FIG. 4B after an additional manufacturing step.
Figure 4D:
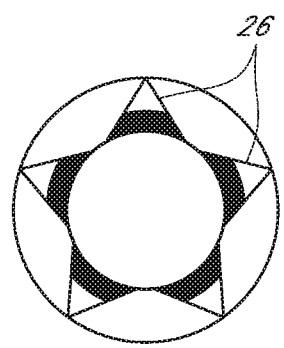
FIG. 4D illustrates a cross-section of another embodiment with a larger interior lumen.

The cage 10 can be made in many ways. For example, an extrusion process may be used, a tube may be cut, and/or a wire split as will be described in more detail below. Beginning with FIGS. 4A-5B, various embodiments of cages will be described. FIGS. 4A and 5A show embodiments of cages 10 during the manufacturing process. The cages 10 are each in the form of a tube with a plurality of splines 24 spaced apart on the tube. In some embodiments, the tube can be pre-formed and then machined to the illustrated shape. The tube can be made of metal or plastic among other materials. In other embodiments, the tube is extruded to form the illustrated shape. For example, a method of making the tube can include extruding a plastic tube with a plurality of spaced apart splines 24 positioned longitudinally along the tube. Cross-sections of the cages are shown in FIGS. 4B-D and 5A.

After forming the tube with the splines 24, material from the tube can be removed to form the slits and strips 16. Either as part of removal process, or before creating the slits, the splines may be shaped to form different shaped spikes or wedge dissectors 26. For example, the splines 24 illustrated in FIG. 4B can be machined to form the sharp wedge dissectors 26 as shown in FIGS. 4C and 4D. In some embodiments, the splines 24 can be manufactured with an additive process and shaped initially like the illustrated wedge dissectors 26 without requiring additional machining or other work.

Figure 4E:
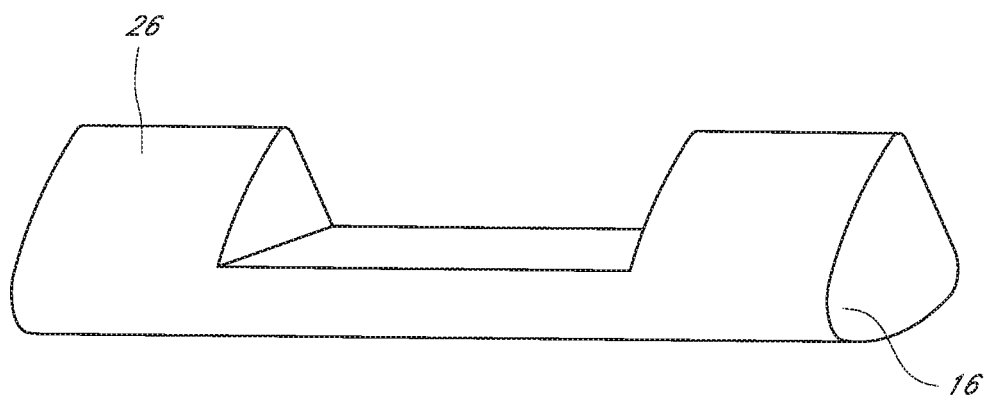
FIG. 4E shows a detail view of a portion of another embodiment of cage.
Figure 5A:
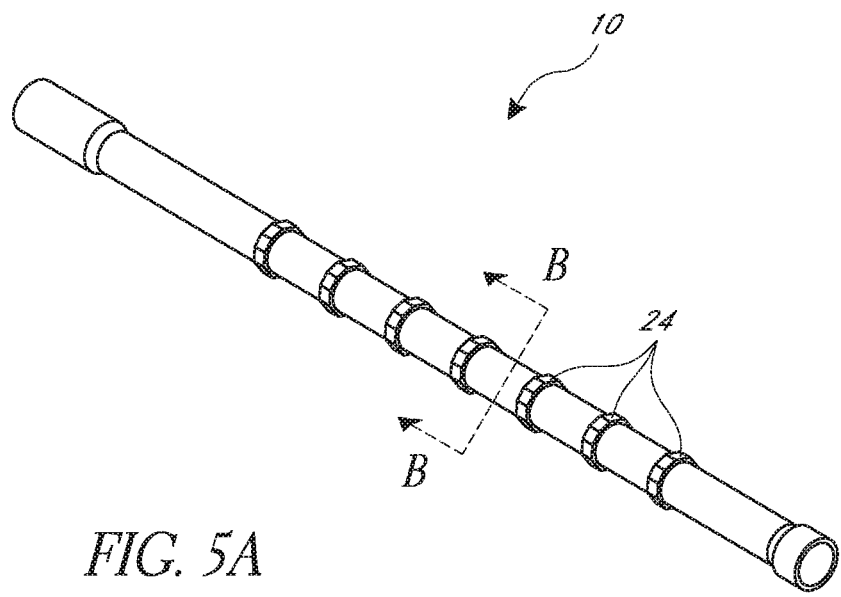
FIG. 5A shows another embodiment of an unfinished cage during manufacturing.
Figure 5B:
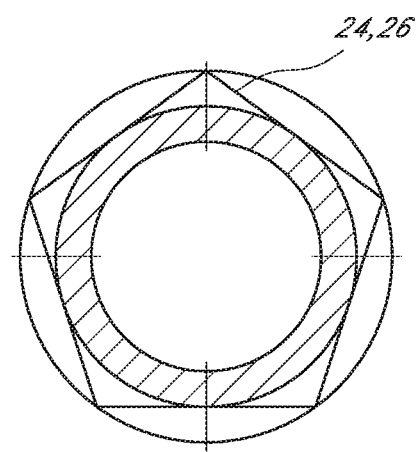
FIG. 5B shows a cross-section of the unfinished cage of FIG. 5A taken along line B-B.

Looking now to FIG. 4E, an enlarged detail view of a portion of a cage is shown. In this embodiment, the strip 16 has been formed with a plurality of spikes or wedge dissectors 26. In some embodiments, from the base of the unfinished cage of FIGS. 4A and 4B, a slit can be cut in the tube to form adjacent strips. The wedge dissectors 26 can be shaped like a tent or axe head with an elongated tip and base, both of which extend longitudinally, along the longitudinal axis of the tube. The wedge dissectors 26 can assist with cutting and/or perforating plaque before or during an angioplasty procedure. The space between the wedge dissectors 26 can be machined or otherwise formed to remove material and increase the flexibility of the strip. The space between the wedge dissectors 26 is shown as being twice the length of the wedge dissector 26, though other spacing can also be used. Typically spacing length can be 4:1 to 3:1 space to length and more commonly 3:1 to 1:1 space to length.

Turning to manufacturing of the splines, in some embodiments, the splines 26 are fabricated from a tube of material, where the cage 10 is a plastic extruded tube with splines that are cut, ground, electrical discharge machined, or molded to form the wedge dissectors 26. The tube can be manufactured with slits along its length. In some examples, the ends of the tube remain intact in order to forming rings. In some variants, the strips 16 are spaced apart with some or all the strips 16 having spikes or wedge dissectors 26. As will be understood from the above discussion, in the embodiments shown in FIGS. 4A-5B five slits would be made to form outward points.

In some embodiments, a method of making a cage 10 for an angioplasty balloon 20 can comprise first extruding a plastic tube with a plurality of spaced apart splines positioned longitudinally along the tube. In some examples, the method can then include cutting at least one of the splines of the plurality of splines to form a plurality of spikes or wedge dissectors 26 positioned circumferentially around the tube. In some variants, the method can further include cutting the tube to form a plurality of longitudinally extending strips 16, each strip including at least one spike of the plurality of wedge dissectors 26.

Figure 6A:
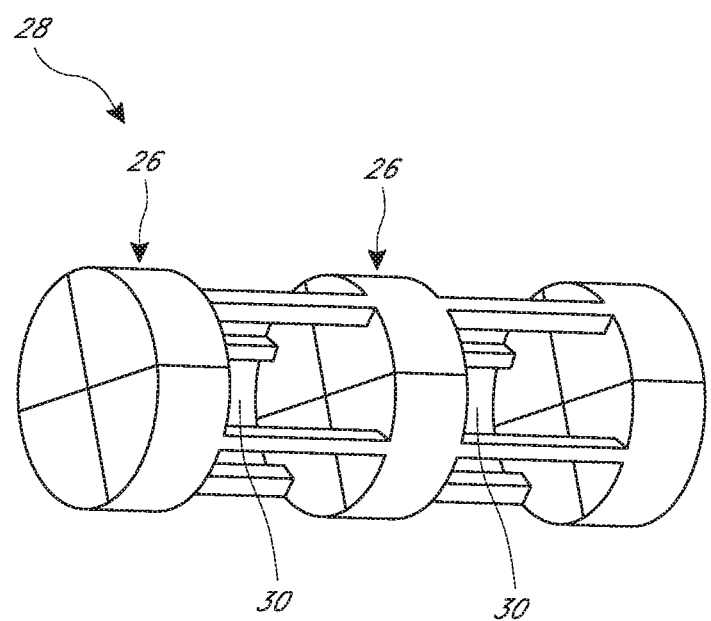
FIG. 6A shows a wire cut to form strips and wedge dissectors for an embodiment of a cage.
Figure 6B:
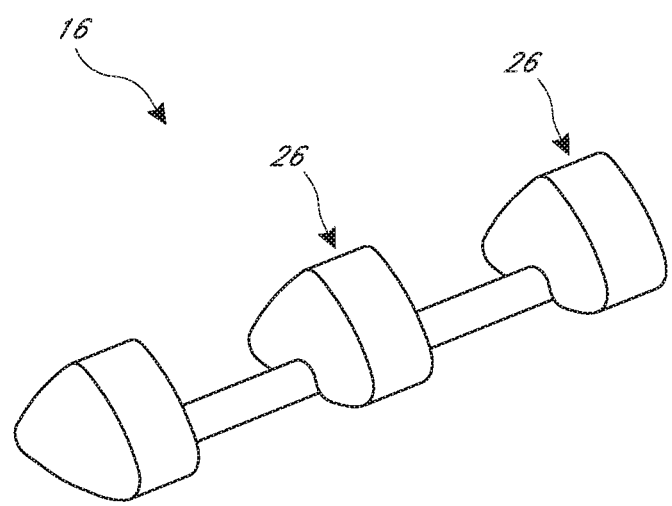
FIG. 6B shows a section of the cut wire of FIG. 6A.

Looking now to FIGS. 6A-6B, another method of manufacturing a cage 10 will be described. A wire 28 can be split or cut to form three or more strips 16 that can be used as part of forming a cage 10. In some examples, the wire 28 is constructed of an alloy, or polymeric material. Any number of different manufacturing methods can be used including laser cutting and electrical discharge machining. In some variants, the wire 28 can be divided into sections, such as four quarters. In some embodiments, square or other shaped holes 30 can be cut into the wire 28 to form spaces between the wedge dissectors 26. Each of the sections of wire can then be separated to form the strips 16 of the cage 10. A cage 10 can be assembled with a plurality of rings and include any number of strips 16. In some examples, a cage 10 can be assembled from 1, 2, 3, 4, 5, 6, 7, 8 or more strips 16.

Systems and Methods for Connecting Individual Strips

Strips 16 can be attached in many ways to form the cage 10. In addition, to forming the strips from a wire, they can also be extruded and/or formed from a flat piece of material and/or a tube. For example, it will be understood that the embodiments described with reference to FIGS. 2, 4A-5B can be modified to provide individual strips that can then be connected to form a cage.

Figure 7:
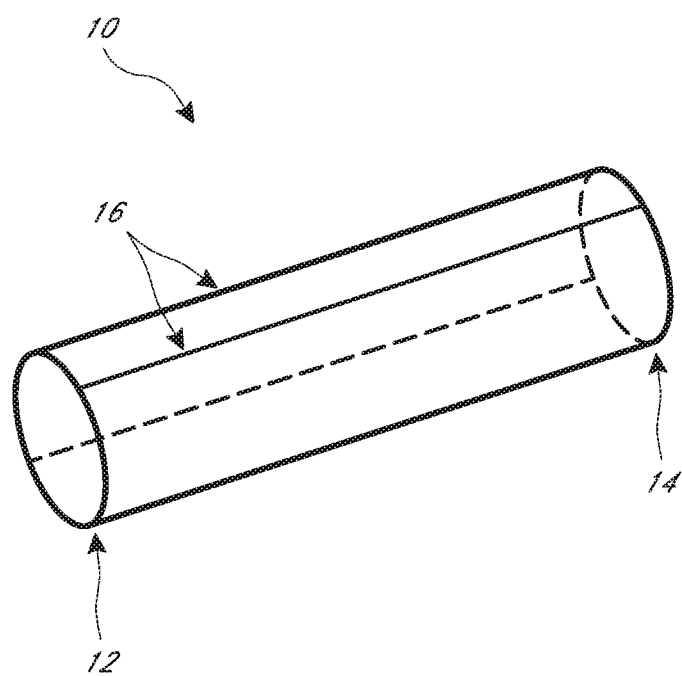
FIG. 7 shows a schematic view of a plurality of strips that are connected by two rings to form a cage.

In some embodiments, strips can be connected with two or more rings 12, 14 to form a cage 10. For instance, the individual strips of the cage 10 may be bonded to rings on either end. As illustrated in FIG. 7, each individual strip 16 is secured on either end by rings 12, 14. In constructing the cage 10, the strips 16 can be attached to the rings 12, 14 first before positioning around a balloon, or the cage can be assembled around a balloon. For example, one or more strips can be placed onto the surface of the balloon 20 before connecting to the rings. The cage 10 may be permanently fixed to one or both ends of the balloon 20 or to the balloon catheter. In some embodiments, the rings 12, 14 can hold the strips against a portion of the balloon or the balloon catheter. The strips 16 can also help to keep the balloon 20 in a compressed state prior to deployment and can assist in deflating the balloon after expansion.

The rings 12, 14 are typically circular bands, though they can be a band of any number of shapes including oval, square, elliptical, rectangular, etc. The rings can also be capable of producing a binding and/or restraining force. The rings 12, 14 can be any number of different materials including one or more of a metal, polymer, copolymer, elastomer, thermoplastic elastomer, glue, or hydrogel. The rings can be rigid or flexible.

In some examples, the rings 12, 14 can be composed of a heat shrink material or a material with elastic properties that binds, captures, or restrains the plurality of strips 16 and prevents or limits the strips 16 from moving, sliding, tilting or twisting at any point along the length of the strips but especially at either end of the balloon 20. When the rings are elastic, super elastic, or thermally active, the rings can be placed about the strips and allowed to shrink onto the strips such that the strips 16 are retained against the outer diameter of the balloon 20. Preferably, the rings and strips are positioned around a balloon in a fully expanded state and then heat is applied to the heat shrink type rings. In other embodiments, the heat shrink types rings are applied with the balloon in a deflated state.

As discussed with respect to FIGS. 1A and 1B the cage can be performed and slid onto the balloon. But, in some embodiments, assembling the cage around the balloon can allow for a smaller cage design. In retrofitting the balloon 20, the rings can be advanced onto the balloon catheter from either side which may allow for a smaller ring inner dimension as compared to a cage with one ring that is advanced over a balloon.

The rings 12, 14 of the cage 10 can be configured to accommodate the balloon 20 as it transitions from a deflated to an inflated shape. Not unlike the configuration of the cage with balloon illustrated in FIG. 1B, the strips 16 of the cage 10 can be in contact with the balloon 20 when the balloon 20 is in a deflated configuration. As the balloon 20 inflates, each strip 16 bows in a concave orientation with the balloon 20 (FIG. 1A). In some examples, the strips 16 are free-floating and not bound to the balloon surface.

As the balloon 20 begins deflating, the material properties of the strips 16 can allow it to begin to return to their original position. This may be a completely flat position. As the strips 16 return to their original position, this can provide an additional force to assist the deflation of the balloon 20. As the strips move from the concave position to a flat linear position, the strips 16 move from an expanded length ("$L_e$") to a deflated length ("$L_d$") where $L_d$ is longer than $L_e$. The straightening of the strips 16 from $L_e$ to $L_d$ in the axial direction elongates the balloon 20 and assists in more complete balloon 20 deflation.

The rings 12, 14 can come in a variety of shapes and sizes that can secure the plurality of strips 16. The following discussion of certain illustrated embodiments, are but a few such examples.

Figure 8:
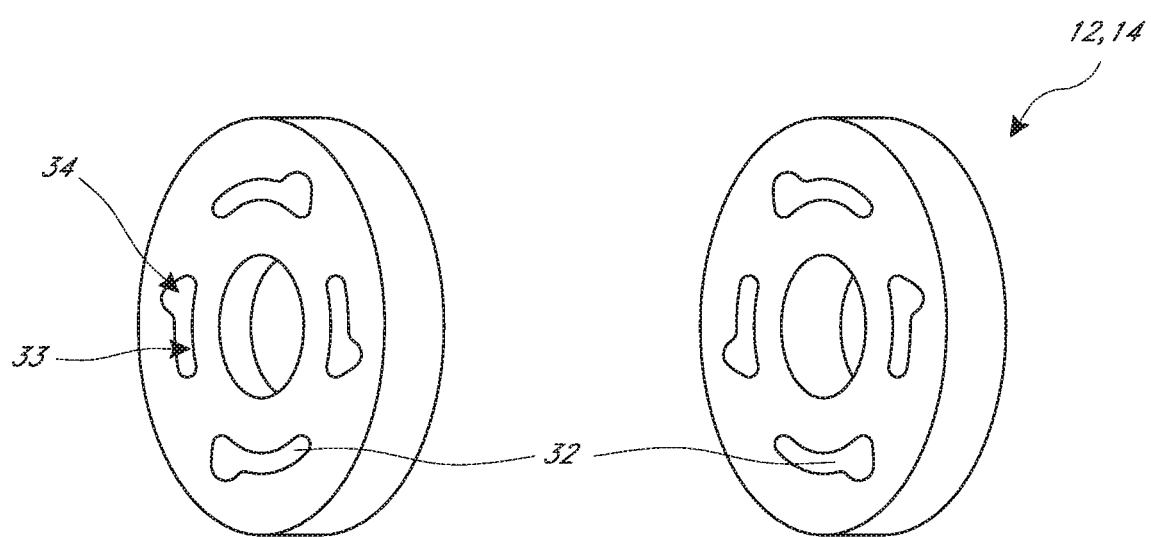
FIG. 8 illustrates a two-part ring that can be used to capture strips to form part of a cage.

The rings 12, 14 can connect to the strips 16 in a number of different ways. The rings can be mechanically attached to the strips 16 through a friction fit for example, or can be connected with an ultrasonic weld, adhesive, etc. Turning to FIG. 8, each ring 12, 14 can be a two-part ring that can connect to one or more strips 16 of the cage 10 by rotating the rings in opposite directions (e.g. clockwise and counterclockwise). The rings 12, 14 can include holes 32, through which the strips 16 can be advanced to connect to the ring. In particular, the asymmetrical shape of the holes 32 can be configured to accommodate a strip 16 with periodically spaced wedge dissectors 26 such as that illustrated in FIG. 6B.

As illustrated, the holes 32 can have a narrowed portion 33 and a wider portion 34. The wider portion 34 can be configured to accommodate the wedge dissector 26 while the narrowed portion 33 can be configured to accommodate the width of the strip 16 (i.e. the space between wedge dissectors). The strips 16 can be advanced through the holes 32 by fitting a wedge dissector 26 through the wider portion 34. In some examples, the strip 16 can then be secured by turning the rings 12, 14 such that the strip 16 is moved into the narrowed portion 33. This can secure the strips 16 to the rings 12, 14 as the wedge dissector 26 cannot move past the narrowed portion 33. As described above, both rings 12, 14 can be present at either end of the cage 10. Additionally, as illustrated in FIG. 8, because the holes 32 of the ring 12 and the holes 32 of the ring 14 are opposed, by rotating the two parts of the ring in opposite directions, this further prevents movement of the strips 16.

Figure 9A:
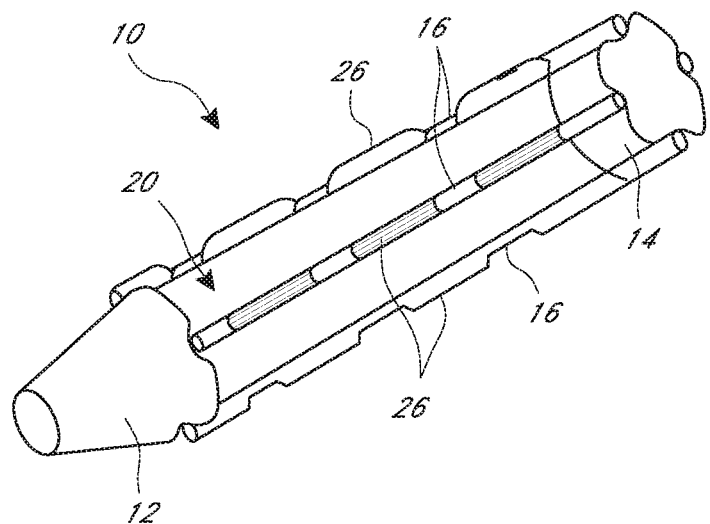
FIG. 9A is another embodiment of cage with a conical ring.

The strips 16 can be secured by rings 12, 14 that are formed from a variety of shapes. For example, FIG. 9A illustrates an embodiment of the cage 10 where the strips 16 are secured with a conical ring 12 at the distal end. The conical end can be the distal end of the balloon catheter and can provide an atraumatic end of the device.

Figure 9B:
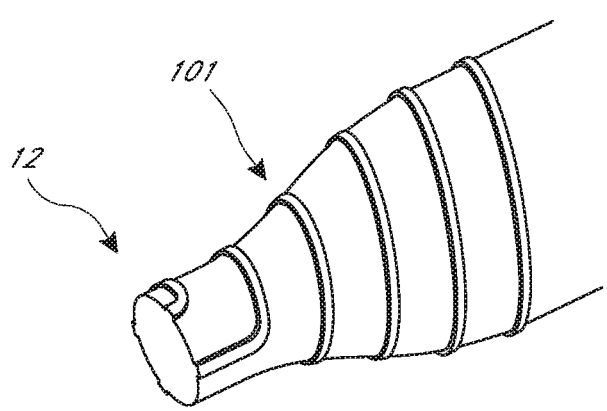
FIG. 9B is a perspective view of a ring with a tapered outer diameter wherein the ring includes a screw-like feature on its outer surface.

Similarly, FIG. 9B shows a ring 12 with a tapered outer diameter with a screw feature 101 on its outer surface. This screw feature 101 can provide either a negative or positive impression about the outer surface of the distal ring.

The ring 12 illustrated in FIG. 9B can serve a treatment purpose as well. In some examples, the tapered and screw features on the ring can assist the balloon 20 in navigating and entering a narrow lesion. The coiled outer surface 101 can be configured to provide a gripping or tunneling mechanism. This feature can allow the ring to aid the operator in navigating through occluded lesions (either totally or partially) and enable passage of the balloon 20 therein. The negative or positive impression 101 can be circumferential or patterned like a cork screw. In some embodiments, the negative or positive impression 101 can be macro in scale or have micro features that offer an enhanced surface to enable passage through a narrowing in a vessel. In some examples, the function of the outer surface 101 of the ring can be described as acting like a lubricant although the feature is mechanical in nature. This function can be further enhanced with hydrophilic, hydrophobic coating. The surface texture can also be modified to aid in passages with less penetration energy. In some embodiments, this can be accomplished by adding micro scales (as seen in porcupine quills) or enhanced surface roughness (as used in nature by mosquitos).

The ring 12 illustrated in FIG. 9B can be secured to strips 16 that are disposed about the surface of the balloon circumferentially in a helical fashion. In contrast to the linear strips 16 illustrated in FIG. 9A, the strips 16 attached to the tapered ring 12 can be wound around the balloon. A tapered or untampered ring 14 can be used at the proximal end of the balloon. In some examples, the configuration of the attached strips 16 can follow the same pattern as the negative or positive impression 101 on the ring 12.

Figure 10:
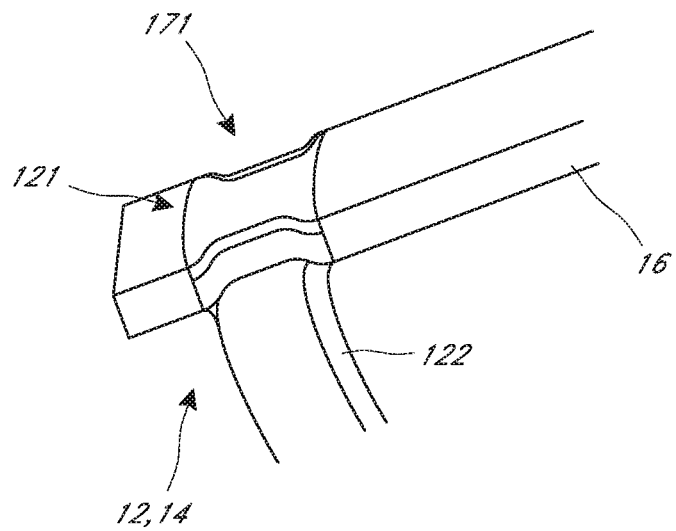
FIG. 10 shows the end of a strip configured to accommodate and be secured by a multi-layer ring to form an end of the cage.
Figure 11:
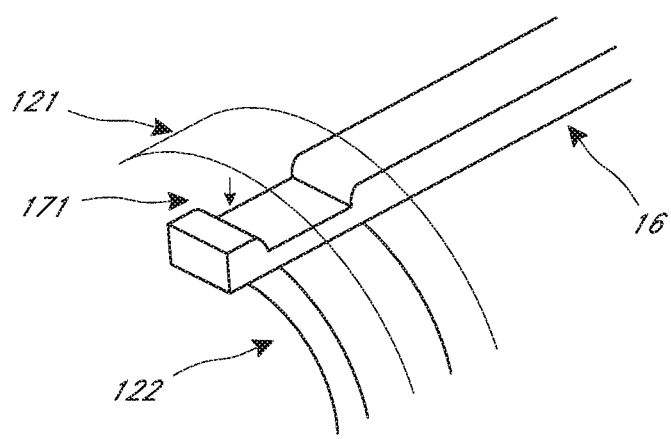
FIG. 11 illustrates another embodiment of the end of a strip configured to accommodate and be secured by a multi-layer ring to form an end of the cage.

Turning now to FIGS. 10-11, multiple layer rings will be discussed. A ring with multiple layers can be used to hold the strips between the layers. The ring can have at least a base layer 122 and a top layer 121. As seen in FIGS. 10-11, the ring 12, 14 can have a non-compressible bottom layer 122 and a compressible, thermally or electrostatically compressible layer 121. The top layer 121 can be configured of a compressible material while the base layer 122 can be configured of a non-compressible material and the strips 16 can be captured between them. In some examples, the top layer or the top and base layers can be made from a heat shrink material. In some embodiments, the ring 12, 14 can be formed from lengths of materials that are wound around themselves to form a layer of ring.

The rings can be made of a layer of composite materials where the base layer 122 is less compressible or elastic than the top layer 121. Energy can be added to the top layer 121 to produce a reduction in the top layer's diameter until the top layer compresses and captures the strips between the base layer 122. For example, the top layer 121 can be a heat shrink material. In this way, the top layer 121, base layer 122 and strips 16 can form a cage 10 as seen in FIGS. 10 and 11. In some embodiments, the strips can be attached to the balloon and/or balloon catheter with the rings that are made of a single layer of heat shrink material positioned over the strips similar to just the top layer.

The strips or rings can include indentations to facilitate attachment to the other. The strip 16 can include an indentation 171 on either side of the strip 16 (as illustrated in FIG. 10) or an indentation 171 on one surface of the strip 16 that can form a groove (as illustrated in FIG. 11). Though in FIG. 11, the top layer 121 is shown as a heat shrink material, it will be understood that in other embodiments a rigid ring could be press fit into the indentation 171. Such a rigid ring could be part of a single or multiple layer ring, thus there may or may not be a corresponding base layer 122.

Figure 12:
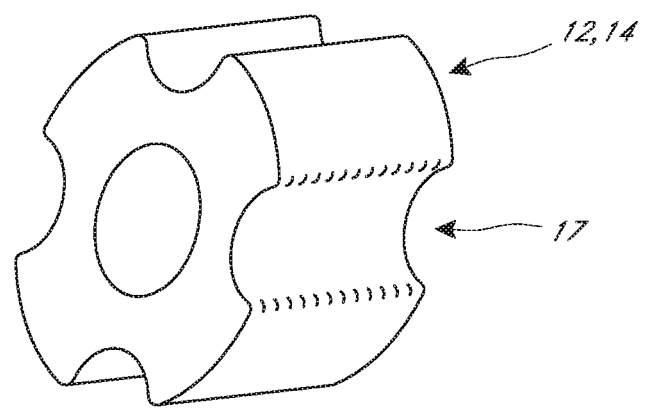
FIG. 12 is a perspective view of a ring.

FIG. 12, illustrates another embodiment of the ring 12, 14. Here, the ring 12, 14 can include a plurality of indentations or grooves 17. The grooves 17 can have a width that can accommodate the width of the distal end of strip 16. An end of a strip can be attached to the ring 12, 14 in the grooves 17 through the use of adhesive, mechanical coupling, wrapping heat shrink material around the ring, etc. In some embodiments, the strip 16 of FIG. 11 can be placed in the ring 12, 14 of FIG. 12 so that the indentations are engaged with each other.

Figure 13A:
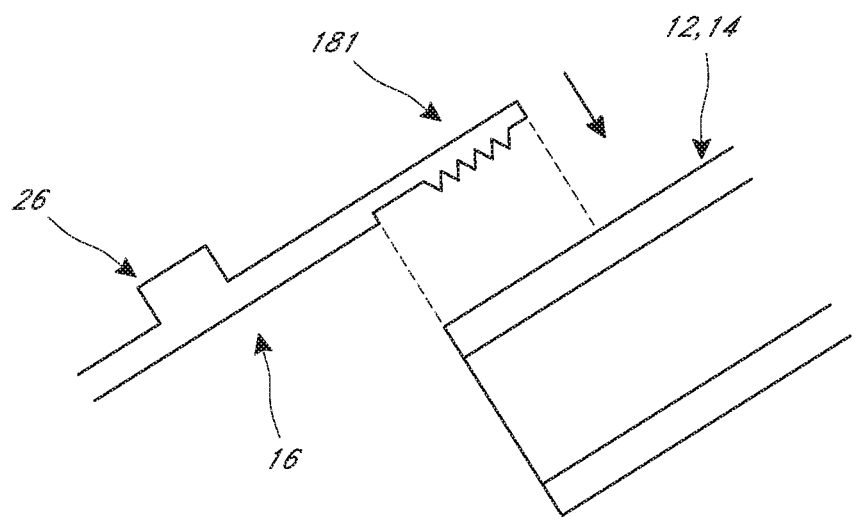
FIG. 13A shows a strip with a hook feature and ring.
Figure 13B:
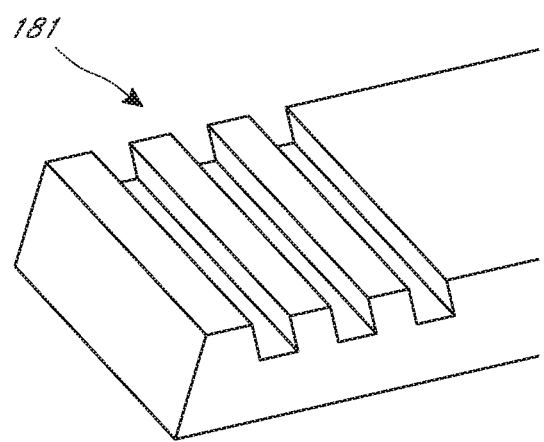
FIG. 13B is an end view of strip with a ridged hook feature.
Figure 13C:
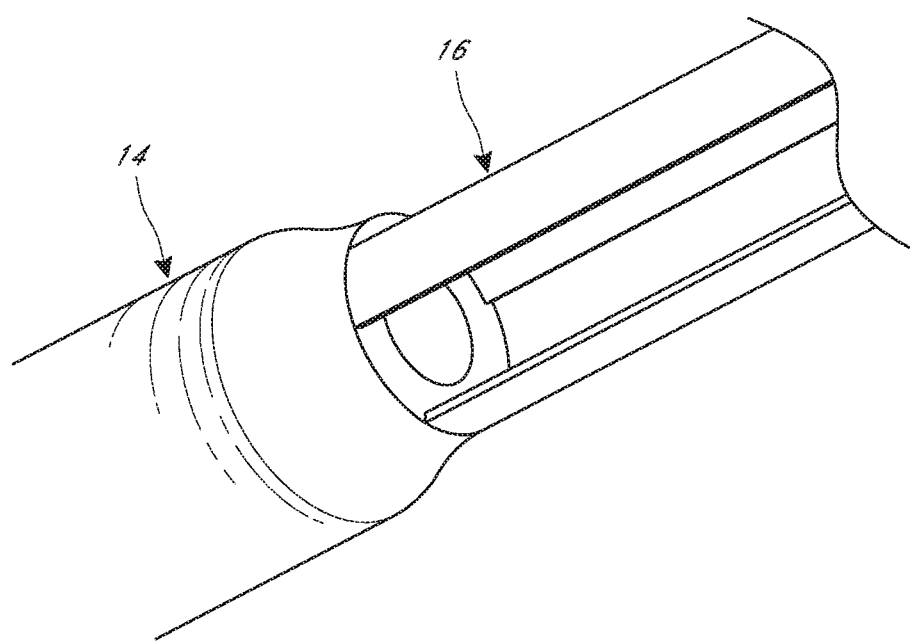
FIG. 13C shows a perspective view of a portion of a cage.

FIGS. 13A-C illustrate examples of a strip 16 that includes an securement feature 181 that improves the hold of the strips 16 to the rings 12, 14. In some variants, the securement feature 181 forms a section of the strip 16 with a higher surface roughness. This can be in the form of illustrated ridges or other teeth-like elements that aid in the imbedding of the strip 16 into or holding the strip on the ring.

When the ring 12, 14 is a polymeric material, the securement feature 181 can be formed as narrow sections of the strip 16 at the ends (as illustrated in FIG. 13A-B), or placed strategically along the strip length (such as where three or more rings are used). The securement feature 181 can be aligned with the rings 12, 14. During fabrication, the securement feature 181 can be pressed into the polymeric material as illustrated in FIG. 13A at a high temperature where the polymeric material is near or greater than the glass transition temperature of the material. In so doing the securement feature 181 can be used to engage or connect the strips 16 to the rings 12, 14 as illustrated in FIG. 13C.

In FIG. 13A the ring 12, 14 is shown to incorporate the securement feature 181 into the body of the ring material. FIG. 13A shows the strip 16 with a ridged hook feature 181 before it is pressed into the ring material. FIG. 13B shows a perspective view of another embodiment of securement feature 181. In some examples, the securement feature 181 can be significantly longer than the ring 12, 14 is wide and be designed to provide tension on the cage 10.

When the ring 12, 14 is made from an elastic material, such as rubber or polymer, or metallic alloy or a design with elastic properties like a spring, the ring 12, 14 can be used to provide tension on the cage 10 to enable the cage 10 to return to the relaxed, deflated balloon 20 position. Furthermore, the portion of the strips 16 without a wedge dissector is the thinnest and the most flexible. This can allow the strip 16 to be the most flexible at the edge of the balloon 20 where the forces are the highest.

Figure 13D:
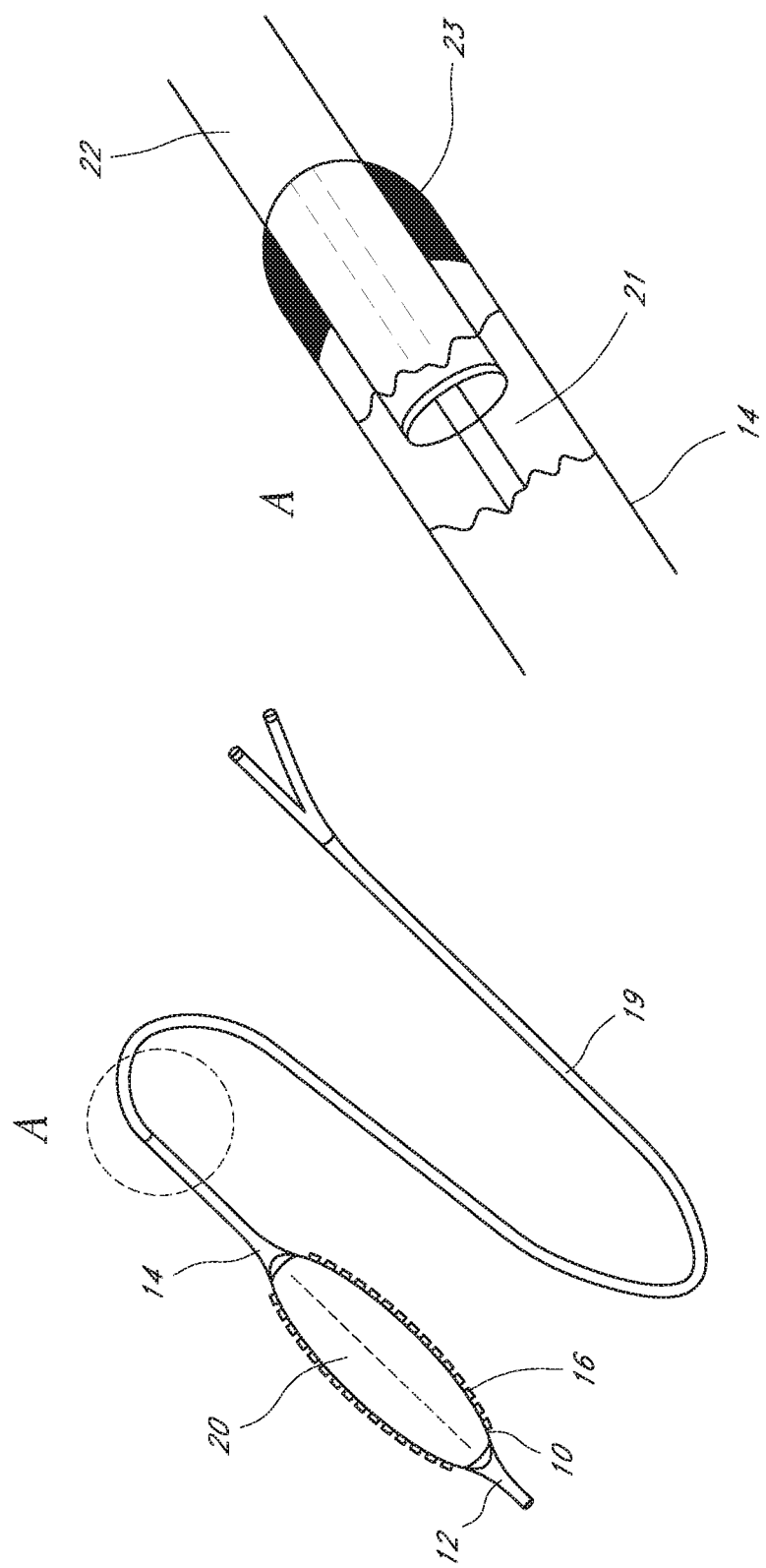
FIG. 13D illustrates a view of a conical distal ring retaining a plurality of strips.
Figure 13E:
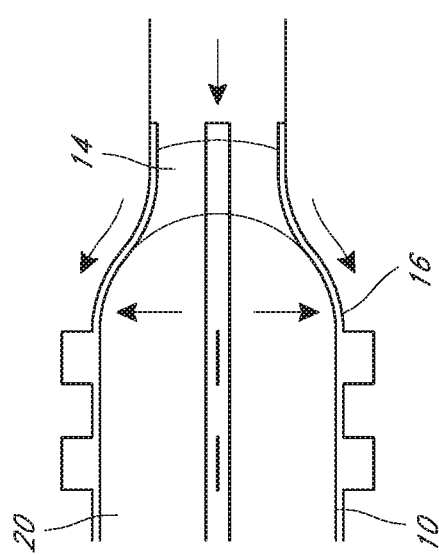
FIGS. 13E-F show a view of one end of a balloon with a cage disposed about the balloon and the forces applied to the balloon during inflation and deflation.
Figure 13F:
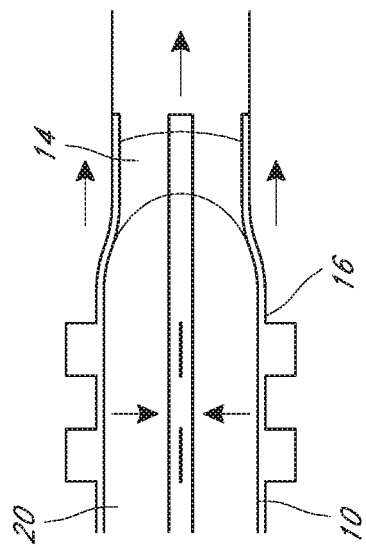

FIGS. 13D-F illustrate an example where the elastic material of a ring can provide tension on a cage during expansion and to then assist in deflating the balloon as the tension is released. Turning first to FIG. 13D, the cage 10 is disposed about the balloon 20. The cage 10 can be composed of a plurality of strips 16 that are secured to the balloon by rings 12, 14. In some examples, the rings 12, 14 can be made from long elastic material that can aid in pulling the strips 16 down into a linear position such that the wedge dissectors are perpendicular to the surface of the balloon 20. Callout "A" provides a schematic, see-through view of the proximal end of ring 14. As shown, ring 14 is secured about the outer catheter shaft 22 by an adhesive 23. As well, an inner guidewire shaft 21 can run concentric to the balloon 20. The guidewire shaft 21 can be secured with relationship to the catheter shaft 22. For example, the guidewire shaft 21 and the catheter shaft 22 can both be connected to different ports on a hub, such as the illustrated bifurcated luer at the proximal end of the balloon catheter. The balloon can be inflated by injecting a fluid into the catheter shaft. It will be understood that in some embodiments the catheter shaft 22 open directly inside the balloon 20, rather than opening at the ring 14 as shown. The ring can be attached to the catheter shaft 22 and/or the balloon 20.

FIGS. 13E-F illustrate a balloon 20 and cage 10 as the balloon 20 is inflated and subsequently deflated. As noted above, in some examples, the elastic material of the rings 12, 14 can stretch to allow the cage 10 to expand as the balloon 20 is inflated. In some embodiments such as the shown in FIGS. 13E-F, the rings can be made of an elastic polymer and the strips can be made of metal or an inelastic polymer. As shown in FIG. 13E, as the balloon 20 is inflated, the strips 16 of the cage 10 begin to move apart. In order to push each of the strips 16 outward, force is exerted radially outwards (as illustrated by the arrows) on the balloon 20—and by extension the cage 10—as the balloon 20 is inflated. As the balloon 20 expands, the rings 12, 14 are under tension and able to stretch enough to allow the strips 16 to maintain alignment while expanding with the balloon 20.

This tension can also help the balloon 20 to deflate. During balloon deflation, as illustrated in FIG. 13F, the tension on the strips 16 exerts a force radially inward as the strips 16 and the rings 12, 14 tend to want to return to a relaxed state. This force pulls on the strips 16 and allowing them to flatten, thereby providing a narrowed profile for catheter retraction.

Figure 14A:
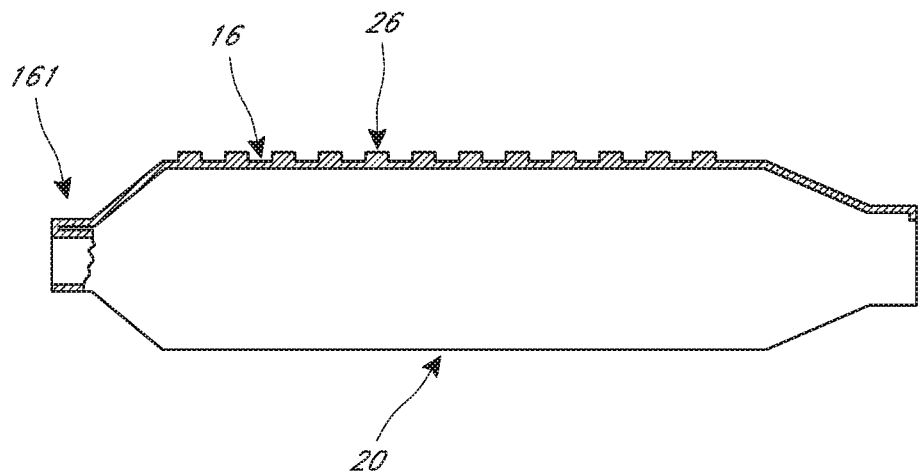
FIG. 14A illustrates a side view of an embodiment of a cage having strips with hooks that can attach to the inside of a balloon neck.
Figure 14B:
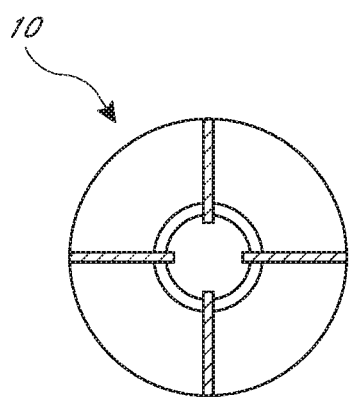
FIG. 14B shows an end view of a cage attached to a balloon as illustrated in FIG. 14A.

Looking now to FIGS. 14A-D another embodiment of strip 16 is shown with various types of rings. As illustrated in FIGS. 14A-B, in some examples, the ring can be fabricated from the lip on the neck of the balloon 20 and the portion of the catheter body used to bond the catheter to the balloon 20. The catheter can provide a pathway for gas or liquid inflation of the balloon 20. Additional components such as an over mold or heat shrink can be added to the bond joint, as can additive glue or polymeric material. In some examples, this can serve to prevent pressure from leaking out of the balloon 20 along the length of the strips 16 forming the cage 10.

As illustrated in FIGS. 14A-D, a hook 161 at the strip end can enable the strip to be easily aligned along the balloon surface and can aid in orienting the strip in a longitudinal orientation relative to the axis of the balloon 20. The hook 161 can be integrated into each end of the strip 16. The hook 161 can be wrapped around the lip of the neck of the balloon 20 from the outer diameter ("OD") of the balloon 20 neck around the opening and into the neck where the end of the hook 161 rests within the inner diameter ("ID") of the balloon 20 neck.

Both ends of the strip 16 can have a hook 161, or just one end can have the hook. In addition, the ends can be attached to the balloon catheter in the same or in different ways. For example, heat shrink can be wrapped around the ends of the strips and balloon. In some embodiment, heat shrink is wrapped around one end and a rigid ring, such as those discussed with respect to FIGS. 8-12 can be used at the other end, which may also include a heat shrink layer.

The strip may or may not be attached to the balloon at other locations. As shown, the strip 16 can also have hinges or pre-bent regions that correspond with the shape of the balloon. Thus, the strip in the expanded state can have a main portion having wedge dissectors 26 that is parallel with the axis of the balloon. Angled sections can extend from the main portion to the hooks 161. The angled sections can form an angle when the balloon is expanded as shown, but can be flat when the balloon is deflated. In some embodiments, hinges between the sections can be formed with thinner sections of material.

As shown in FIG. 14A the strip can attach to the balloon without a separate ring by use of the hooks 161. The balloon can be glued to a catheter (for example an elongated tube with one or more lumen) which can also secure the hook in place. FIG. 14A shows one strip for simplicity, though it will be understood that 2, 3, 4 (FIG. 14B), 5, or more strips could be used.

Figure 14C:
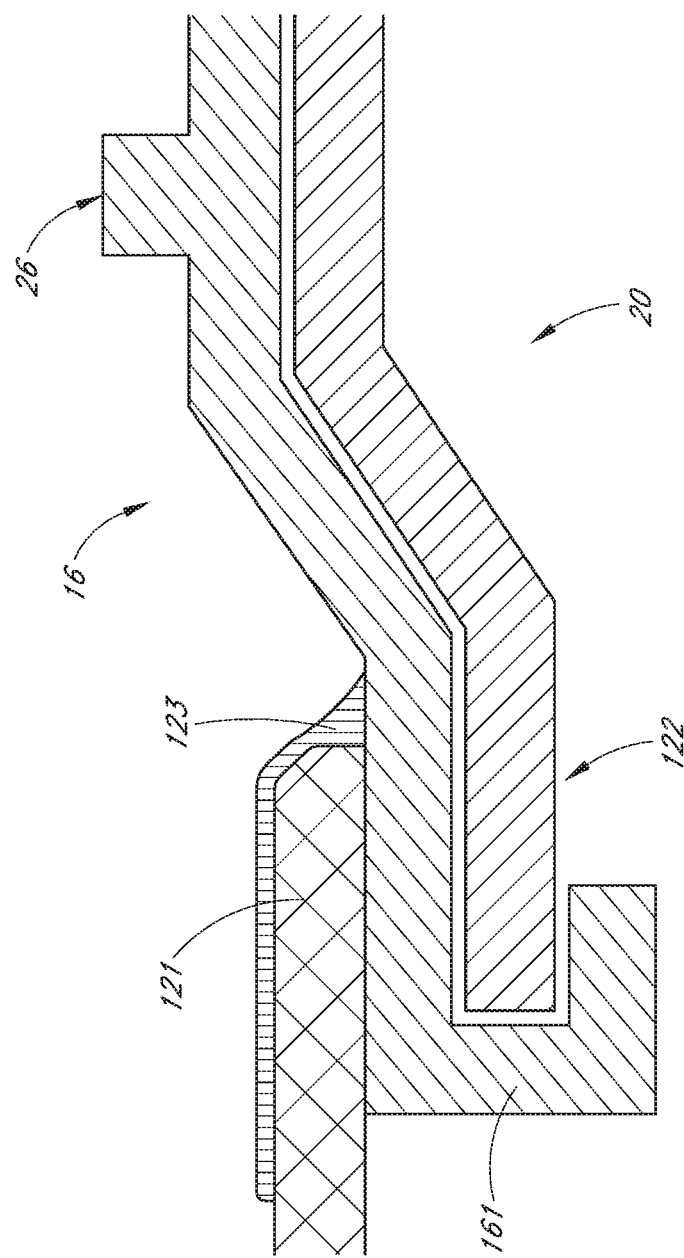
FIG. 14C is a cross sectional schematic view of the strip with hook locked into the balloon neck.

FIG. 14C shows a detail view of the hook 161 attaching to a balloon 20. As can be seen the balloon can serve as a base layer 122 of the ring and a top layer 122 is also shown. Adhesive 123 is also shown securing the top layer 121 to the balloon. In some embodiments, the top layer 121 can be the tube of the catheter.

Figure 14D:
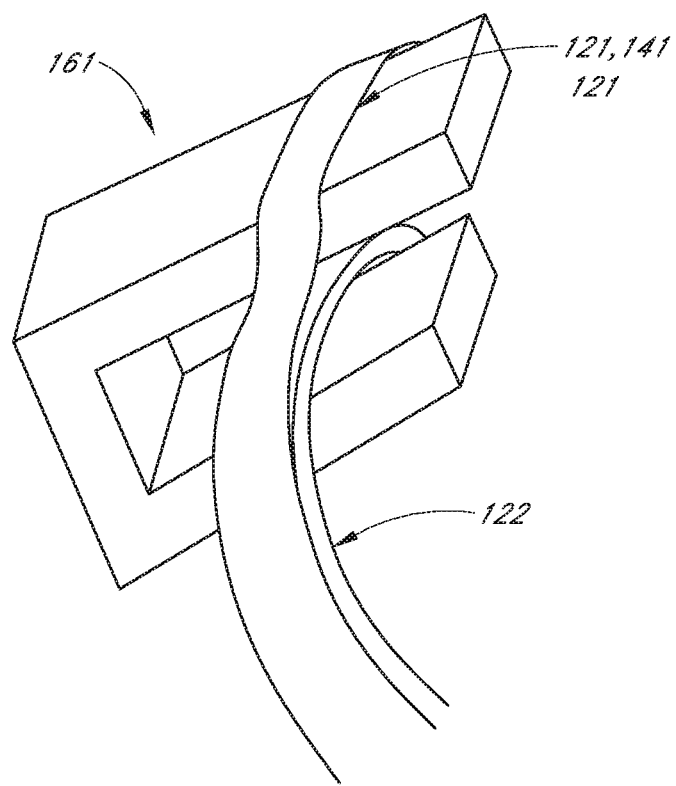
FIG. 14D is an alternative embodiment of the end of a strip with a multi-layer ring to form an end of the cage.

FIG. 14D shows a two layer 121, 122 ring. The two-layer ring can include two layers of heat shrink material. As discussed for FIGS. 10-11, the ring illustrated in FIG. 14D can be a multi-layer ring where the base layer 122 is less compressible or elastic than the top layer 121 and where energy is added to the top layer producing a reduction in the top layer's diameter until the top layer compresses and captures the strips between the base layer 122 and the top layer 121 to produce the cage 10.

Figure 14E:
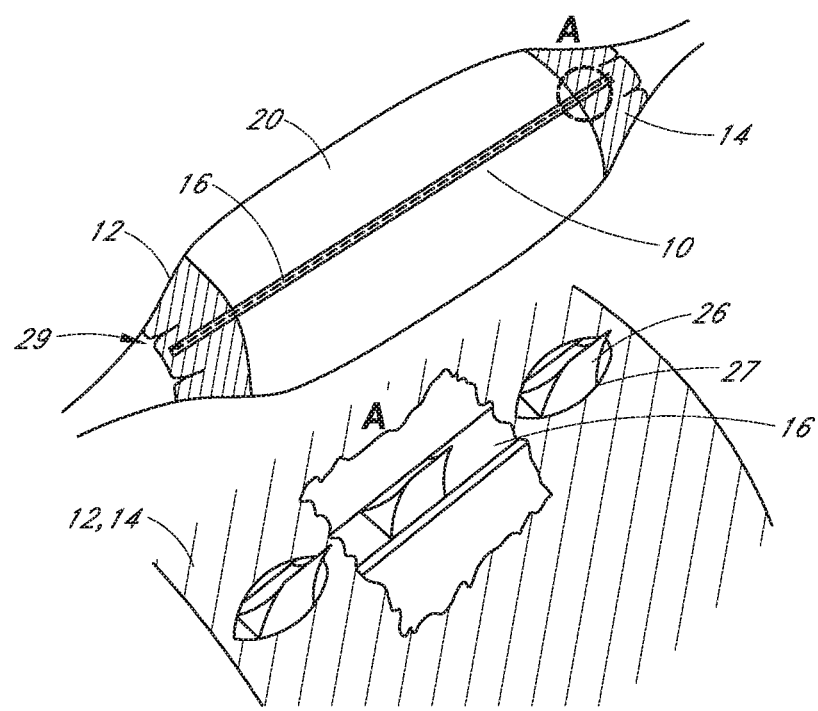
FIG. 14E shows an embodiment of a strip retained by a plurality of rings with the wedge dissectors protruding from the plurality of rings.

FIG. 14E illustrates another embodiment of the rings 12, 14 that secure the strips 16 on the surface of the balloon 20. As shown in callout "A," the rings 12, 14 can be secured to the balloon 20 such that the wedge dissectors protrude through the surface of the rings 12, 14. Callout "A" includes a cut away of the ring 12, 14 in the center in order to show the strip 16 below. The wedge dissectors can protrude through the rings 12, 14 in a variety of ways. For example, the shape of the wedge dissector can cut through the material of the rings 12, 14 as the rings 12, 14 are secured to the strips 16. This can form a hole 27. The rings 12, 14 can also have a plurality of holes 27 pre-cut into the rings 12, 14 to allow the wedge dissectors to extend through.

It can also be seen that the rings 12, 14 can be shaped to correspond with the taper of the balloon 20. For example, cutouts 29 of material in the rings can help a ring made of heat shrink material to shrink to the shape of the balloon.

As discussed above, each of the strips 16 can extend between one or two rings, though additional rings can be used as needed. For example, three, four, five, six, seven, eight, nine, or ten, or more rings can be used, especially with longer balloons. As one example, an angioplasty balloon 20 having a length of 300 mm can be fitted with a cage 10 having two rings 12 and 14 at either end. In addition to the rings 12, 14, the cage 10 can include rings 13 or other similar controlling elements that can aid the strips 16 in maintaining alignment and orientation as the balloon 20 expands towards the artery wall.

Figure 15A:
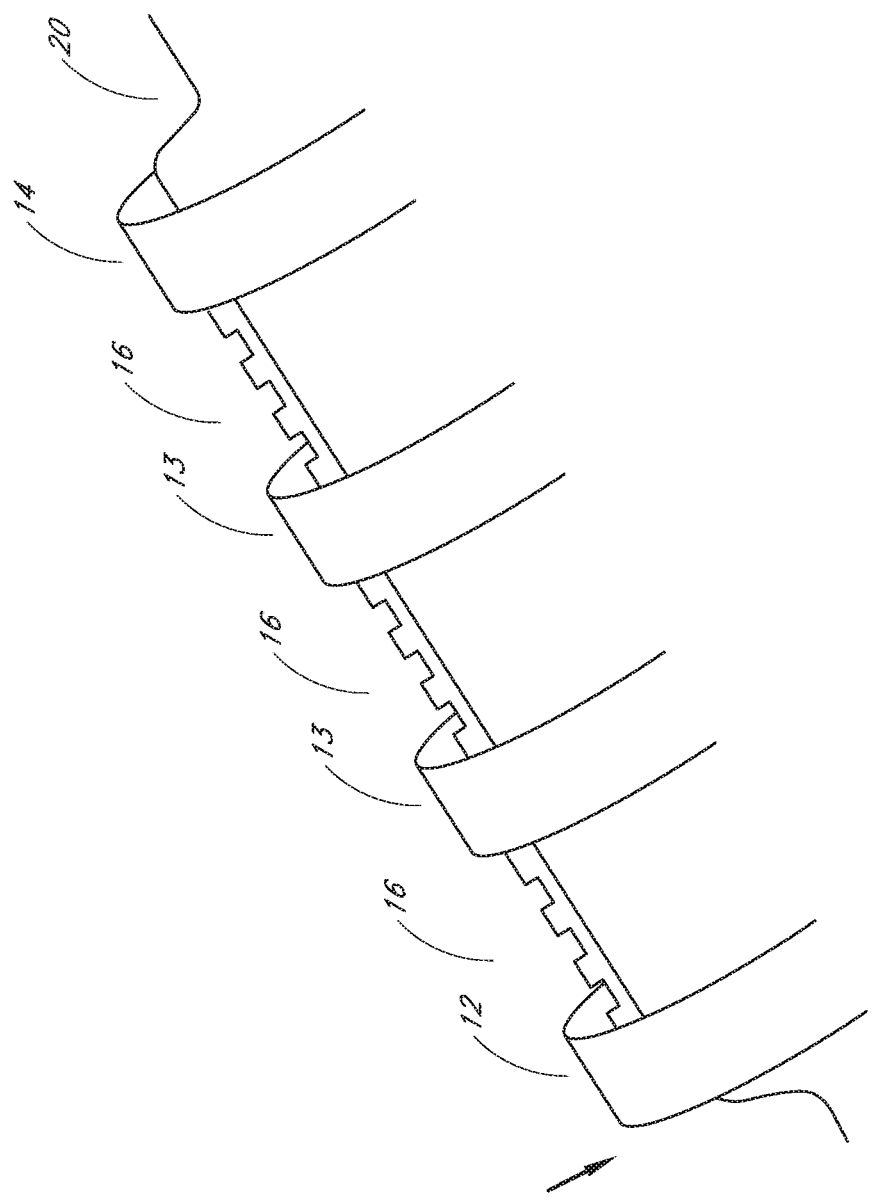
FIG. 15A illustrates a partial view of an embodiment of an angioplasty balloon with an embodiment of a strip bound to the angioplasty balloon with a plurality of ringed material to form a cage.

As illustrated in FIG. 15A, the rings 13 can be a fraction of the overall length of the balloon 20. Some ring 13 designs are less than one and a half times the length of the balloon 20. In other examples, the rings are between 1.0-0.5 times the balloon 20 length. More commonly the length of the rings 13 are between 2.5 and 1.5 times the balloon 20 diameter and typically between 1.5 and 0.5 times the balloon 20 diameter. Each ring 12, 13, 14 can be made from a different material so at to provide more than one advantage and function of the rings 12, 13, 14.

The rings 13 can be placed on the outer surface of the body of the balloon 20. In some examples, the rings 13 can be designed to retain the body of the strips 16 such that the position and orientation of the strips 16 are maintained. It can also be seen, that the strip 16 does not extend along the shoulders of the balloon. Thus, the strip can be elongated and can extend parallel with the axis of the balloon. FIG. 15A shows one strip 16 for simplicity, though it will be understood that 2, 3, 4, 5, or more strips could be used.

These rings 13 can be positioned over the expanded balloon 20 area and may have different properties than the rings 12, 14 on either end of the balloon 20. As illustrated in FIG. 15A, in some embodiments, the rings 13 positioned over the balloon 20 surface may be more elastic in property than those located on the ends of the balloon 20. This can allow the rings to accommodate the expansion and refolding of the balloon 20. In some examples, the rings used on the outer diameter of the balloon 20 are placed over the two ends of each separated strip. The strips 16 may also be glued, welded, restrained by friction fit, or otherwise attached to any of the rings described above.

In some embodiments, rows of strips and/or strip segments can be placed around the balloon 20. Some rows may extend over the entire length of the balloon 20 and other rows may not. In some examples, a row may include a plurality of strips in series that are separated by gaps. Placing strips in a series on the balloon can provide greater flexibility which can improve deliverability through tortuous anatomy.

As described previously, rings 12, 14, 13 can be used to retain the strip on the surface of the balloon 20. The rings can be connected to the strips in any number of different ways, as described in the various embodiments herein. In some embodiments, the ends of the strips 16 with no wedge dissectors can be used to attach to the rings. In other embodiments, the ends with wedge dissectors can attach to the rings.

Figure 15B:
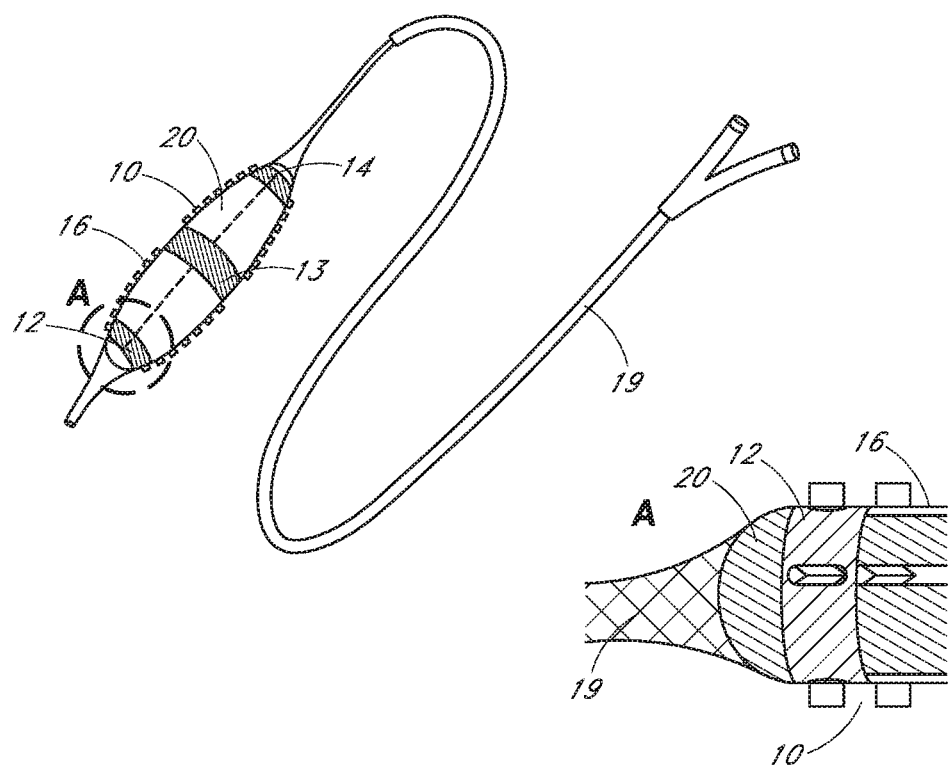
FIG. 15B is an angioplasty balloon with a cage having a plurality of segmented strips that are bound to the surface of the balloon by a plurality of rings.

FIG. 15B illustrates another embodiment of balloon catheter. A balloon 20 is shown with a cage 10 with four equally spaced rows of strips 16. Each row has two strips 16 that are laid in series. A ring 13 attaches the adjacent strips 16 to properly secure and orient the strips 16 across the surface of the balloon 20. Rings 12, 14 hold down the other ends of the strips.

The callout "A" provides an enlarged view of the distal end of the balloon 20 with cage 10. The hatching illustrated in callout "A" is provided to help visualize and delineate the different parts of the device. As shown, the end of the balloon 20 includes a ring 12 that secures a plurality of strips 16 to the surface of the balloon 20. The balloon 20 is disposed about a catheter 19. The ring 12 can be a heat shrink material. A wedge dissector is also shown extending through the ring. The placement of the strips is further clarified in FIG. 15C which shows how a pair of strips 16 which are laid in series such that the strips 16 span the length of the balloon 20.

Figure 15C:
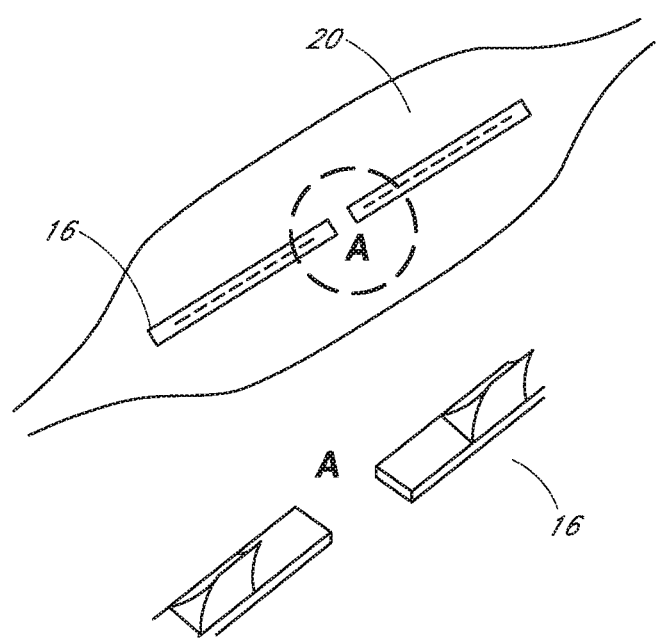
FIG. 15C shows an example of the placement of the segmented strips on the surface of the balloon.
Figure 15D:
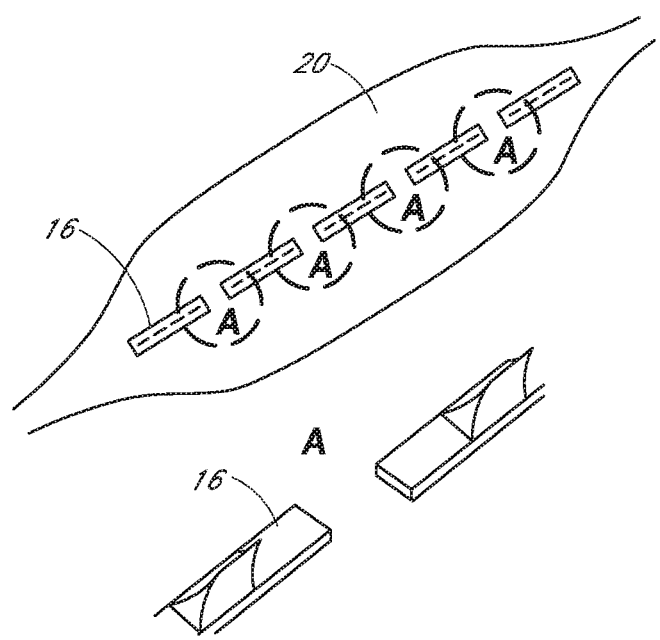
FIG. 15D is another example of the placement of a plurality of segmented strips onto the surface of an angioplasty balloon.
Figure 15E:
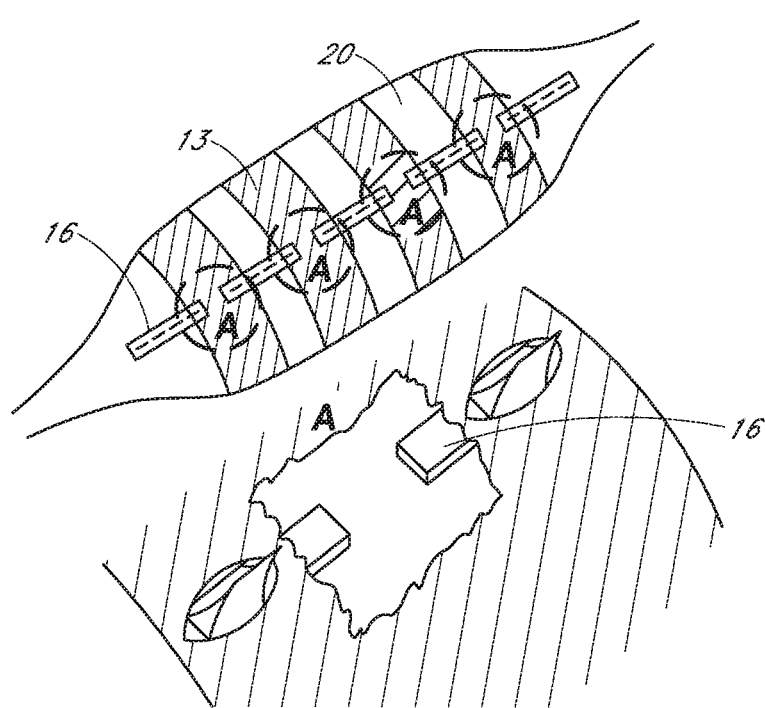
FIG. 15E illustrates an example of a plurality of segmented strips bound to the surface of a balloon by a plurality of rings.

To improve flexibility, the cage 10 can have rows that are made up of a greater number of strips 16 than illustrated in FIGS. 15B and 15C. FIGS. 15D-15E illustrate an example where five strips 16 are laid across the surface of the balloon 20 in series. As noted previously, each of these strips 16 can be secured on the surface of the balloon 20 by a plurality of rings 13. Callout "A" provides a cut away of the ring 13 to show the gap between the two strips 16 that are in series. As described above with reference to FIG. 14E, the wedge dissector can protrude through the ring 13 in a variety of ways. For example, the shape of the wedge dissector can cause the wedge dissector to poke through the material of the ring 13. As well, the ring 13 can have a plurality of holes cut into the rings 13 to allow the wedge dissectors to poke through.

In addition to having multiple strips in rows, the gap between the strips in a row can also be adjusted to increase flexibility. To ease manufacturing the linear alignment in the theta direction around the radius (angle drift) and the spacing alignment between the strips 16 (gap) can have a relatively broad tolerance creating greater options in developing the manufacturing process and choosing tools. In some cases, the gap tolerance can be ±5 mm and the angle drift ±25 degrees; ±3 mm and the angle drift ±10 degrees; and ±2 mm and the angle drift ±5 degrees. Cage designs that require greater tortuosity can utilize the periodic strip placements in a linear sequence with spaced apart strips. This can enable the balloon to manage bends and turns in anatomical spaces with less stress on the strips and more effective pushability of the entire system.

As shown herein many of the strips 16 have a flat bottom. This can help the strips 16 sit on the surface of the balloon and to maintain the orientation of the wedge dissectors. This can prevent rotational movement of the strips 16 on the surface of the balloon 20.

Three unique features that all strip and ring configurations can work to achieve are 1) perpendicularity of the wedge dissectors to the balloon surface, 2) maintaining flat and low profile of the strips on the balloon, aiding in limiting the wedge dissectors from damaging tissue on its journey, and 3) either assisting in deflation of the balloon or producing a minimal burden on the typical balloon deflation characteristics. To achieve these features strips typically have a flat bottom, are bounding to the balloon with rings on either end of the strip, are folded to limit wedge dissector interaction with tissue on its journey, and when a ring lays over the wedge dissectors the wedge dissectors poke through the rings and the majority of the wedge dissector height is still available for penetration into the vessel. Although some designs utilize rings to produce forces on the balloon enabling more effective balloon deflation by either pulling on the strips end to end or by applying radial compression, in most designs the rings can support the strips by limiting strip movement, aiding in wedge dissector orientation, and preventing the strips from separating from the balloon. Design features that contribute to these functional characteristics include: strips that have flat bottoms enabling stable orientation of the wedge dissectors but are thin enough to be laid down tangential to the balloon or contained in a fold of the balloon during folding, spacing between the wedge dissectors does not have a cutting edge enabling rings to lay in the spacing and support strip retention, and the ends of the strips can be thinnest with no wedge dissectors enabling greater surface area for rings to bond to the strip and enabling the strip to be most flexible at the edge of the balloon where forces are highest during catheter migration to and from site of deployment. It will be understood that other benefits and advantages can also be provided.

The rings 12, 13, 14 can be attached to the strips 16 in a variety of ways. FIGS. 16A-C shows examples of the rings 12, 13, 14 secured to the strips 16. FIG. 16A shows a material wrapped around the balloon to form rings 12, 13, 14 such that the material of the ring can be secured to more than one strip. In some examples, as illustrated in FIG. 16B, the ring 12, 13, 14 can be wrapped about a portion of each strip. This can be accomplished in the same way as illustrated in FIG. 10, where each of the rings can have an upper layer and bottom layer that wraps around a portion of the strip 16. FIG. 16C illustrates a solid ring 12, 13, 14 that can be attached to a portion of the balloon. A portion of the strip can be secured to the ring.

As discussed herein, many of the embodiments can use a heat shrink material for part of, or the entire ring 12, 13, 14. Heat shrink material generally starts from an extruded tube that is cross-linked using a form of radiation. The tube can be stretched or otherwise formed to the desired thickness. For example, it can be stretched to a flexible microscopically-thin-wall tubing, it can be made rigid from a heavy-wall tubing, or it can be somewhere in-between. Cross-linking can create a diameter memory and can be designed with a shrink ratio from 2:1 up to 10:1. Heat shrink typically shrinks only in the radial direction but can also shrink in length.

Heat shrink material can be manufactured from a thermoplastic material, such as polyolefin, fluoropolymer (including fluorinated ethylene-propylene (FEP), polytetrafluoroethylene (PTFE) or polyvinylidene fluoride (PVDF)(e.g. KYNAR)), polyvinyl chloride (PVC), neoprene, silicone, elastomer or synthetic rubber and fluoropolymer elastomer (e.g. VITON). When a flexible material is desired, such as one that expands with a balloon, the heat shrink material can include one or more of polyolefin, silicone, elastomer or VITON (synthetic rubber and fluoropolymer elastomer).

Heat shrink material in the form of a tube can be used to slide onto or over the strips 16. The tube can have a shrink ratio of 3:1 or higher (e.g. 3.5:1, 4:1, 4.5:1, 5:1, 6:1) and allow for gentle heat shrinking to prevent any balloon deformation or other changing of the balloon's properties. The material can be flexible enough to conform to the balloon through a range of balloon diameters (such as typical with semi-compliant balloon technology ~0.5 mm diameter range), and may have an adhesive or other coating to support the bonding of the heat shrink material and balloon. The heat shrink material can be a thin film. The heat shrink material may also be in the form of a sheet or multiple sheets instead of a tube.

A method of retrofitting a balloon catheter with a cage can include any of the following steps. Positioning strips around an inflated balloon. The strips may include wedge dissectors. The strips can be positioned equally spaced around the inflated balloon. The strips can extend primarily longitudinally. The strips may be positioned serially in rows, such as 2-6 rows, each with 2-6 strips. The strips can be attached either permanently or temporarily to the balloon with an adhesive. Heat shrink material can be positioned around the ends of the strips as a ring. Individual rings of heat shrink material can connect to or cover ends of multiple strips positioned circumferentially around the balloon. Individual rings of heat shrink material can also connect to or cover ends of adjacent strips positioned serially in a row. Heat can then be applied to shrink the heat shrink material. The balloon can be deflated and then sterilized in preparation for use.

Figure 17:
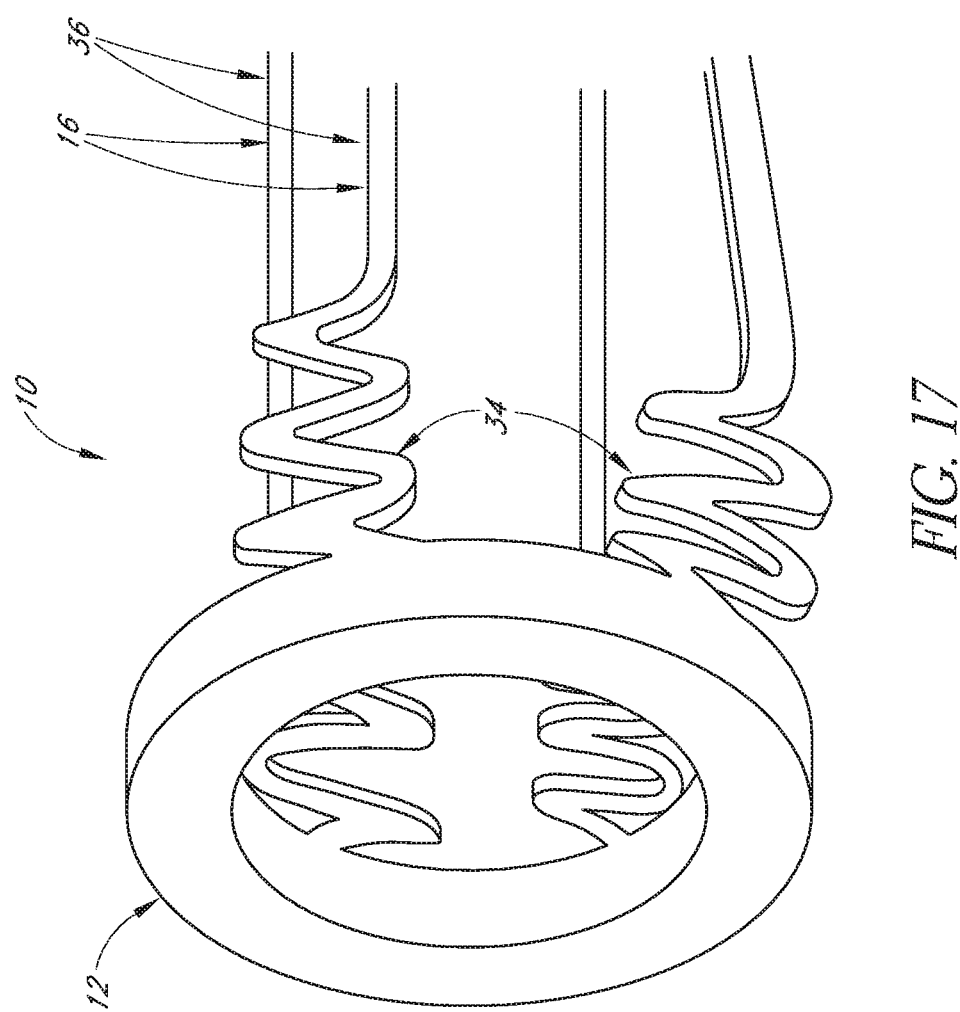
FIG. 17 illustrates a schematic view showing a detail of an embodiment of a cage with a spring.

Turning now to FIG. 17, a schematic view is illustrated showing a detail of a cage 10. In some embodiments, the strip 16 is shown having a section 34 composed of a spring zone. The spring section of the strip 16 can provide a plurality of benefits. For example, the spring section 34 can increase the flexibility of the cage 10. Increasing the flexibility of the cage 10 can allow the cage 10 to more easily pass through the tortuous geometry of a blood vessel. The spring section 34 can also provide a wider base for the wedge dissectors 26, to help the wedge dissectors 26 remain in the desired orientation.

In some embodiments, the spring section 34 can interface with a surface of the balloon 20. The spring section can help the strip 16 to remain in the correct position with the wedge dissectors 26 in an outwardly projecting orientation. In some examples, the spring section can counteract a sideways bending moment on the spike such that the wedge dissectors 26 do not bend, flex, or change position an undesirable amount. In some embodiments, the spring section 34 can also provide the benefit of assisting the balloon 20 in refolding post inflation. The spring can add mechanical tension on the balloon 20 to return it to a compressed state and further aid the rings in compressing the balloon 20 during deflation cycles.

Figure 18:
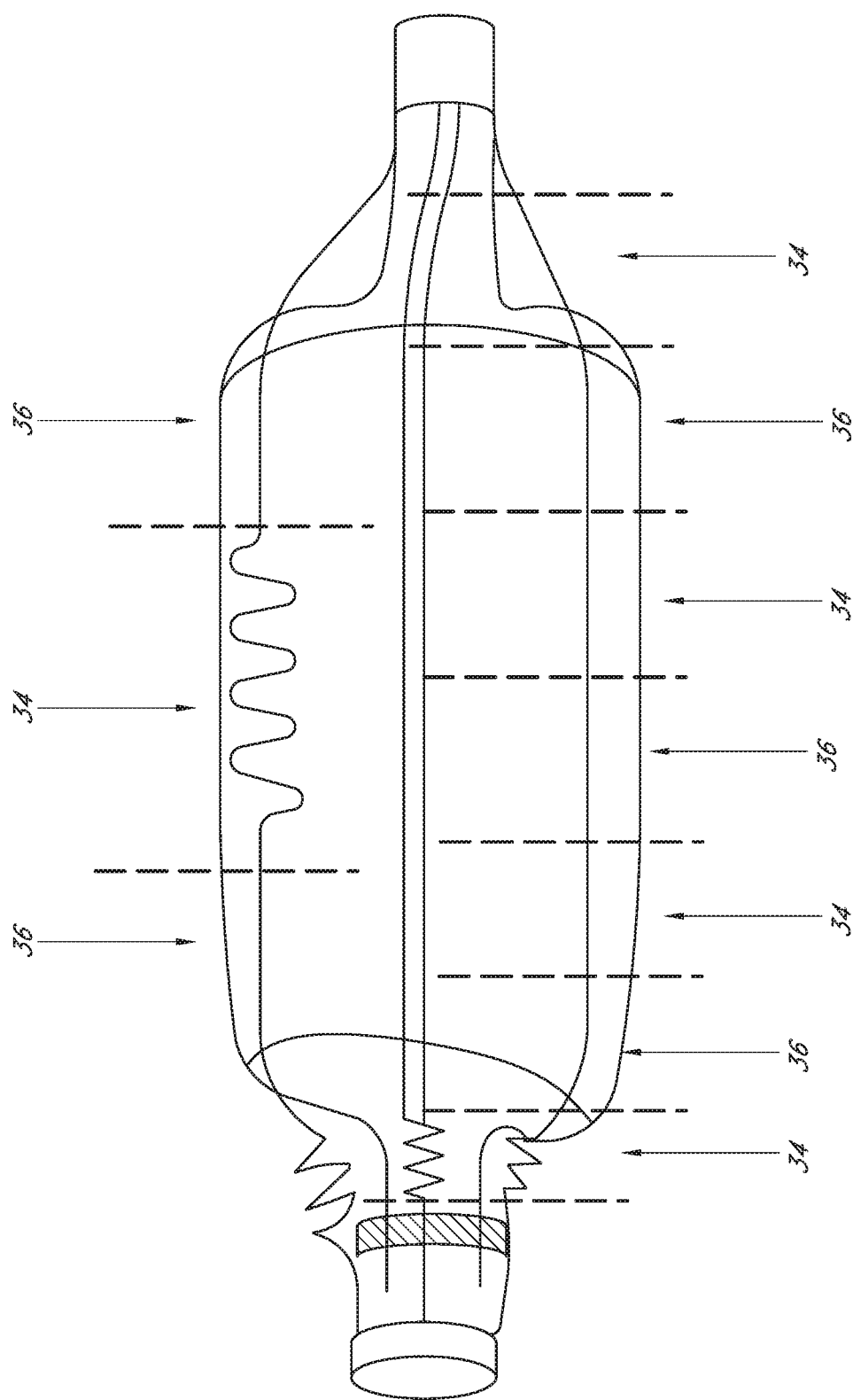
FIG. 18 illustrates various an embodiments of a cage utilizing aspects of the spring detail of FIG. 18.

The spring section 34 can have an undulating configuration and be connected to a straight section 36. In some examples, the wedge dissectors 26 can be located on the straight section. In other embodiments, the spring section can be sinusoidal. As illustrated in FIG. 18, the spring section is shown having a larger amplitude at the proximal end as compared to the distal end. The amplitude can decrease while the period increases along the spring section towards the straight section in a distal direction. In some embodiments, one side of the spring section can have a larger amplitude than the opposite side. In some embodiments, the spring section can be symmetrical.

Figure 19:
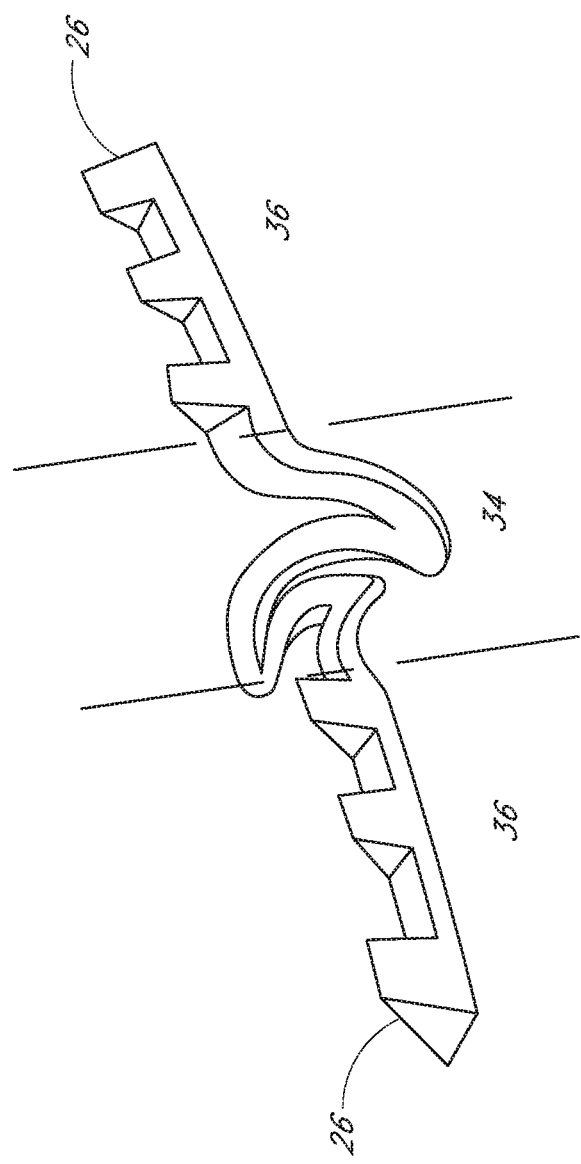
FIG. 19 shows a portion of a cage including a spring strip and spike configuration.

FIG. 18 illustrates various embodiments of the cage 10 utilizing the spring section 34 and straight section 36. Any number of different patterns can be used. FIG. 19 shows a detail of wedge dissectors 26 on straight sections 36.

Systems and methods as disclosed herein can deploy the cages and wedge dissectors in any body lumen, including vascular lumens such as arteries and veins. The arteries could be coronary arteries, peripheral arteries, or carotid or other cerebral arteries, for example, or iliac, femoral, superficial femoral, iliac, or other peripheral vasculature, for example. The device may also be used in any lumen or transportation vessel found in any of the respiratory, digestive, urinary, reproductive, lymphatic, auditory, optical, or endocrine systems. It is understood that a device for generating serrations in any one, two, or more of these systems may take slightly different forms. Independent of the location the device might be used, some embodiments of devices include spikes (also herein referred to as wedge dissectors, or serrating elements on a spline and an expandable mechanism to increase and decrease the diameter of the spike features (such as a balloon) with both attached to a base catheter-like device.

Figure 20:
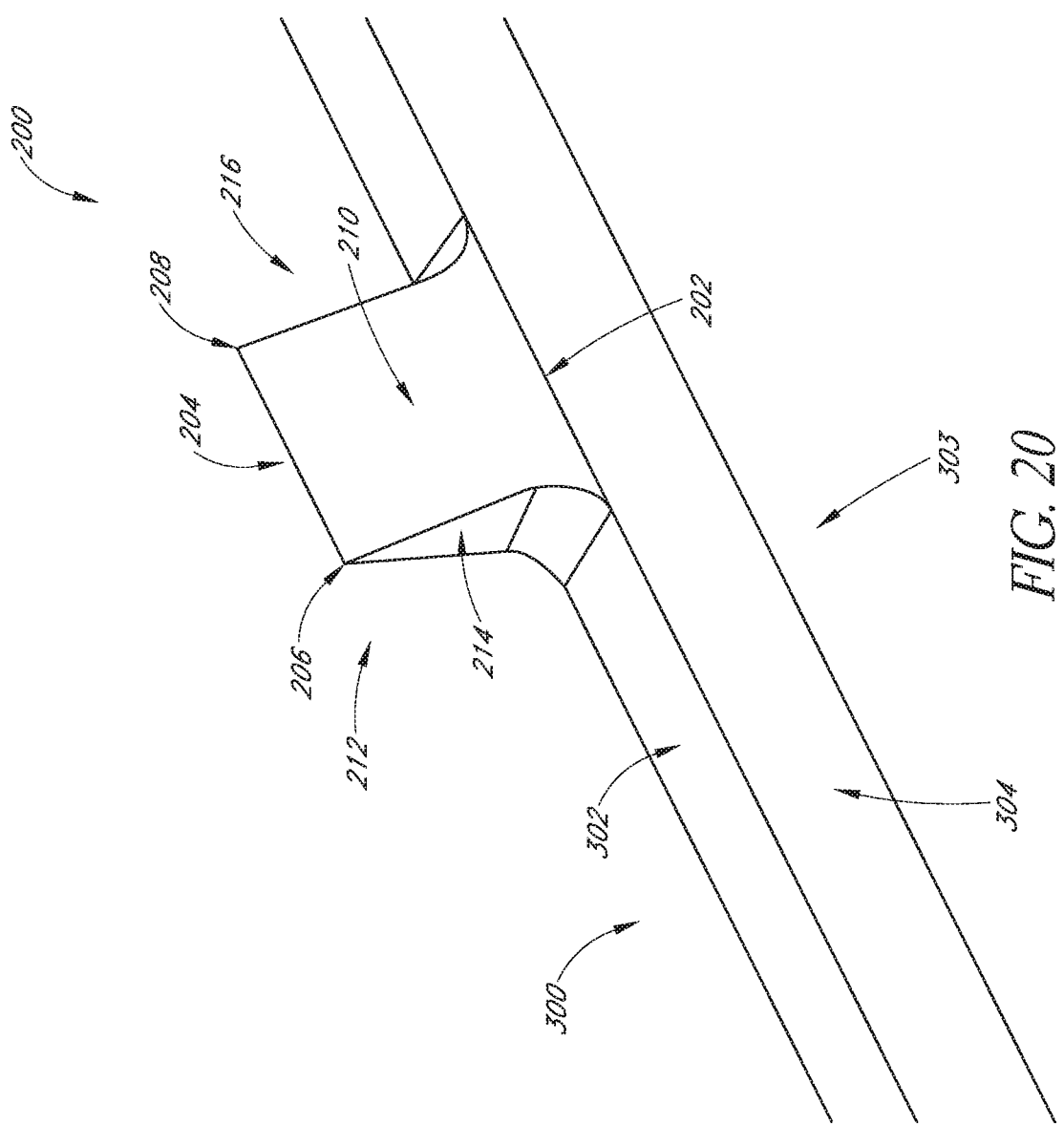
FIG. 20 is a close-up detail view of an embodiment of a wedge dissector on its associated strip.

In some embodiments, as illustrated for example in FIG. 20 which is a close-up detail view of an embodiment of a wedge dissector 200 on its associated strip 300, a wedge dissector 200 can include a strip-facing base surface 202 (which may also be referred to herein as a bounded surface). The strip-facing base surface 202 of the wedge dissector 200 can be defined by the base where the wedges 200 protrude outward and directly continuous with a surface of the strip at the interface between the wedge dissectors and the balloon. The strip could be a spline 300 or other strip-like structure. In some embodiments, this strip-facing base surface 202 has a relatively narrow width made of a hard material capable of holding a sharp edge. In some embodiments, the preferred material is martensitic stainless steel, with a hardness of 52 to 64 on the Rockwell C-scale (HRC) although other materials including a polymer or co-polymer including but not limited to polyolefin, fluoropolymer (including fluorinated ethylene-propylene (FEP), polytetrafluoroethylene (PTFE) or polyvinylidene fluoride (PVDF)(e.g. KYNAR)), polyvinyl chloride (PVC), neoprene, silicone, elastomer or synthetic rubber and fluoropolymer elastomer (e.g. VITON), or a combination thereof can be utilized. In some embodiments, the strip is about or no more than about 0.008", 0.010", or 0.012" wide (oriented circumferentially). In some cases, the width can be between about 0.006" and about 0.020" or between about 0.004" and about 0.030". In some embodiments, the strip 300 typically runs longitudinally the length of the working balloon edge, but can also be oriented in angles up to and including 90 degrees from the longitudinal axis of the balloon (or other expandable structure), or in a helical fashion at varying pitches. In some embodiments, the height of the base strip 300 can be between about 0.004" and about 0.010", or between about 0.002", and about 0.020" in some embodiments.

Still referring to FIG. 20, a wedge dissector 200 can also include a radially outwardly facing surface 204 (which may be referred to herein as an unbounded surface) that can define a top surface of the wedge dissector 200 from first (e.g., proximal) edge 206 to second (e.g., distal) edge 208 and be configured to contact tissue, plaques, or other structures within the body. Also shown are anterior surface 210, posterior surface 212, and opposing lateral surfaces 214 and 216. In some embodiments, the lateral surfaces 214, 216 extend upward generally perpendicular to the longitudinal axes of the strips, and the radially outward facing surface extends between the lateral surfaces as a linear, curved, or other geometry as described elsewhere herein at an angle to the lateral surface/lateral surface axis. Also illustrates are strips or splines 300 having an unbounded (e.g., superior-facing) surface 302 that can be coextensive with the strip-facing surface or boundary 202 of the wedge dissector 200, as well as side surfaces (e.g., 304), and inferior-facing surface 303.

Figure 21:
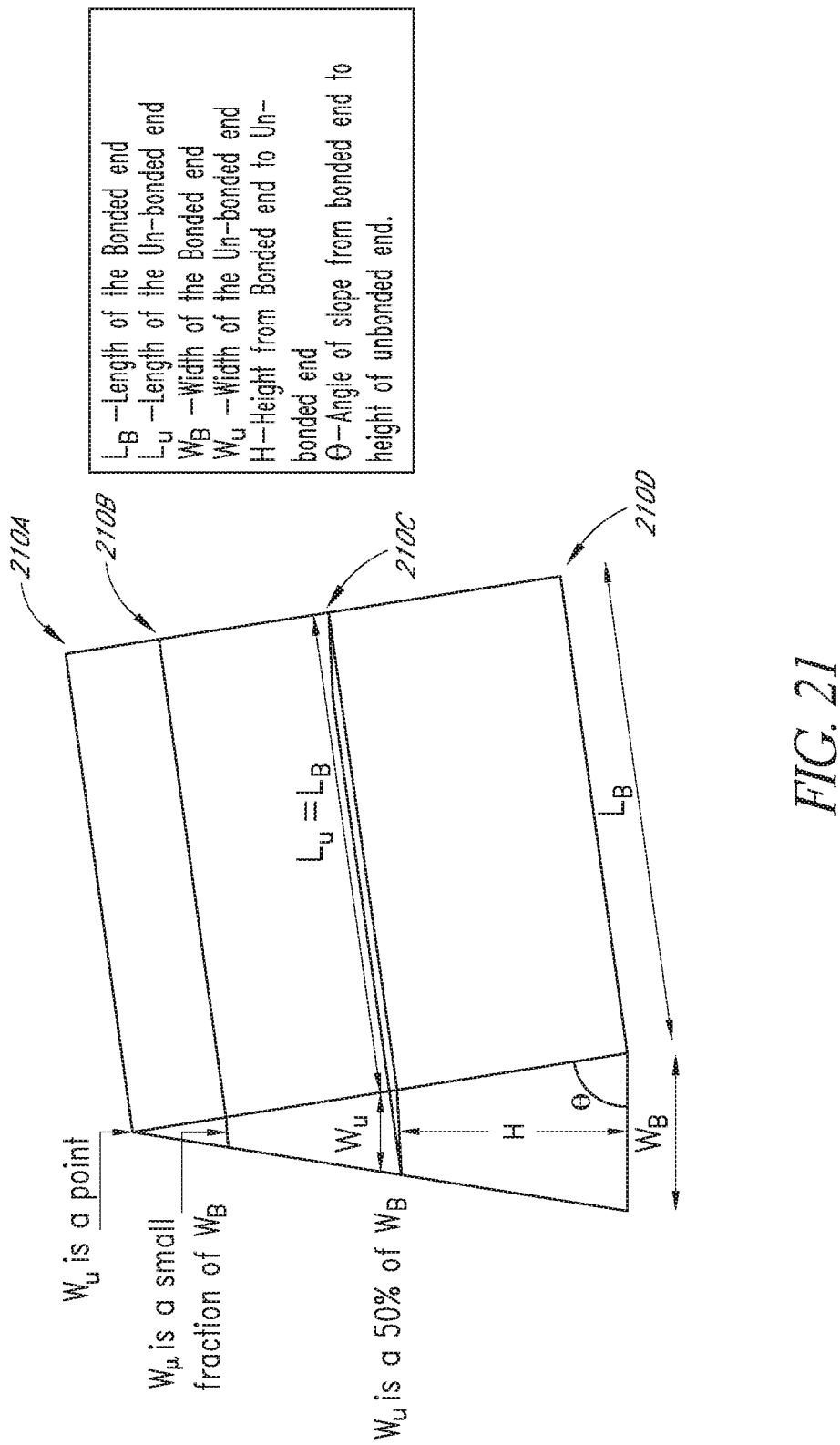
FIG. 21 illustrates a schematic perspective view of various dimensions and terminology of a wedge dissector, according to some embodiments.

FIG. 21 is a schematic illustrating several possible non-limiting embodiments of a wedge dissector. In some embodiments, the length of the radially outwardly facing surface $L_U$ (e.g., radially outwardly facing surface 204 between first edge 206 and second edge 208 of FIG. 20) is between about 30%, 20%, or 10% less than the total length of the strip-facing surface $L_B$ (of strip-facing surface 202 in FIG. 20). In some embodiments, the radially outwardly facing surface length $L_U$ can be from about 50% to about 20% less than the strip-facing surface length $L_B$, and sometimes as large as the strip-facing surface length $L_B$. The radially outwardly facing surface width $W_U$ is in some cases equal to or less than the strip-facing surface width $W_B$, and typically between or less than about 10%, 20%, 30%, 40%, or 50% of the strip-facing surface width $W_B$, or between about 20% and about to 50% less than the strip-facing surface width $W_B$, and sometimes about or up to about 50%, 60%, 70%, 75%, or 80% of the strip-facing surface width $W_B$. Therefore, in some embodiments there is an angle θ that is equal to or less than about 90 degrees that defines the slope from the strip-facing surface width $W_B$ to the radially outwardly facing surface width $W_U$ on at least one of the strip-facing surface width $W_B$ edges. While in some embodiments the radially outwardly facing surface width $W_U$ is constant from edge to edge, in some embodiments the radially outwardly facing surface width $W_U$ varies along the radially outwardly facing surface length $L_U$ as described elsewhere herein, such as decreasing from a first lateral edge to a point or segment in between the first lateral edge and the second lateral edge of the radially outwardly facing surface segment, and then increasing, from the point or segment in between the proximal edge and the distal edge, to the distal edge. In some embodiments, the relatively central segment in between the proximal edge and the distal edge has a constant width, while the lateral segments surrounding relatively central segment have variable, such as tapered widths.

Figure 22A:
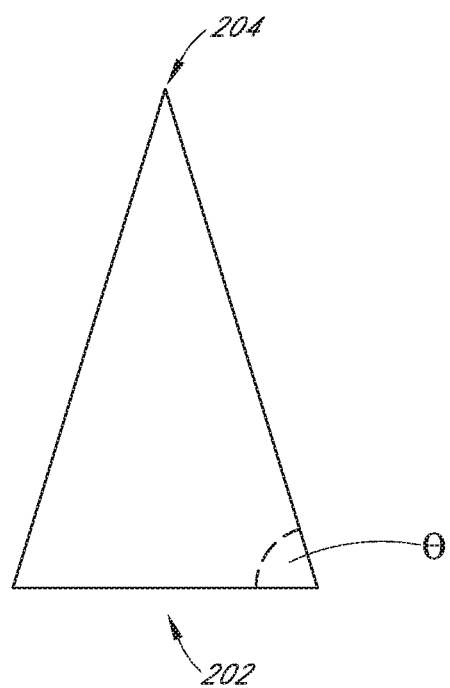
FIGS. 22A-22F illustrate respective end and isometric views of various wedge dissector geometries, according to some embodiments.
Figure 22B:
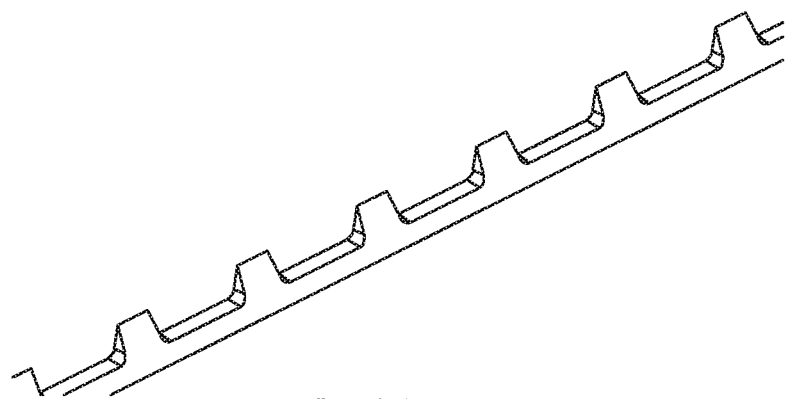
Figure 22C:
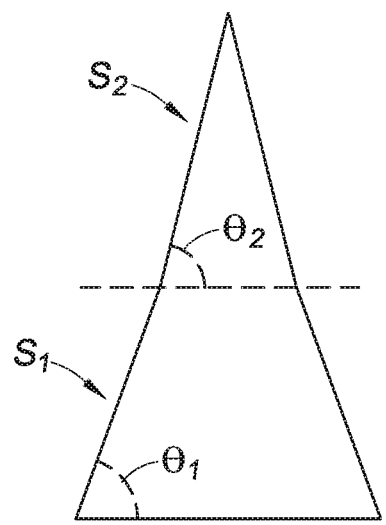
Figure 22D:
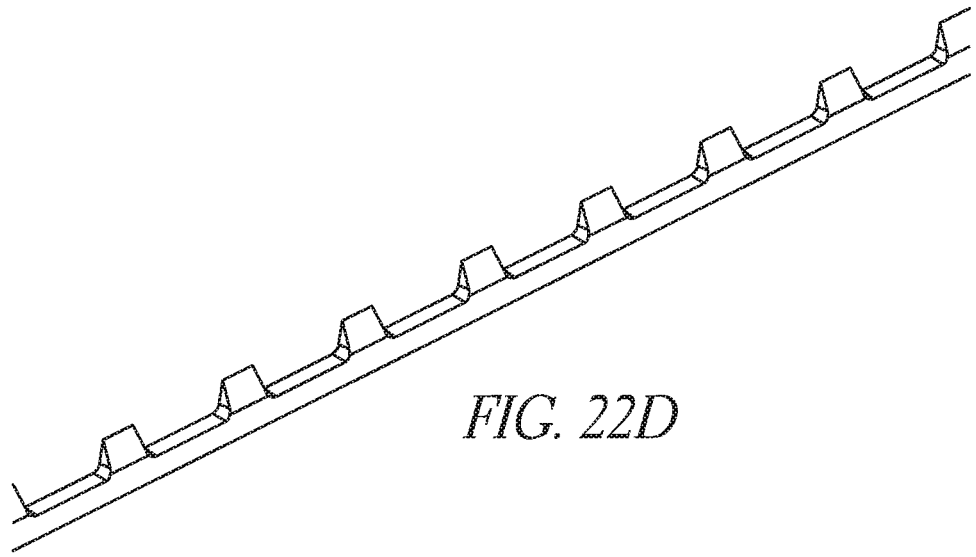
Figure 22E:
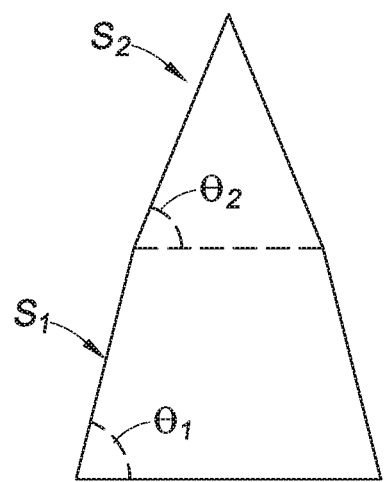
Figure 22F:
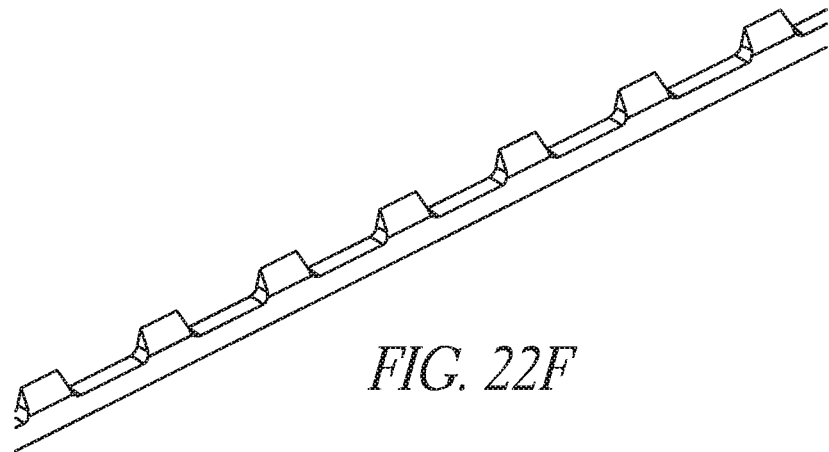

Although the radially outward facing width $W_U$ can come to a point, sloping from the strip-facing base width $W_B$ of the strip-facing base surface 202 to the radially outward facing width $W_U$ of the radially outward facing surface 204 in a single, constant sloped angle θ or bevel such as shown in FIG. 22A (end view resembling an isosceles triangle) and FIG. 22B (isometric view), it can also in some embodiments include a plurality of different angles, such as more than a single slope angle such as a double, triple or more bevel (e.g., a first angle for a first segment of the height, a second angle for a second part of the height that can be less than or greater than the first angle, and in some cases a third angle for a third part of the height that can be less than or greater than the first angle, and less than or greater than the second angle). FIG. 22C illustrates an end view and FIG. 22D illustrates an isometric view of a wedge dissector with a plurality of differing slopes and associated angles from the strip-facing base surface to the radially outward facing surface, where the angle θ2 between horizontal and an upward slope after a transition point is greater than an angle θ1 between the horizontal strip-facing base edge and the intersecting upward slope (in other words, the first slope S1 from the strip-facing base edge base is less steep than a second slope S2 higher up after a transition point). FIGS. 22E and 22F illustrate an embodiment similar to FIGS. 22C and 22D except the angle θ2 is less than the angle θ1 (in other words, the first slope S1 from the strip-facing base edge base is steeper than a second slope S2 higher up after a transition point).

Alternately, some embodiments may also include a series of steps at different heights where the width transitions to a narrower width and then continues to climb in height. When a series of steps is used in place of the bevel it can sometimes be due to fabrication limitation when methods other than a reel of stainless steel is honed to an edge.

The shapes of the radially outward facing edge or surface (e.g., radially outward facing surface 204 of FIG. 20) can in some embodiments be the same height from one edge 206 of the radially outward facing length or width to the other edge 208. In some embodiments, the height along the radially outward facing surface 204 can vary from one edge 206 to the other edge 208. When the radially outward facing edge or surface 204 varies, typically the radially outward facing edge has a series of raised features herein referred to as wedge dissectors, spikes, or serrating elements 200. In some embodiments, the midpoint of these raised features along the radially outward facing length 204 between edges 206, 208 is the highest point of the radially outward facing surface. However, in some embodiments, the highest point is offset from the midpoint, and there may be a plurality of highest points interspersed by lower point relative to the bounded/base surface 202. The maximal variation of height between edges 206, 208 of the radially outward facing surface 204 of the wedge dissectors 200 and the radially outward facing surface 302 of the base strip 300 between the wedge dissectors 200 can in some embodiments be less than about 80%, 70%, 60%, 50%, 40%, 30%, 20%, 10%, or less than the total height of the wedge dissector 200.

In some embodiments, the base strip 300 has a roughened or otherwise textured inferior surface to aid in adhesion to an outer surface of the underlying balloon. The base strip can have any desired geometry such as square, rectangular, or in some embodiments trapezoidal with the bottom surface having a greater width, such as about or at least about 10%, 20%, 30%, 40%, 50%, 60%, 70%, 80%, 90%, 100%, or more of the top surface. In some embodiments between about ⅓ and ½ of the top surface of the strip 300 is covered by wedge dissectors 200, while between about ½ and ⅔ of the top surface are free of wedge dissectors 200.

Referring to FIG. 21, in some embodiments, the radially outward facing surface viewed from the top can be seen as a line extending from one edge of the radially outward facing length to the other edge of the radially outward facing length (e.g., where $W_U$ is a point assuming 210A is the radially outward facing surface of the device). This would be analogous to a honed or "razor-sharpened" edge with no apparent width. In other embodiments, the top view appears as an unhoned surface that is slightly blunt resembling a rectangle (e.g., if 210B or 210C is the top of the device, and assuming everything above those lines were cut off) with the width of the radially outward facing surface $W_U$ being less than the strip-facing base surface $W_B$ but directly correlated with the slope or slopes between the width edge and height from the strip-facing base surface to the radially outward facing surface. In some embodiments, the top or the radially outward facing surface can be a line, a flat rectangle, a rounded or mounded surface (that might appear to be a rectangle or square in a 2-dimension point of view), or take a pyramidal, wedge, trapezoidal, or other polygonal shape.

In some embodiments, an unhoned width can be a width, for example, that is about or greater than about 1 nm, 5 nm, 10 nm, 50 nm, 100 nm, 500 nm, 1 μm, 2 μm, 5 μm, or 10 μm measured at the radially outward facing edge or surface. In some embodiments, unhoned radially outward facing surfaces of wedge dissectors can be advantageous as being slightly blunt/relatively less sharp than honed edges, in situations for example where creating serrations, indentations, and/or microperforations in a wedge dissector target, for example, is desirable rather than making cuts through the entire luminal wall. In some embodiments, the entire radially outward facing wedge dissector surface has an unhoned width.

Figure 21A:
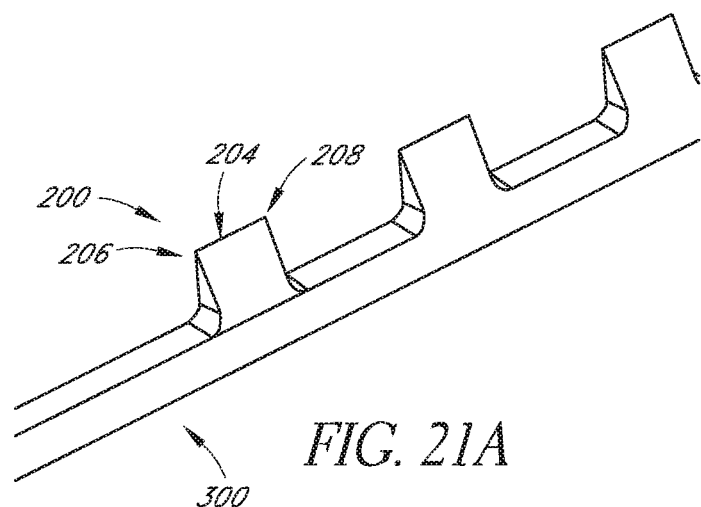
FIGS. 21A-G illustrate various embodiments of wedge dissector geometries.
Figure 21B:
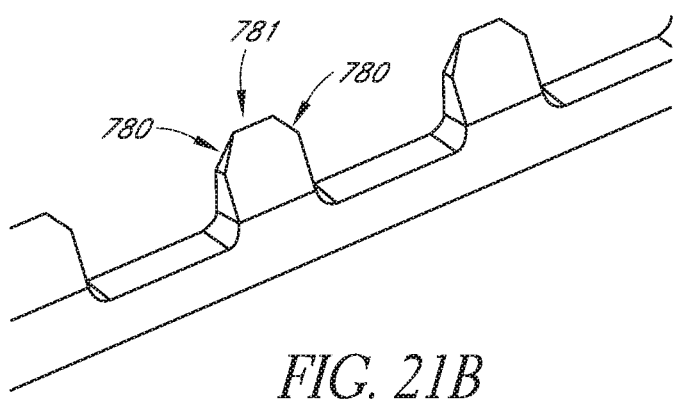
Figure 21C:
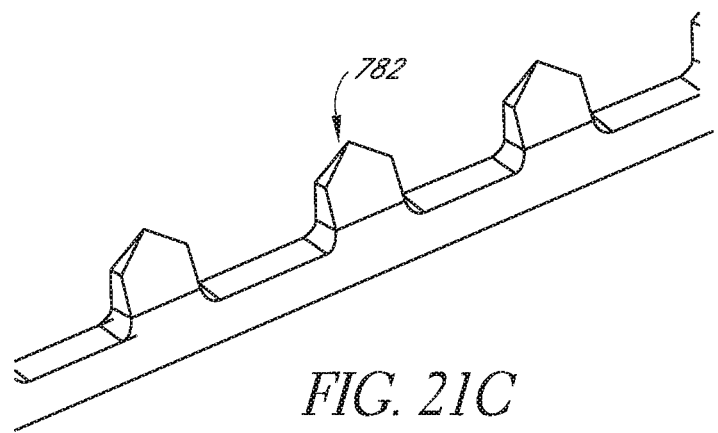
Figure 21D:
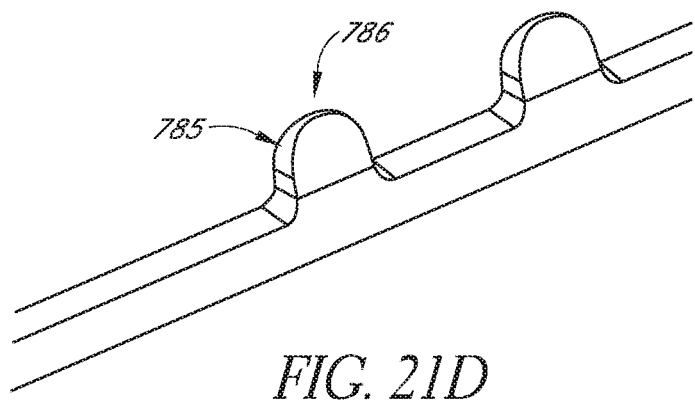

The shape of the wedge dissectors can take many forms, including further non-limiting embodiments as those shown in FIGS. 21A-G. For example, FIG. 21A illustrates wedge dissectors 200 rising from a base strip 300 with a honed/sharp radially outward facing surface 204 from edge 206 to edge 208. FIG. 21B-21C illustrates wedge dissectors with chamfered segments 780 of a radially outward facing surface on both lateral edges that slope or otherwise ramp upward to a honed central single point 782 or edge having a length 781. The slope could be a straight line ramp, or follow a curve as seen in FIG. 21D below. As illustrated in FIG. 21B, the wedge dissector includes lateral segments 780 of radially outward facing surface that increases in height, but decreases in width from a first edge to a central mid-portion 781 having a length with minimal/negligible width, and then increases in width and decreases in width from the midpoint to the second edge. FIG. 21C illustrates a wedge dissector similar to FIG. 21B except that the mid-portion is a single honed apex point 782.

FIG. 21D illustrates a wedge dissector with a radiused radially outward facing surface 785 that increases in height from an edge along a first curved length but decreases in width from a first edge to a central zone such as a midpoint 786, then decreases in height and increases in width along a second curved length to another edge.

Figure 21E:
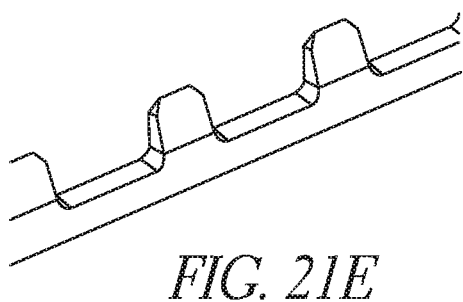
Figure 21F:
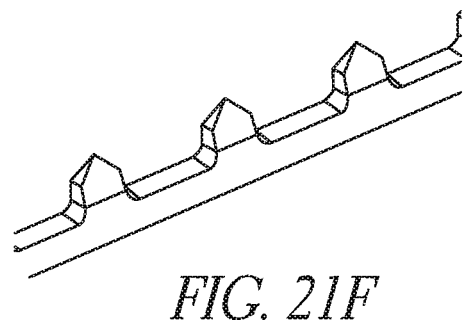
Figure 21G:
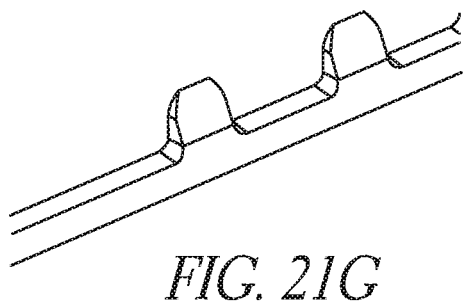

FIGS. 21E-21G illustrate embodiments of wedge dissectors with an unhoned, radially outward facing surface that do not include a sharp honed point or edge (e.g., having a width that is larger than that of a honed edge). FIG. 21E illustrates an embodiment of a wedge dissector somewhat similar to that of FIG. 21B, except the radially outward facing surface is completely unhoned along its length. FIG. 21F illustrates an embodiment of a wedge dissector somewhat similar to that of FIG. 21C, except the radially outward facing surface is completely unhoned along its length. FIG. 21G illustrates an embodiment of a wedge dissector somewhat similar to that of FIG. 21D, except the radially outward facing surface is completely unhoned along its length.

One commonality of the embodiments of FIGS. 21B-21G is that the widths of the radially outward facing surfaces are greater (wider) at the lateral edges, and narrower/less wide more centrally, either at a central point or longer central segment. The height of the radially outward facing surface from one edge to the other edge can be arched or otherwise variable, e.g., with a highest point more centrally and the shortest height at one or more edges when viewed from the side. In these embodiments, the orientation of the narrowest or thinnest (least wide) section of the radially outward facing surface can be along the longitudinal axis of the strip, which may or may not be aligned with the longitudinal axis of the balloon.

In other embodiments, the narrower point or segment need not be symmetric about the midpoint of the length of the radially outward facing surface, but can be asymmetrical/offset from the midpoint of the length in some cases.

Independent of the geometry of the wedge dissectors, some embodiments are characterized by having a bounded end 202 or base (e.g., the spikes have a base the spikes are "attached" to, whether it is a spline (or strip), a balloon, or a molded element of some sort) with a length and width and an radially outward facing surface 204, end or tip with a length and width. In some embodiments, the width of the radially outward facing end is about, or less than about 90%, 85%, 80%, 75%, 70%, 65%, 60%, 55%, 50%, 45%, 40%, 35%, 30%, 25%, 20%, or less than the width of the strip-facing base end, or ranges incorporating any of two of the foregoing values. The width of the strip-facing base end of the wedge dissector (as well as the spline/strip) can be fixed/constant, or alternatively variable in some embodiments.

The wedge dissectors can be a number of different sizes and shapes. In some embodiments, the wedge dissectors are about or less than about, for example, 0.10", 0.09", 0.08", 0.07", 0.06", 0.05", 0.04", 0.03", 0.02", or 0.01" in length at the strip-facing base end or ranges incorporating any of two of the foregoing values, or between about 0.01" and about 0.06", or between about 0.01" and about 0.04" in length. In some embodiments, the wedge dissectors can be about or less than about 0.05", 0.04", 0.03", 0.025", 0.02", 0.015", 0.01", or 0.005" in height as measured from the unbonded edge of the base strip, or between about 0.005" and about 0.025" or between about 0.01" and about 0.025", or between about 0.005" and about 0.015" in some embodiments.

The wedge dissectors can, in some embodiments, have a wedge strip-facing base length of about, or less than about 25 mm, 20 mm, 15 mm, 14 mm, 13 mm, 12 mm, 11 mm, 10 mm, 9 mm, 8 mm, 7 mm, 6 mm, 5 mm, 4 mm, 3 mm, 2 mm, or 1 mm long, or ranges incorporating any two or more of the foregoing values. In some embodiments the wedge dissectors have a wedge strip-facing base length of 2 mm, 2.5 mm, or 3 mm long, or between about 1 mm and about 5 mm long, or between about 1.5 mm and about 3.5 mm long. The wedge dissectors can be spaced apart in a regular or irregular fashion to increase the flexibility of the device.

For example, the space between adjacent wedge dissectors can be, for example, between about 2 times to about 10 times the wedge strip-facing base length of the wedge dissectors, with the wedge dissectors positioned lengthwise. For example, in some embodiments, wedge dissectors with a wedge strip-facing base length about 2.5 mm long can have about 5 mm spaces between them, or about 25 mm spaces between them. In some embodiments, groups of wedge dissectors can be spaced apart with a first smaller ratio of, for example, about 1-4 times the strip-facing base length of the wedge dissectors and then a group can be spaced apart by a second larger ratio, for example, about 8-10 times the strip-facing base length of the wedge dissectors. For example, a first group of wedge dissectors with a strip-facing base length of 2.5 mm can have 5 mm spaces between them and then a second group of wedge dissectors can be spaced 20 mm from first group. The second group can have the same or a different size, shape, and or spacing as the first group.

Figure 23A:
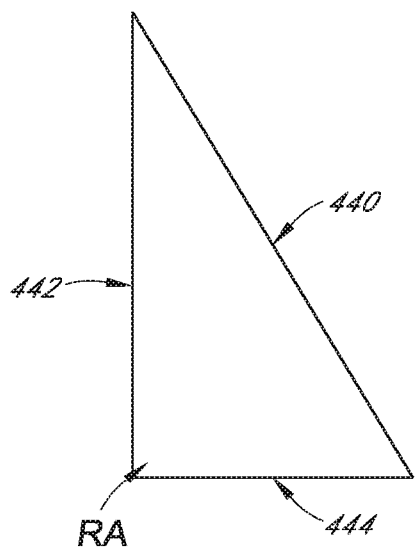
FIGS. 23A-23D illustrate respective end and isometric views of various asymmetric wedge dissector geometries, according to some embodiments.
Figure 23B:
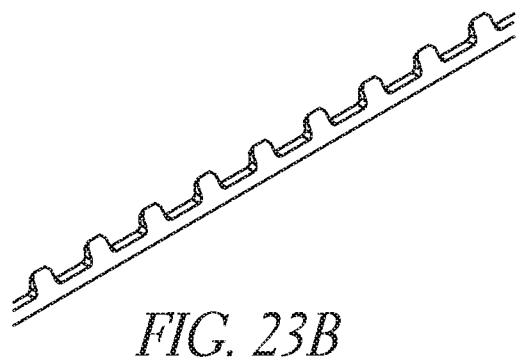
Figure 23C:
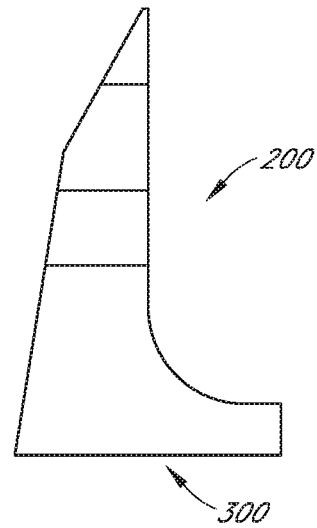
Figure 23D:
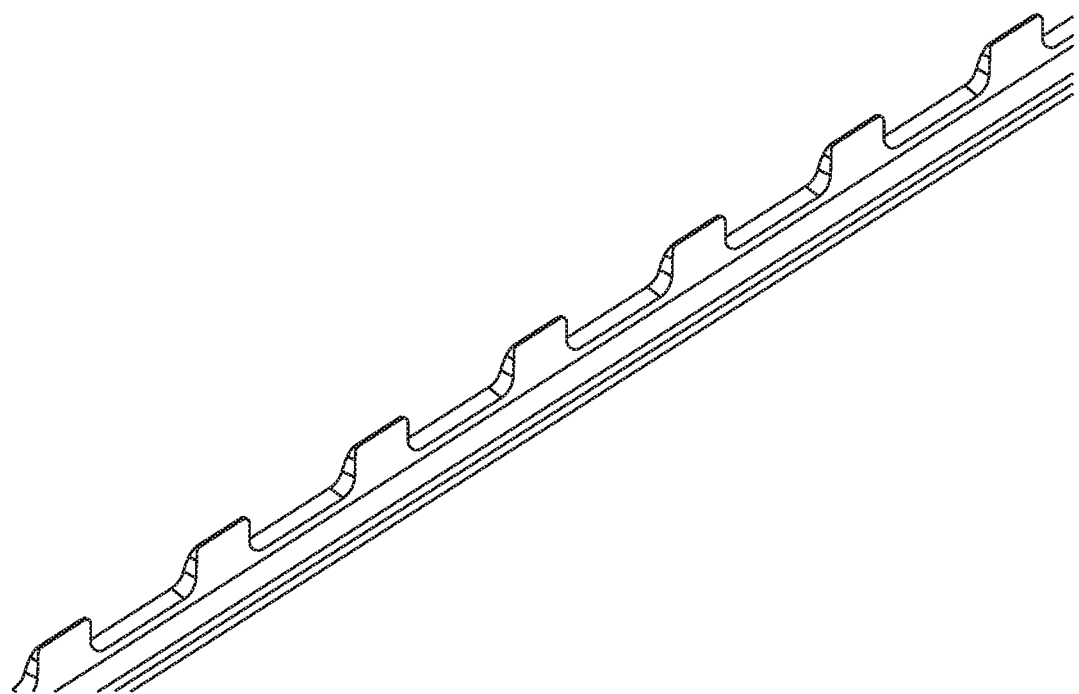
Figure 24:
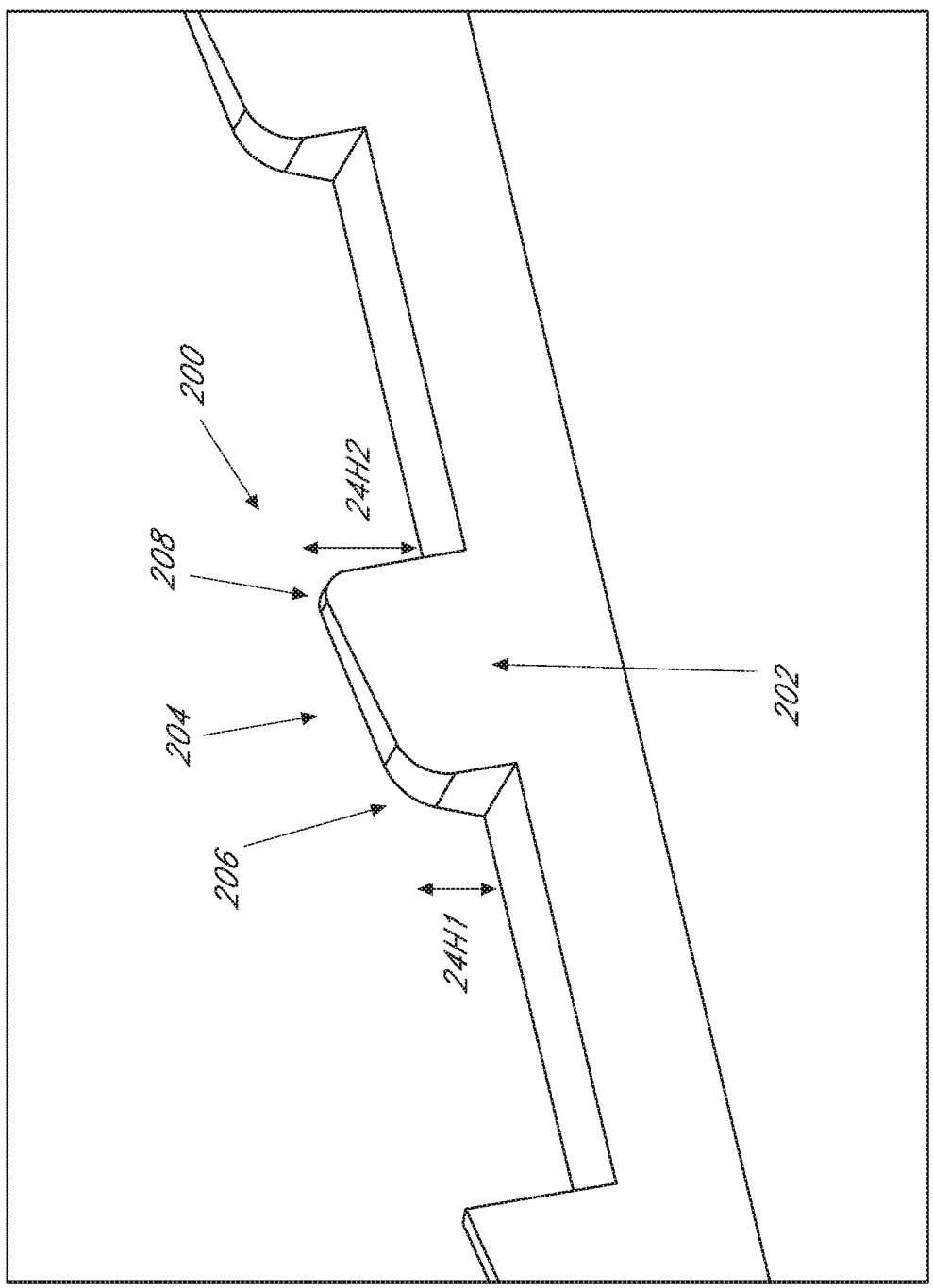
FIG. 24 illustrates an embodiment illustrating how the unbounded surface 204 may have a varying height, according to some embodiments.

The location of the radially outward facing surface relative to the strip-facing base surface is not always centered or symmetric in some embodiments. In other words, the midpoint of the radially outward facing surface can be offset from the midpoint of the strip-facing base surface. FIGS. 23A-B and 24 illustrate an asymmetric radially outward facing surface as an alternate embodiment of the spikes. An asymmetric radially outward facing surface can be off center with respect to the alignment of a radially outward facing width edge directly over the strip-facing base width edge. In this configuration only one of the strip-facing base width edges has a tilted edge 440 climbing in height off of the radially outward facing surface while the other height edge 442 is perpendicular, at a 90 degree (right) angle RA to the strip-facing base surface 444, seen best in FIG. 23A. In addition, the edges of the radially outward facing surface in one or both of the width ends and/or in one or both of the length ends can be chamfered or beveled or have a radius. In some variations, the radially outward facing surface location is limited to the area projected upward over the strip-facing base surface. The radially outward facing surface can be a sharp line (e.g., honed edge) or any of the described unhoned edge variations for example. FIG. 23C-D illustrates an embodiment where the total volume or substantially the total volume of the wedge dissector rises/is present over less than the entire width (or surface area) of the base of the strip, such as about or less than about 70%, 60%, 50%, 40%, or 30% of the width or surface area of the strip, for example, and are thus the wedge dissectors are asymmetrically offset either anteriorly or posteriorly from the longitudinal axis of the strip.

FIG. 24 illustrates an embodiment illustrating how the radially outward facing surface 204 may have a varying height (increasing from first height 24H1 at first edge 206 to second height 24H2 at second edge 208) from the strip-facing base surface 202 and may include edge profiles that are rounded with a radius of curvature of the radially outward facing length edges 206, 208. Here we see a wider radius of curvature at one edge 206 that has a shallow height 24H1 measured from the strip-facing base surface 202 while the radius of curvature of the opposite edge 208 is narrower and has a longer height 24H2 measured from the strip-facing base surface 202.

In some embodiments, the various wedge dissector features described herein can offer unique advantages to aid in delivery of the device, including but not limited to reducing vessel trauma if the radially outward facing surface is positioned outside of the delivery apparatus and/or can contact the luminal wall and has the potential to scrape the vessel wall during movement through the artery. This can be the case, for example, in embodiments with wedge dissectors with unhoned, radially outward facing surfaces.

In addition, not to be limited by theory, certain shapes may offer more effective penetration into the tissue. For instance, wedge dissectors that include chamfered or rounded radially outward facing edges can potentially enter the vessel wall with less force (requires less pressure to penetrate tissue) while still maintaining an effective micro channel to weaken the tissue and enable tissue expansion with minimal vessel trauma and cellular injury.

Furthermore, while there have been prior proposals for providing blades or sharp edges or scoring wire on a balloon during angioplasty or other procedure for cutting or scoring the plaque in conjunction with balloon expansion, these prior methods are deemed to have problems or disadvantages which are eliminated or avoided by systems and methods as disclosed herein. Cutting or scoring a luminal wall, such as, for example, the plaque during angioplasty can be performed at high pressures that can result in high injury to the blood vessel. The cutting blades, edges or scoring wire can be forced into the wall of the blood vessel at the same time that the angioplasty balloon is expanded to dilate the plaque. During this process the cutting blades, edges, or scoring wire can be forced into the vessel wall at oblique angles and can plow up the plaque potentially increasing the tendency for dissections. In contrast, in some embodiments, wedge dissectors employ can be expanded into the plaque at low pressures so as to form precise microperforations, serrations, and/or indentations in a radially outward direction that form precise indentations, cleavage lines or planes in the plaque or other location in the luminal wall, or other target. The radially outward facing surface of the wedge dissector can push into the plaque or other luminal surface in small surface areas, thereby being much less likely to plow up the plaque or luminal surface.

Wedge dissectors can be designed, in some embodiments, to provide a series of oriented punctures or serrations into (but not completely through in some cases) a diseased vessel wall. The wedge dissectors produce a linear line of weakness or perforations that enable more effective and gentler vessel lumen expansion. The perforations can also serve as a pathway for pharmaceutical agents. The pharmaceutical agents could be delivered using a drug coated balloon, either incorporated with the device disclosed herein, or on a separate device that is used following the usage of the disclosed device. In some embodiments, the wedge dissectors can be detachable from the base strip, and/or be coated or otherwise impregnated with one or more pharmaceutical agents for drug delivery.

Figure 25A:
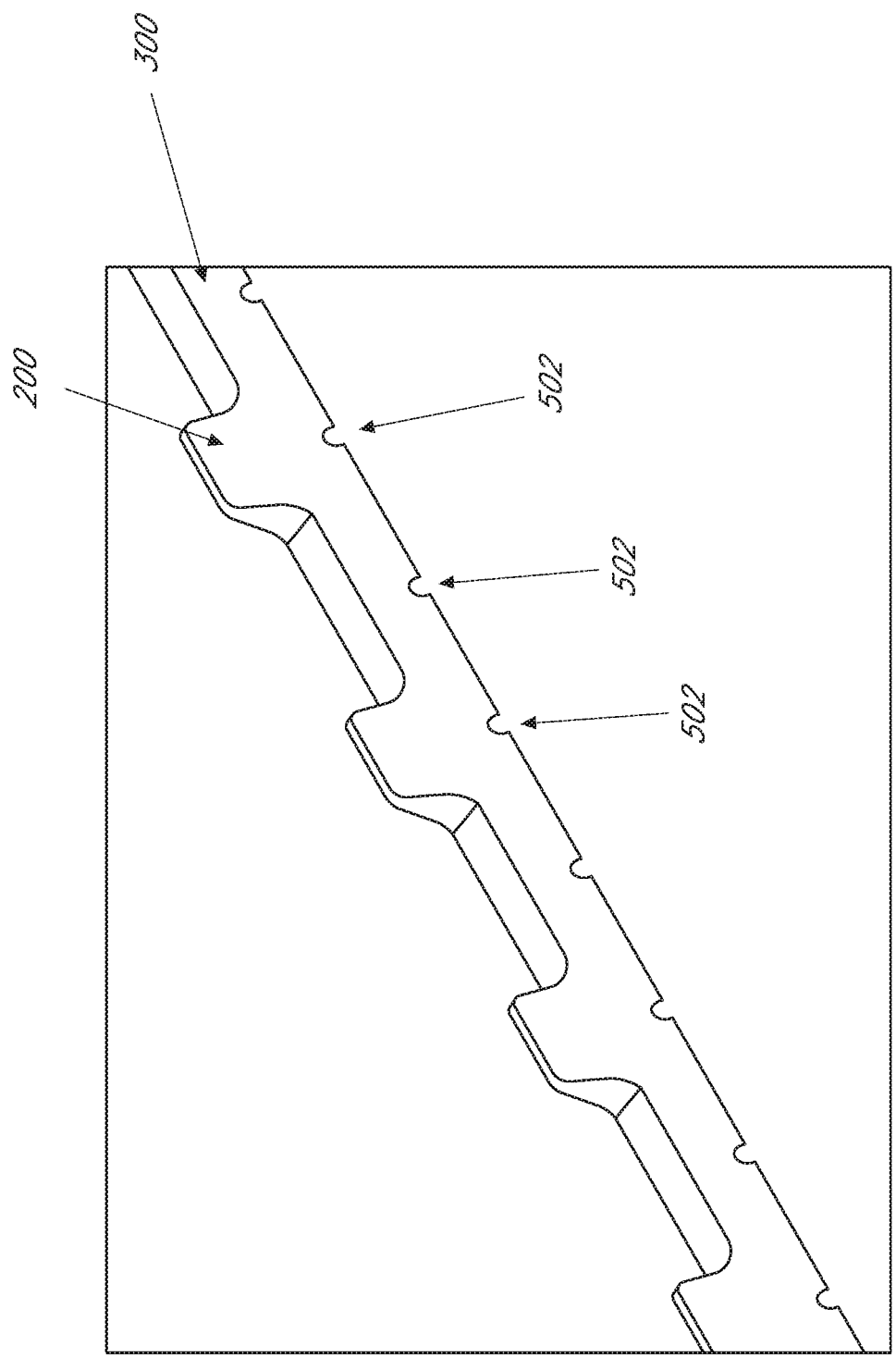
Figure 25B:
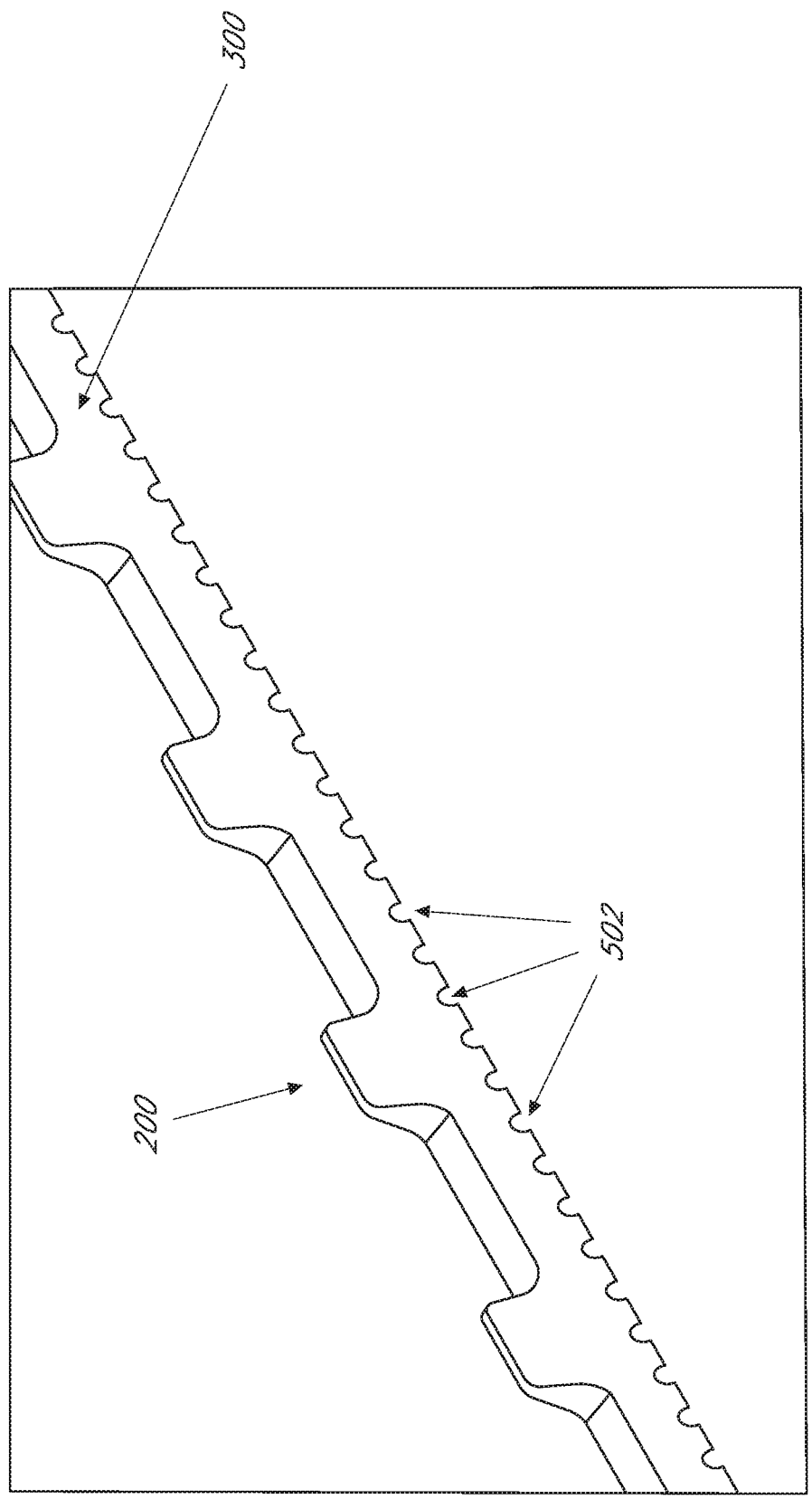
Figure 25C:
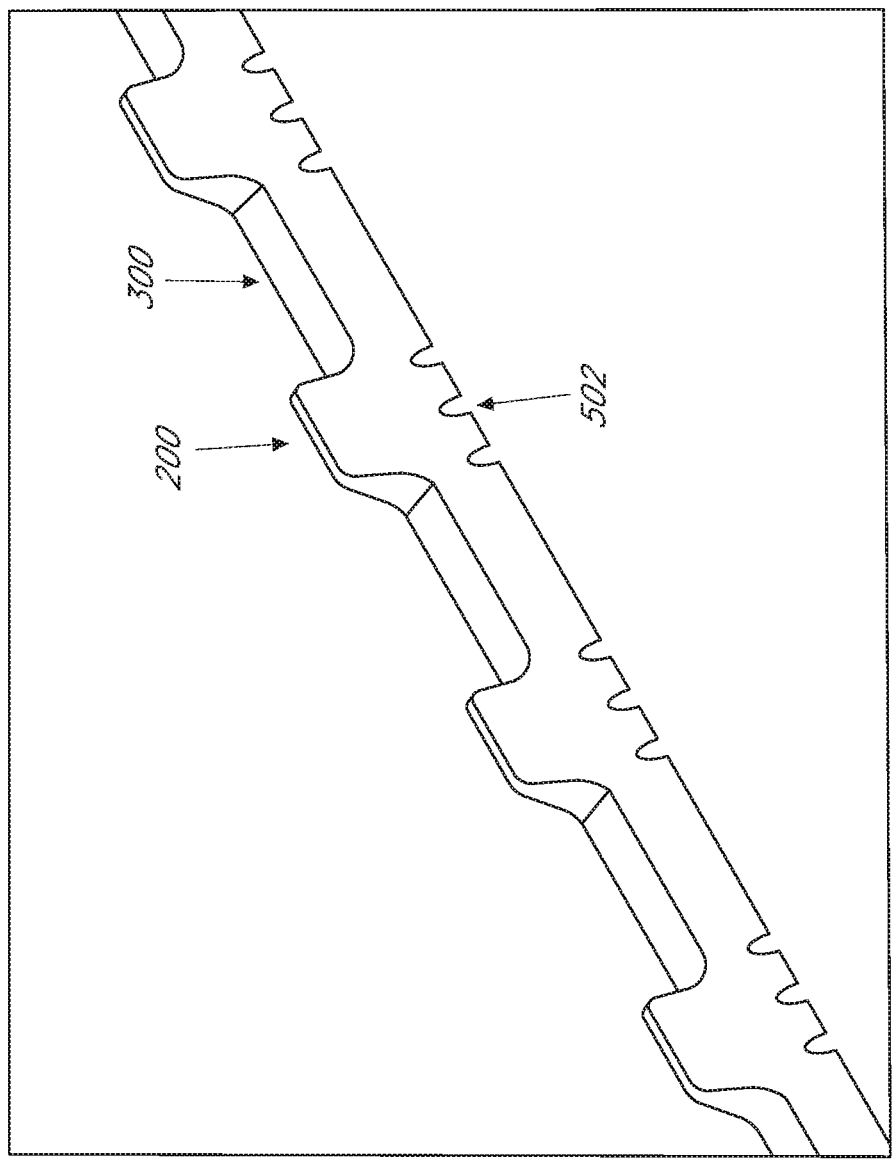
Figure 25D:
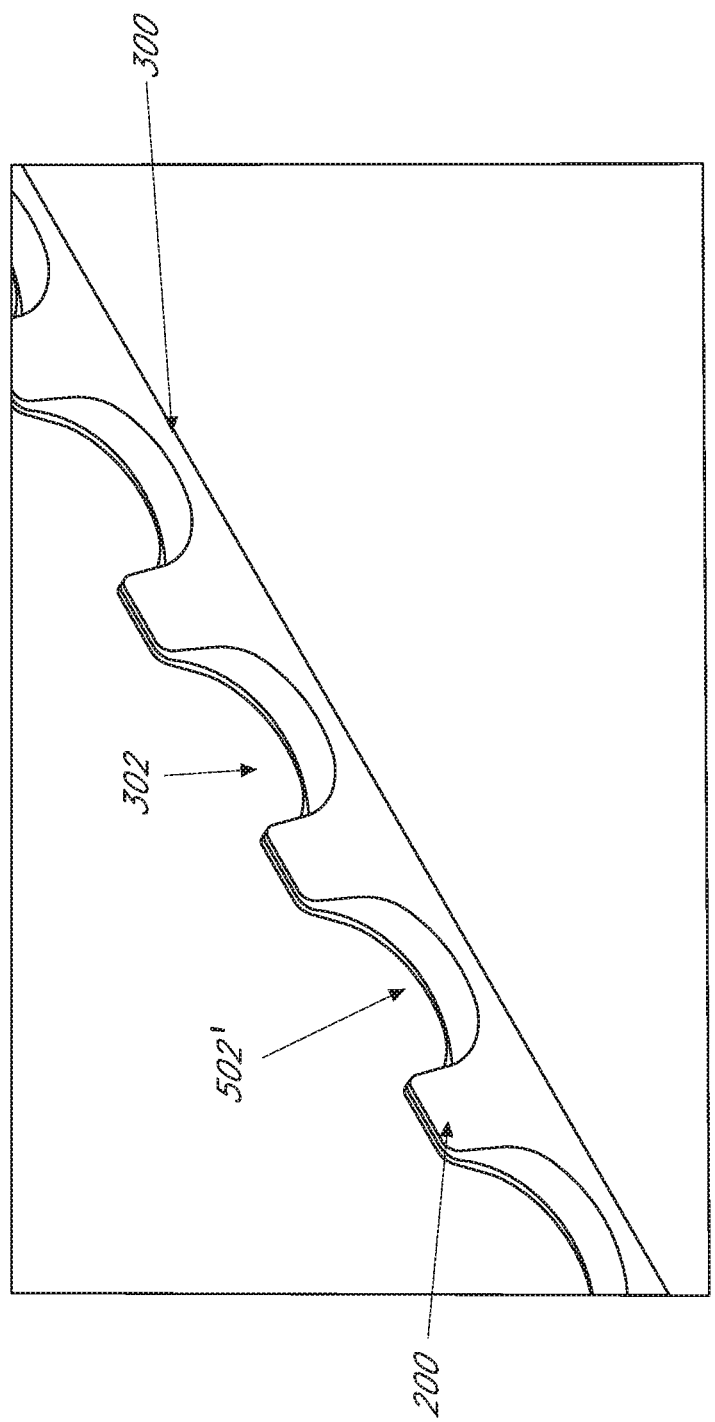
Figure 25E:
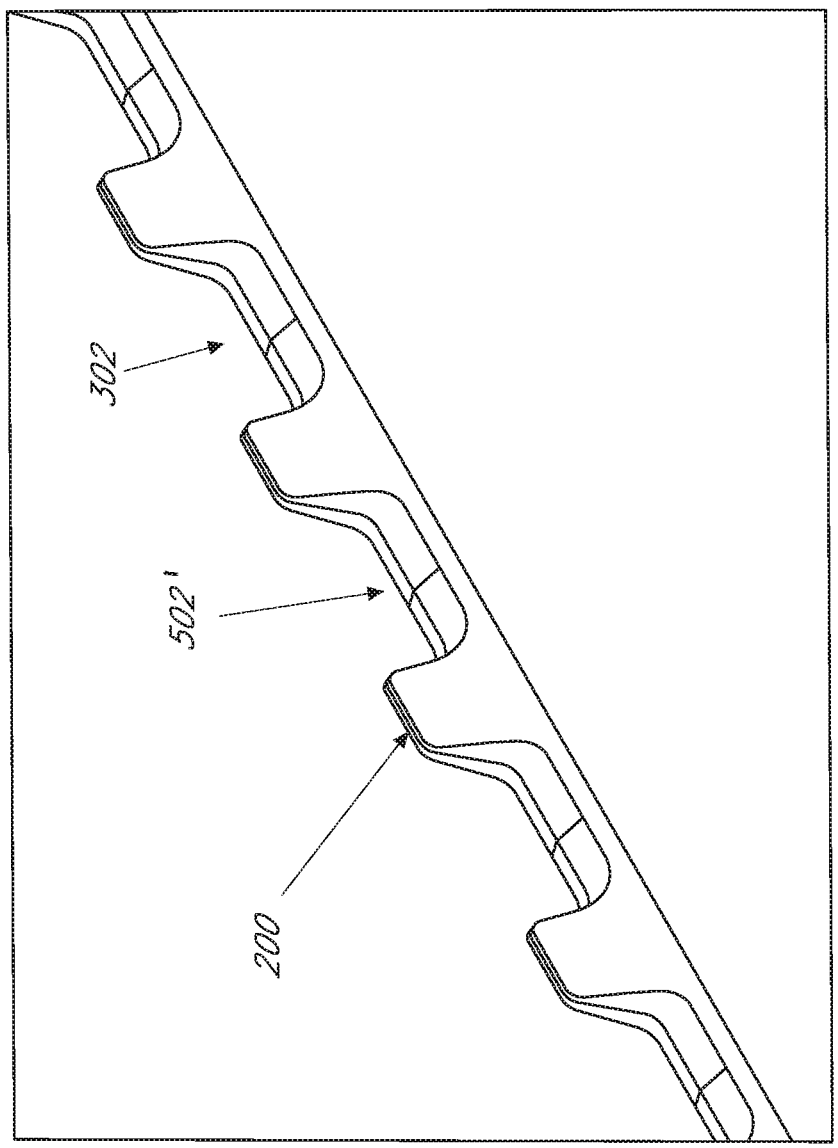
Figure 25F:
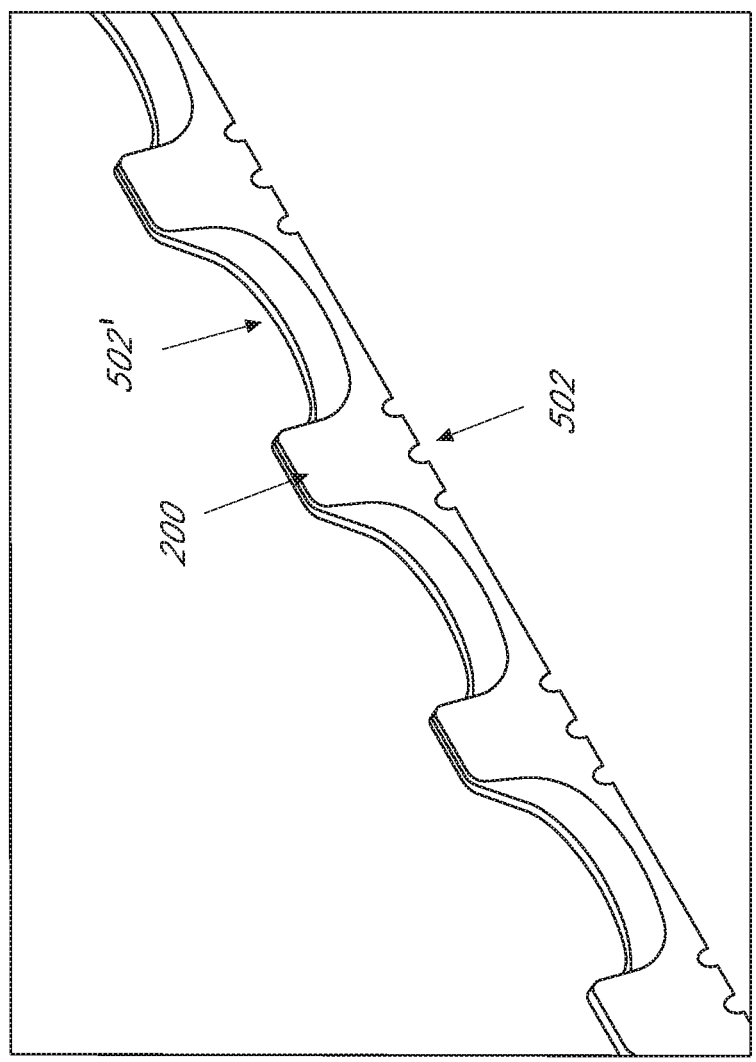
Figure 25G:
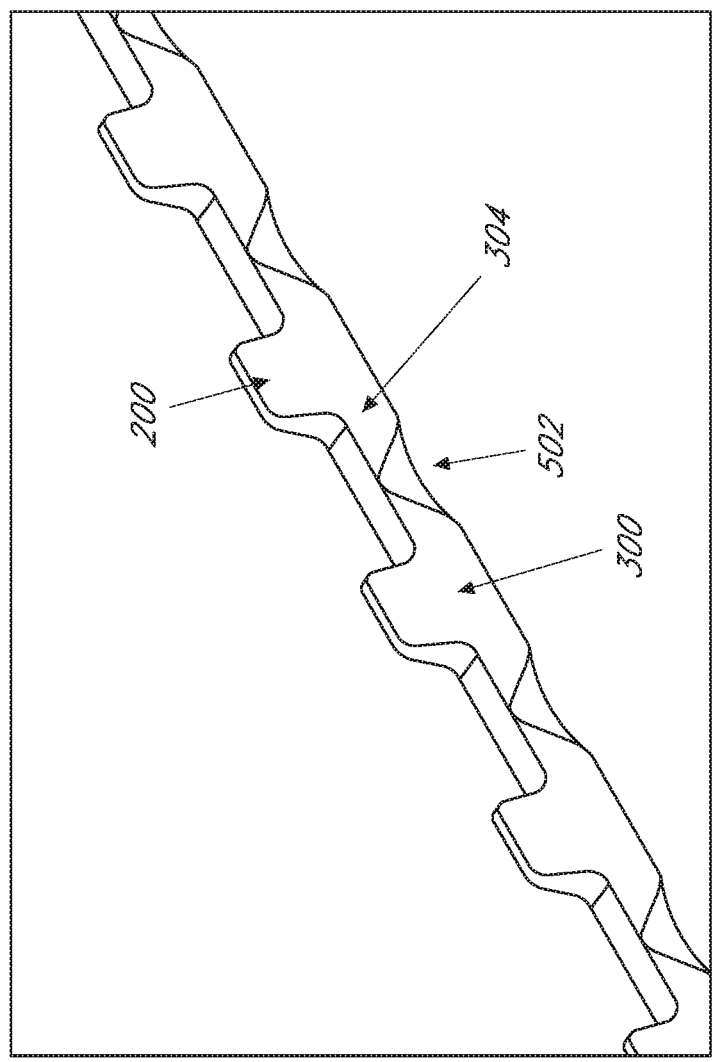
Figure 25I:
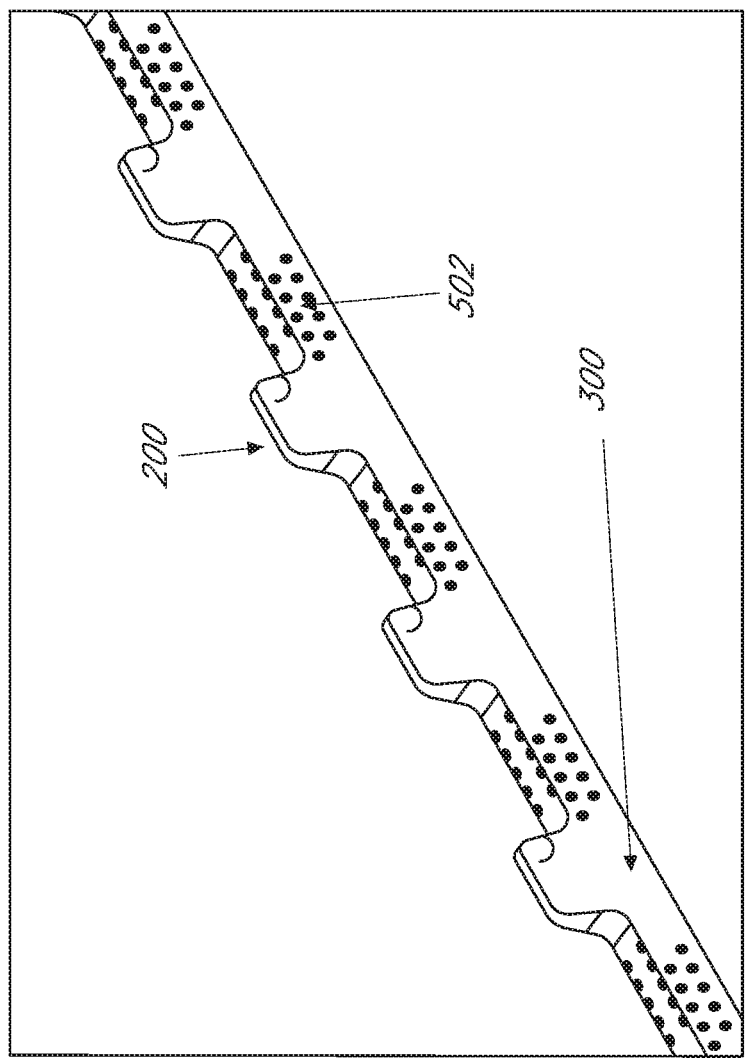
Figure 25J:
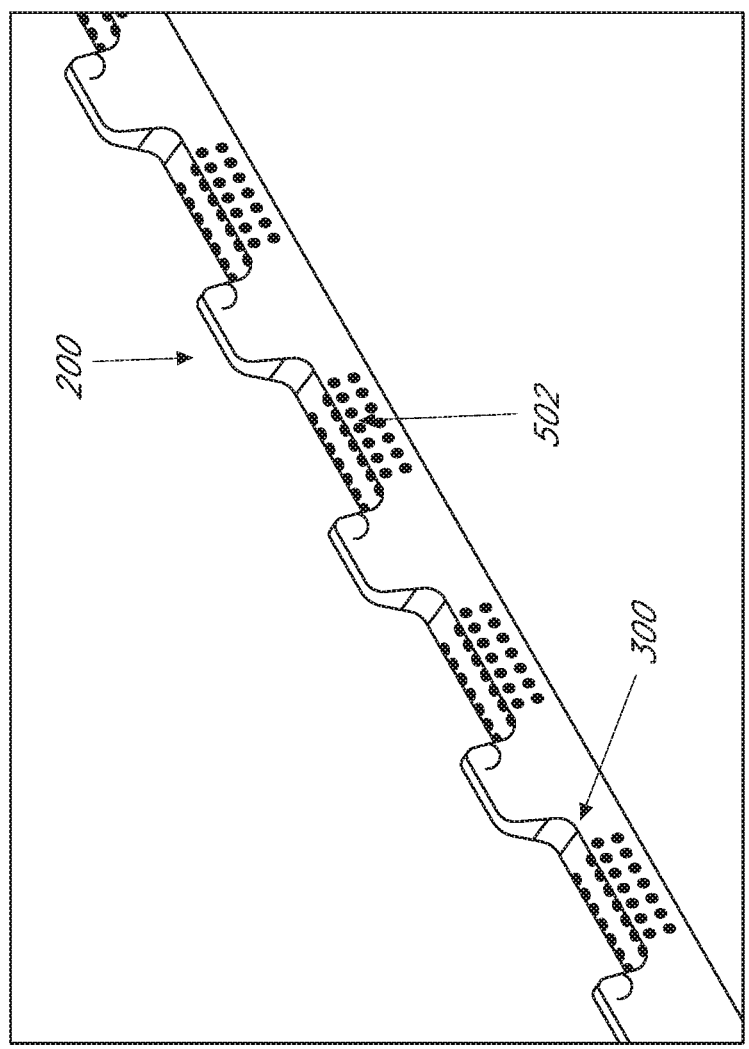
Figure 25K:
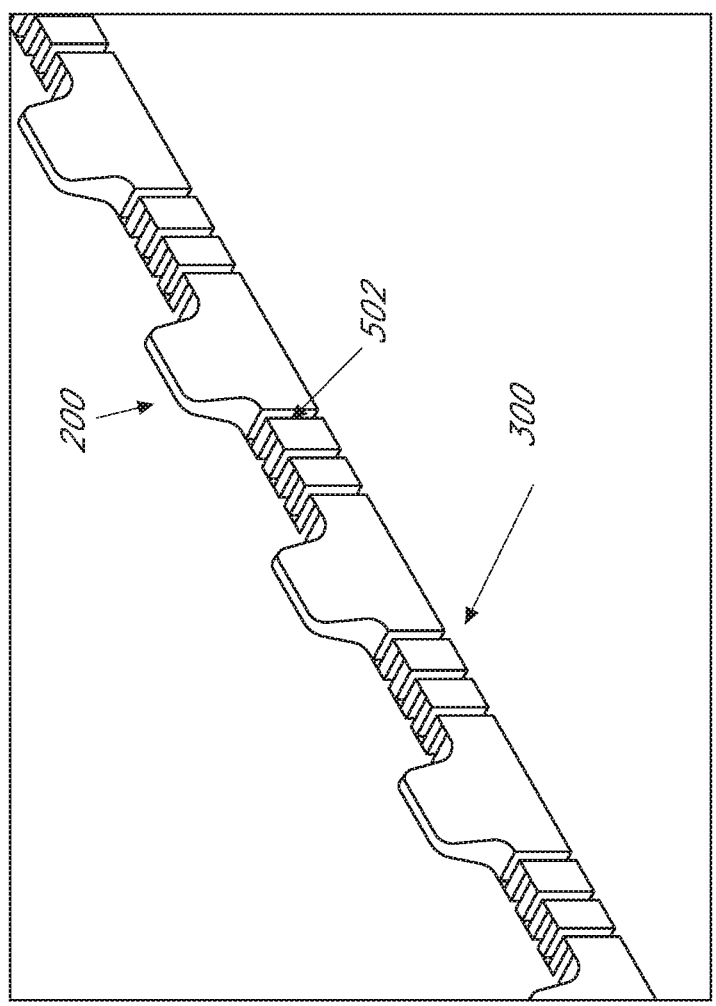
Figure 25O:
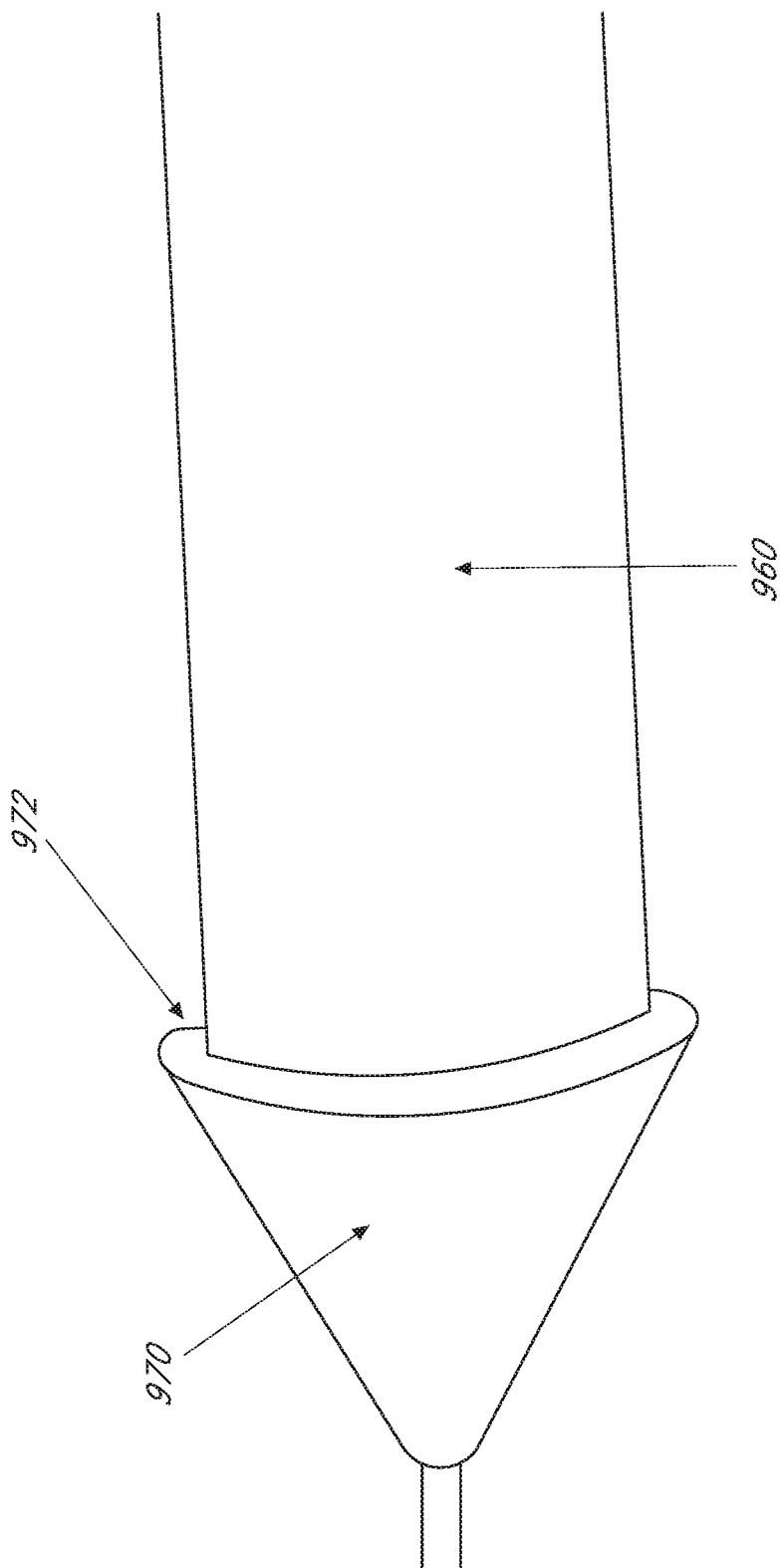
FIG. 25O illustrates a cone ramp for a balloon, according to some embodiments.
Figure 26:
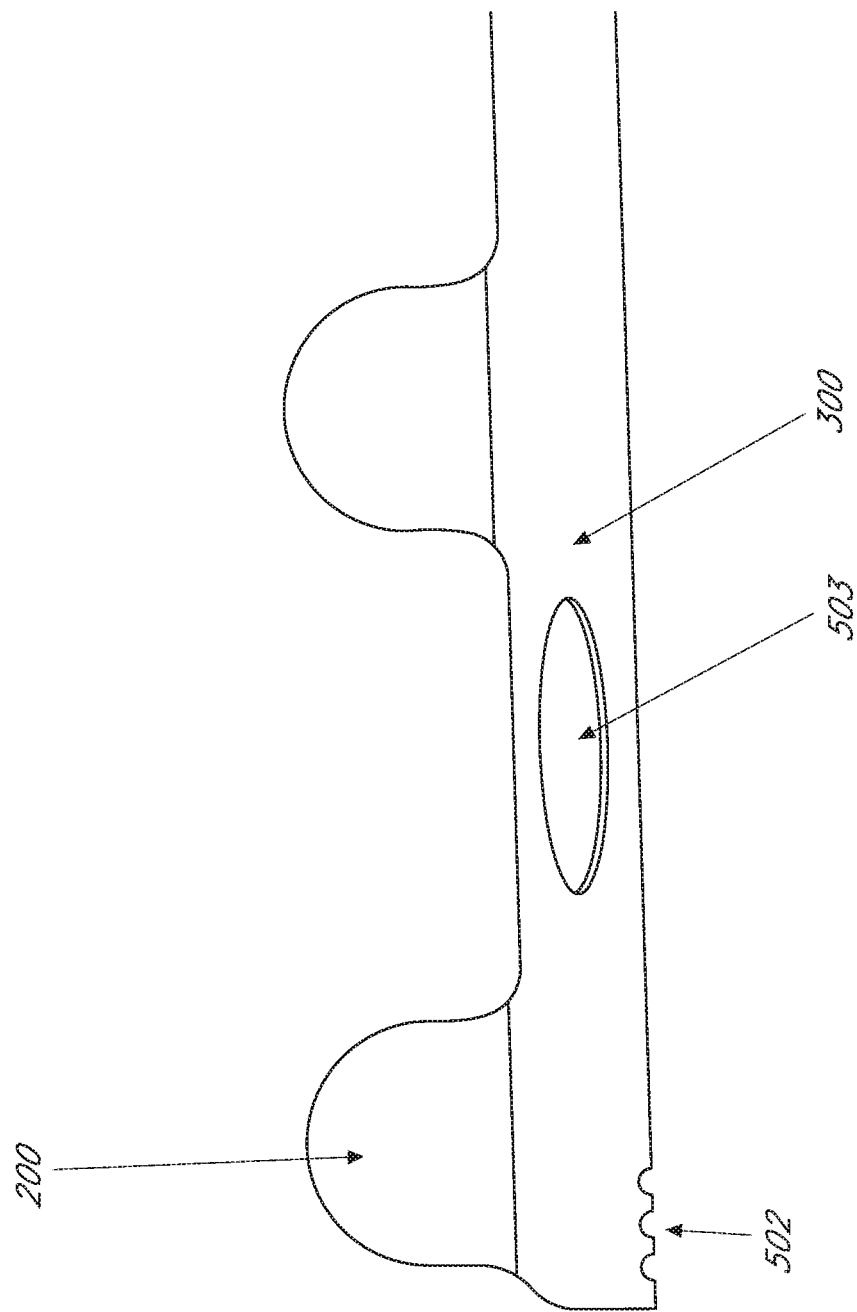
FIG. 26 illustrate another embodiment of strips having reliefs, according to some embodiments.

To reduce potential rigidity of the spline, or base strip, it is envisioned that a series of reliefs on the spline can be added in some embodiments, as illustrated in FIGS. 25 and 26. The relief elements can be produced in many different ways with the intent to have material removed and offer a more pliable spline for the wedges to be strip-facing base to. Relief can be made in the base of the spline opposite the wedge dissector strip-facing base surface, at the top of the spline directly adjacent the wedge dissector strip-facing base surface, or in both locations, e.g., a combination of top and bottom. The relief can also be made on the side of the spline, or apertures strip-facing base by other areas of the spline can be added to the spline. Any combination of top, bottom, side or through apertures can be added to the spline to offer relief.

In some embodiments, as illustrated in FIGS. 25 and 26, the strip 300 can have relief holes or slits located at the top, bottom, centered or off center that are either circular, rectangular, linear, triangular, or elliptical or combinations thereof (See FIGS. 25 and 26). The strips offer a supporting base infrastructure, intended to be flexible and follow the movement of the balloon, for the wedges to be oriented correctly.

The relief holes illustrations as shown in FIGS. 25 and 26 can be specifically designed to offer a pathway for balloon-based pharmacological agents to migrate through; in addition, they offer strain relief in the surface to enhance the deliverability of the device in tortuous anatomy. FIGS. 25A-C illustrate embodiments of wedge dissectors with reliefs 502 on the inferior surface 500 of the strips 300 opposite the bounded surface of the wedge dissectors 200. FIG. 25A illustrates an embodiment where the reliefs 502 are regularly spaced apart approximately a length of the bounded surface of each wedge dissector 200. FIG. 25B illustrates an embodiment where the reliefs 502 are regularly spaced apart 50% or less of the length of the bounded surface of each wedge dissector 200. FIG. 25C illustrates an embodiment where each relief 502 is spaced apart 50% or less of the length of the bounded surface of each wedge dissector 200, but the reliefs 502 are grouped only under the wedge dissectors and are not present under the strip sections in between the wedge dissectors. In other embodiments, the reliefs 502 are grouped only under the strip sections in between the wedge dissectors, but not under the strip sections directly below the wedge dissectors.

FIGS. 25D-25E illustrates an embodiment where the reliefs 502' are present on the top (bounded or superior-facing surface 302) of the strip in between the wedge dissectors. In FIGS. 25D and 25E, the reliefs form depressions in the superior-facing surface 302 of the strips in between wedge dissectors with a generally curved based as illustrated in FIG. 25D, and a relatively more square or rectangular base as illustrated in FIG. 25E, with or without rounded edges. FIG. 25F is an embodiment combining two different kinds of reliefs 502 found in the embodiments of FIGS. 25C and 25D. Other permutations of combinations are also possible, depending on the desired clinical result. FIGS. 25G and 25H illustrate other embodiments where the reliefs 502 are on an anterior 304 and/or posterior side surface of the strip 300. FIG. 25G illustrates generally pyramidal-shaped reliefs 502, while FIG. 25H illustrates generally arcuate reliefs 502. The reliefs can be spaced axially apart from the wedge dissectors as shown, and/or spaced axially aligned with wedge dissectors in other embodiments. FIGS. 25I and 25J illustrate embodiments where the reliefs 502 take the form of vertically (FIG. 25I) or horizontally (FIG. 25J) oriented through-channels, which can be spaced axially apart from the wedge dissectors as shown, or in another configuration. In some embodiments, the reliefs can be oriented at an oblique angle to the longitudinal axis of the strip. FIG. 25K illustrates an embodiment where the reliefs 502 take the form of slots on the anterior and/or posterior side surfaces, bounded base surface, and/or other locations.

To aid in removal of material fabrication from the initial blade, the strips can include tabs along the base or bonded surface in some embodiments. The tabs can aid in controlling long strips from vibration or movement during the material removal. Once fabrication is completed, the tabs are then removed. In some embodiments, the tabs have an inset that they sit at the base of the strip. In some embodiments, inset reliefs can serve as the tabs, and be advantageous during the manufacturing process, when several strips are, for example, laser cut from the same sheet of source material. In some embodiments, a complementary protrusion (e.g., a tab or related structure) on or connected to an adjacent area of the source material to be laser cut can fit into an inset relief of a strip adjacent to the source material to maintain proper alignment of the strips during laser cutting/manufacturing. This can keep the strips in place during laser cutting, and prevent undesired migration and misalignment of a strip relative to an adjacent material area due to, for example, laser vibrations, which can decrease product yields. In some embodiments, reliefs for manufacturing stability purposes need not be inset and can take the form of tabs that protrude outwardly from the base of the tab. In some embodiments, these tabs are later removed by laser cutting or other methods prior to bonding or other attachment to the outer surface of the balloon, to prevent inadvertent puncture of the balloon. Some embodiments are illustrated in FIGS. 25L and 25M, which schematically illustrate strips 300 with wedge dissectors 200 during the strip and manufacturing process. Also shown is tab 580, which can be laser cut out of the source material, and be connected with one end at an adjacent area of the source material 581 and the other end inset in an inset relief 502 in, for example, an inferior surface of the strip 300. The inset relief 502 can be any pattern as previously described, for example, in FIGS. 25A-25K or others, and in some embodiments are shown underneath the wedge dissector 200. FIG. 25M illustrates the tab 580 which can be cut into segments 588, 589 following the manufacturing process when it is no longer required to hold the strip 300 in place with respect to adjacent source material 581, and the strip 300 can then be separated for attachment to a balloon or other device. The inset can allow for the tab to be removed while minimizing that amount of material that could potentially hang below the base of the strip which might interfere with the bonding of the strip to the balloon or other expansion device.

In some embodiments, balloons can be pleated and crimped down to the very narrow profile allowing the device to be delivered through and introducer sheath with a narrow diameter. Once the balloon has been deployed and deflated, the post-inflated balloon profile can be larger than its original pleated and crimped down diameter. This new profile may have strips that sit proud of the balloon profile potentially scraping the arterial wall or snagging on the opening of an accessory device such as an introducer sheath. The following elements, which are in general described as ramps, can address this potential issue, according to some embodiments.

FIG. 25N illustrates schematically an embodiment of a ramp 680 of adhesive or other material is placed at (e.g., over) one, as shown, or both lateral ends 333 of some or all of the strips 300. This can be, in some cases, in addition to adhesive placed at other locations such as under the strips (e.g., on the inferior surface of the strips 300) to attach the strips 300 to the balloon. The ramp 680 can offer an effective flexible interface between the edge of the flexible balloon (not shown) and the semi-rigid strip 300, as the ramp 680 can be made of a material (e.g., an adhesive) that is relatively more flexible than that of the strip 300. The ramp 680 can be designed in some embodiments to gently slope from the balloon surface (not shown) to the edge of strip. In some embodiments, the adhesive ramps 680 can advantageously both retain strips and offer protection from undesired strip interaction 300 with ancillary devices during a procedure.

In some embodiments, a feature that can be incorporated into the balloon element is a cone ramp. The cone ramp feature can be implemented in several ways. In one embodiment, the cone ramp is fabricated by taking a cone configuration for a larger balloon, for example taking a cone for a 6 mm balloon, or 5.5 mm balloon and incorporating it using known methods to be attached to a 5 mm balloon. One such embodiment is shown schematically in FIG. 25O. The cone 970 can have in some cases an outer diameter that is larger than that of the outer diameter of the balloon 960, such as about or at least about 5%, 10%, 15%, 20%, or more than that of the outer diameter of the balloon 960, or between about 5% and about 20% larger than that of the outer diameter of the balloon 960 in some embodiments. The relatively larger cone 970 will sit proud of the balloon 960 generating a lip 972 at the intersection of the balloon body. The lip 972 can be beneficial in reducing the potential of the metal strip edges to be snagged or lifted off when the balloon is deflated and retracted through the introducer catheter.

In some embodiments, illustrated in FIG. 25P, included are a series of rails 980 along the cone 970 to serve as support or stiffening structures, and assist in collapsing the balloon 960 as it enters an introducer catheter (not shown). In some embodiments, the rails 980 are oriented/align with the longitudinal axes of the strips, furthering enhancing the function of pushing the strips toward the middle of the balloon as the cone is pulled through the introducer.

In some embodiments, also disclosed herein are balloons that can have depressions in the outer surface of the balloon for strip attachment. A series of depressions can be produced on the surface of the balloon. The depressions can, in some embodiments, configured to be wide enough and long enough to allow the strips to be placed within, such as entirely within the depression. The depths of the depressions can be sized to limit the likelihood that the strips could get caught on the distal opening of the introducer during balloon retraction.

The use of the through-holes or microchannels either in the spline or on the spline sides can offer a mechanism for a therapeutic agent such as, for example, one or more drugs, nanoparticles, and/or stem cell transport from the balloon surface into the diseased luminal surface through capillary or diffusion action and/or utilization of the balloon pressure forcing the drug, nanoparticles, and/or stem cells through the micro channels on to the surface or into the diseased site. Alternatively, the microchannels or modified surfaces can provide a reservoir for drug, nanoparticles, or stem cells or other therapeutics to be placed and protected during transport to the diseased site. In some embodiments, the drug may be any drug known in the art. In some embodiments, examples of drugs that may be suitable for use in the methods and devices of this invention depending, on the specific disease being treated, and with consideration of the physical properties of the drug, include, without limitation, anti-restenosis, pro- or anti-proliferative, anti-inflammatory, anti-neoplastic, antimitotic, anti-platelet, anticoagulant, antifibrin, antithrombin, cytostatic, antibiotic, anti-enzymatic, anti-metabolic, angiogenic, cytoprotective, angiotensin converting enzyme (ACE) inhibiting, angiotensin II receptor antagonizing and/or cardioprotective drugs.

Examples of antiproliferative drugs include, without limitation, actinomycins, taxol, docetaxel, paclitaxel, sirolimus (rapamycin), biolimus A9 (Biosensors International, Singapore), deforolimus, AP23572 (Ariad Pharmaceuticals), tacrolimus, temsirolimus, pimecrolimus, zotarolimus (ABT-578), 40-O-(2-hydroxy)ethyl-rapamycin (everolimus), 40-O-(3-hydroxypropyl)rapamycin (a structural derivative of rapamycin), 40-O-[2-(2-hydroxy)ethoxy]ethyl-rapamycin (a structural derivative of rapamycin), 40-O-tetrazole-rapamycin (a structural derivative of rapamycin), 40-O-tetrazolylrapamycin, 40-epi-(N-1-tetrazole)-rapamycin, and pirfenidone.

Examples of anti-inflammatory drugs include both steroidal and non-steroidal (NSAID) anti-inflammatories such as, without limitation, clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone, dexamethasone dipropionate, dexamethasone acetate, dexmethasone phosphate, momentasone, cortisone, cortisone acetate, hydrocortisone, prednisone, prednisone acetate, betamethasone, betamethasone acetate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lornoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus and pimecrolimus.

Examples of antineoplastics and antimitotics include, without limitation, paclitaxel, docetaxel, methotrexate, azathioprine, vincristine, vinblastine, fluorouracil, doxorubicin hydrochloride and mitomycin.

Examples of anti-platelet, anticoagulant, antifibrin, and antithrombin drugs include, without limitation, heparin, sodium heparin, low molecular weight heparins, heparinoids, hirudin, argatroban, forskolin, vapiprost, prostacyclin, prostacyclin dextran, D-phe-pro-arg-chloromethylketone, dipyridamole, glycoprotein IIb/IIIa platelet membrane receptor antagonist antibody, recombinant hirudin and thrombin, thrombin inhibitors such as ANGIOMAX® (bivalirudin, from Biogen), calcium channel blockers such as nifedipine, colchicine, fish oil (omega 3-fatty acid), histamine antagonists, lovastatin, monoclonal antibodies such as those specific for Platelet-Derived Growth Factor (PDGF)

receptors, nitroprusside, phosphodiesterase inhibitors, prostaglandin inhibitors, suramin, serotonin blockers, steroids, thioprotease inhibitors, triazolopyrimidine, nitric oxide or nitric oxide donors, super oxide dismutases, super oxide dismutase mimetic and 4-amino-2,2,6,6-tetramethylpiperidine-1-oxyl (4-amino-TEMPO).

Examples of cytostatic or antiproliferative drugs include, without limitation, angiopeptin, angiotensin converting enzyme inhibitors such as captopril, cilazapril or lisinopril, calcium channel blockers such as nifedipine; colchicine, fibroblast growth factor (FGF) antagonists; fish oil (ω-3-fatty acid); histamine antagonists; lovastatin, monoclonal antibodies such as, without limitation, those specific for Platelet-Derived Growth Factor (PDGF) receptors; nitroprusside, phosphodiesterase inhibitors, prostaglandin inhibitors, suramin, serotonin blockers, steroids, thioprotease inhibitors, triazolopyrimidine (a PDGF antagonist) and nitric oxide.

Examples of ACE inhibitors include, without limitation, quinapril, perindopril, ramipril, captopril, benazepril, trandolapril, fosinopril, lisinopril, moexipril and enalapril.

Examples of angiotensin II receptor antagonists include, without limitation, irbesartan and losartan.

Other therapeutic drugs that may find beneficial use herein include, again without limitation, alpha-interferon, genetically engineered endothelial cells, dexamethasone, antisense molecules which bind to complementary DNA to inhibit transcription, and ribozymes, antibodies, receptor ligands such as the nuclear receptor ligands estradiol and the retinoids, thiazolidinediones (glitazones), enzymes, adhesion peptides, blood clotting factors, inhibitors or clot dissolving drugs such as streptokinase and tissue plasminogen activator, antigens for immunization, hormones and growth factors, oligonucleotides such as antisense oligonucleotides and ribozymes and retroviral vectors for use in gene therapy, antiviral drugs and diuretics.

In other embodiments, a combination of any two, three, or other number of the foregoing drugs or other therapeutic agents can be utilized depending on the desired clinical result.

One method for laying down drugs, nanoparticles, stem cells or other therapeutics in specific regions such as the relief holes is the use of a direct write process, e.g., MICROPENNING (MICROPEN Technologies, Honeoye Falls, N.Y.), to deposit material onto a surface. In general, the term "direct write" describes a printing or patterning method that employs a computerized, motion-controlled stage with a motionless pattern generating device to dispense flowable materials in a designed pattern onto a surface. MICROPENNING is a flow-based micro-dispensing technique in which printed materials are extruded with a high degree of control through a syringe and a precision pen tip. The pen tip "rides" on the surface of the material, not touching the substrate surface and is capable of place precise amount of materials in precise locations.

FIG. 26 illustrates an embodiment of a strip 500 with reliefs 502 on the inferior surface of the strips 300 opposite the bounded surface of the wedge dissectors 200, with additional relatively larger apertures 503 in between wedge dissectors 200 which can be configured to facilitate bonding of the strip 300 to the underlying balloon, which can be as disclosed, for example in PCT Pub. No. WO 2016/073490 published on May 12, 2016 and hereby incorporated by reference in its entirety. The apertures 503 can be relatively oval shaped, circular, or any other shape depending on the desired clinical result.

In some embodiments, the longitudinal axis of the strips are longitudinally oriented along the balloon and spaced apart from each other. In some embodiments, the strips do not completely cover the length of the balloon. For example, in one embodiment an 80mm long balloon can have strips that measure 76.6 mm. While the length of the strip can be the same as the defined working balloon length, in some embodiments the length of the strip is shorter than the defined working balloon length to allow for balloon contraction that is typically observed when a balloon goes to rated burst pressure. The length of each strip can in some cases be no more than about 15%, 10%, 9%, 8%, 7%, 6%, 5%, 4%, 3%, 2%, or 1%, or between about 2% and about 8%, between about 3% and about 6%, or between about 4% and about 5% shorter than the overall working balloon length. In some embodiments, the working balloon length does not include the lengths of the cones.

In some embodiments, part of the strip, e.g., the base of the strip (e.g., the inferiormost surface configured to be attached to the outer surface of the balloon) can be roughened to aid in adhesion.

Spikes (e.g., serrating elements or wedge dissectors) can be fabricated in many different manufacturing methods and in a large range of shapes. Regarding the manufacturing processes, the devices may be fabricated using one or more additive or subtractive processes. Additive processes such as high energy vapor deposition, for instance laser chemical vapor deposition, self-assembly techniques, polymer/metal 3D printing, selective laser sintering, powder printers, or other stereo lithographic are a few such options but other additive processes may be used. Alternatively, subtractive processes such as etching, CNC milling, laser cutting, water jet, or electrical discharge machining are just a few examples but other subtractive processes may be used.

In some embodiments, a method of fabrication includes the use of a reel of martensitic stainless steel, such as for example a 300 or 400 series stainless steel with a hardness of about 52 to about 64 on the Rockwell C-scale (HRC) although other materials can be used. The reel is then honed on one or both edges of the steel. In some embodiments, the steel is in the form of a thin reel strip about 0.007" to about 0.015" thick and between about 0.25" to about 0.75" wide, but can range between 0.005" and about 0.005", and 0.020" and between 0.15" and 1" wide. In some embodiments, the tolerance of the thickness and width of the reel is greater on the higher end and can have a thickness greater than about 0.020" and a width greater than about 1". The honed edge can be a single hone or two or more honed angles (as illustrated, for example in FIGS. 21 and 22). In some embodiments, when the angle of the honed edges are measured as the slope from the bounded end to the height of the unbounded end shown in FIG. 21, the angle of the honed edge can be, for example, greater than about 75 degrees. But when more than one honed angle is used, then the tip angle is can be less than, for example, about 75 degrees. In some embodiments, the honed edge has an angle of about or at least about 70, 75, 80, 85, 90 degrees or greater as it moves toward the honed edge in a series of bevels. In addition to the honed edge, independent of the number of honed angles, in some embodiments a separate and additional edge is generated at the very tip of the unbound edge of the strips. When added, the additional tip edge height from the honed edge to the unbounded edge is often very short and typically has a much larger angle than the overall honed edge. Independent of the number of honed angles used, the unbounded tip width, $W_u$, can be described as the radius of the tip. The unbounded tip width, Wu is the penetrating edge into the lesion, when the width is, in some cases, less than about 0.01" or 0.005", the surface area is minimized to have a less pronounced contact surface with the vessel enabling a reduced amount of energy requirement for penetration. When the tip is configured for penetration into harder surfaces such as calcium beds, in some cases either a more obtuse angle or the removal of the unbound tip at a greater distance from the unbounded surface can produce a wider tip edge (see FIG. 21, Wu). Not to be limited by theory, this wider edge distributes the load across the larger surface area generating a more effective resistance to tip deformation when the tip is pressured into rigid tissue surfaces. Once the reel is sharpened it is stamped to a desired length of blades. In some embodiments, the reel is hardened and then stamped to the desired length. Independent of when the stamping occurs, the blades can in some cases be passivated and hardened above, e.g., about HRC 45, but more typically in a range of from about HRC 58 to about HRC 62. The hardened blade can then be laser cut, stamped, EDM'ed or another precise metal shaping technology with spikes, serrating elements or wedge dissectors utilized. In some cases, the serrated elements are processed on the reel and then hardened and passivated. In some embodiments of strips where the tip is not a sharpened honed edge, the tip of the blade, that was produced during the reel sharpening step, is removed during the wedge dissector and strip manufacturing step. In some cases, the material removal is design to start a distance, such as from about 0.0001" to about 0.003" below the honed edge, or from about 0.0001" to about 0.0005" is removed from the honed edge, producing a flat top as illustrated in FIG. 21. The thinnest edge remaining (now a flat top in some cases) on the previously honed edge side is what will become the unbounded surface of the strip.

In some embodiments, disclosed are methods for attaching the strips. The methods can include any number of processing steps that provides effective strip retention, perpendicular orientation, and structural stability during the fabrication and use. In one embodiment the bounded surface is typically coated with a base coat of an appropriate material, such as a polymer, e.g., polyurethane through a controlled dipping process producing a uniform layer of polyurethane. The coating is dried and typically 3 or 4 strips are aligned with a strip alignment mechanism or jig and glued with a medical grade cyanoacrylate into place at predetermined orientations. The number of strips and the periodicity can vary from, for example, 1 to 8 and is typically associated with the same number of balloon folds but can be less than the number of folds and the periodicity can be non-sequential. Once the strips are bonded to the balloon surface, a single or series of multiple top coats or retention layers, are placed over the metal interrupted scoring elements or wedge dissectors to retain the strips and protect the balloon from the thin tips of the scoring elements. In some embodiments, these layers follow a similar process as the base or pre coat using a controlled dipping process producing one or more uniform layers of urethane or polyurethane. Once the retention layer or layers are cured a layer of hydrophilic or other coating may be apply to decrease balloon friction and increase the balloons deliverability and retrievability. When incorporated, the outer slip coating as can increase the functionality of the balloon by reducing the force to insert and retract the device.

Figure 27:
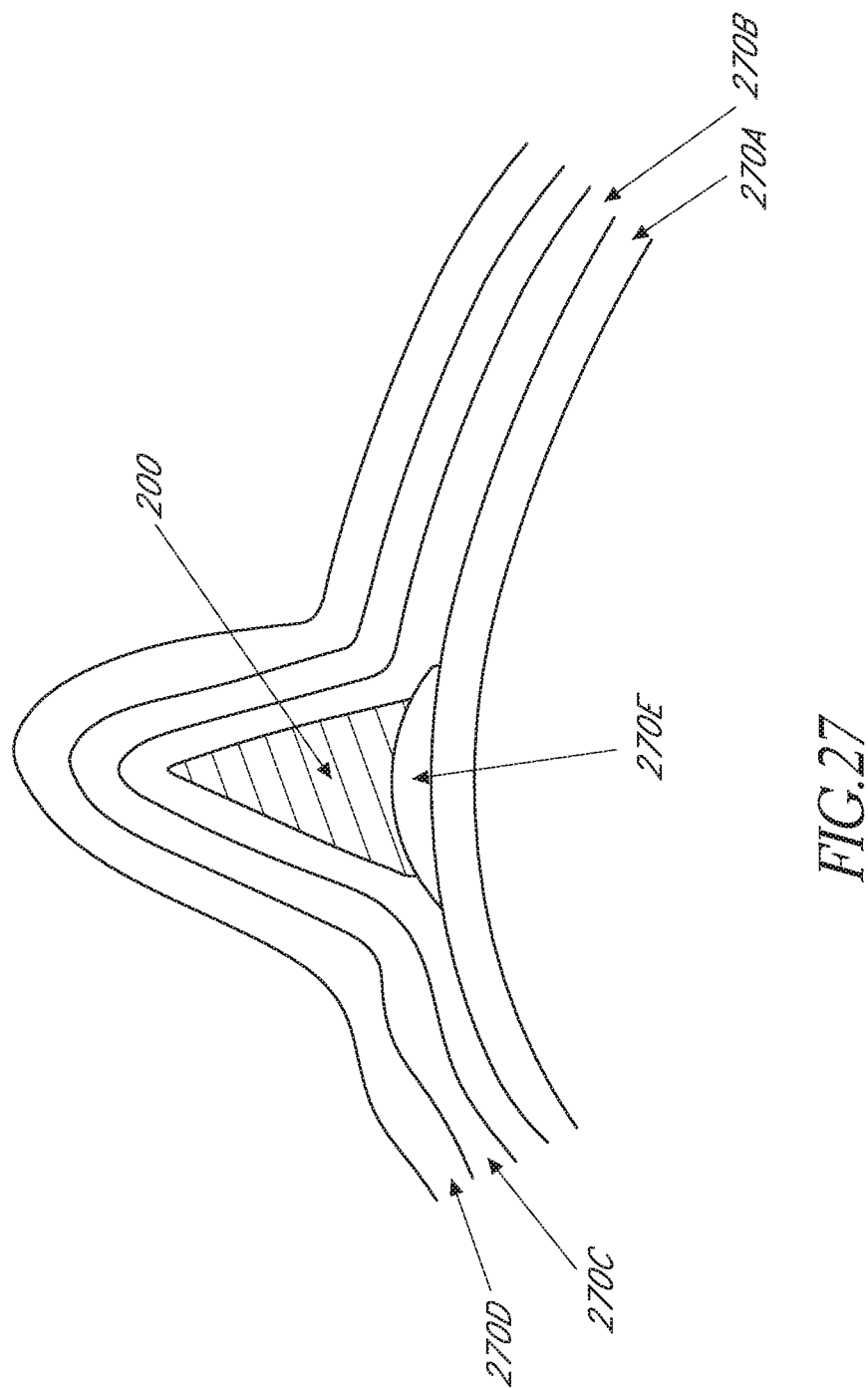
FIG. 27 illustrate a schematic cross-section of a balloon with wedge dissector and intervening layers.

FIG. 27 illustrates a schematic cross-sectional view of a strip and wedge dissector operably attached to the outer surface of a balloon, according to some embodiments of the invention. A polymer layer, typically thin (e.g., from 0.0001" to 0.0009"), or about or less than about 0.001" in some embodiments, such as to limit increasing the balloon diameter profile, can be used as a base coat (layer 270A) covering the outer balloon surface. This base coat 270A offers an interface bonding layer for the interrupted scoring element to the balloon surface. This layer 270A can be made of the same or similar polymer chemistry as other layers while offering a chemical, mechanical, or electromagnetic bond to the balloon surface. This base coat layer 270A can be configured to and potentially capable of reducing the interface strain between the balloon outer surface and the bonding surface of the metal scoring element. Strain between the two surfaces is reduced by allowing an adhesive layer 270E and the scoring element 200 to be sandwiched within a polymer matrix independent and somewhat isolated from the balloon strain during balloon expansion and pressure. Although typical base coats 270A are polymers, e.g., urethane or polyurethane this layer can be a variety of other materials. In some embodiments, the coating could include silicone and hydrophilic coatings involving hydrogel polymers or the like, such as polymer networks of a vinyl polymer and an uncrosslinked hydrogel, for example. Polyethylene oxide (PEO) is an example of a hydrogel. An example of a vinyl polymer is neopentyl glycol diacrylate (NPG). The deposition of the layer can be done by single or a series of dips of a balloon or matrix of balloons into a polymer bath under controlled insertion and extraction conditions at controlled rates in both or in one direction. Alternately, layers can be deposited at Angstrom layers through self-assembly of monolayers using known and practiced self-assembly techniques, typically employing surface ionic charging.

Still referring to FIG. 27, a bonding layer 270E between the metal scoring element and the basecoat can typically be thin (0.0001" to 0.0005") but can be as thick as 0.001" in some embodiments and thin enough such as to limit increasing the balloon diameter profile. The adhesive layer 270E can be a cyanoacrylate but can be made from other bonding materials that offer a chemical, mechanical, or electromagnetic bond between the basecoat 270A and the bonding surface of the metal scoring element. This layer 270E can be seen as the functional layer at joining the bonding surface of the metal scoring element to the balloon and sometimes is the only layer between the bonding surface of the metal scoring element and the outer balloon surface. This layer 270E can be one or more adhesive products. In one preferred embodiment the adhesive layer 270E is a single adhesive with the low viscosity allowing a wicking of the adhesive along the interface of the bonded surface of the metal scoring element and the base coat. In some embodiments, an adhesive dries quickly, allowing successive layers to be applied on the top of the adhesive layer with minimal curing delay. In other methods of fabrication, a more viscous adhesive layer can be placed at both ends of the bottom of the strips or periodically between the bonding surface of the metal scoring element and the base layer allowing non-glued sections to be free or unbonded. In still another method more than one adhesive can be used. For instance, a more viscous adhesive can be used on either end of the bonding surface of the metal interrupted scoring elements and then followed by wicking adhesive on some or all of the unbonded sections. In some embodiments, one (e.g., a single layer) two, or more retention layers (two layers shown in FIG. 27) 270B, 270C can be present over the base layer 270A as well as the scoring element. A polymer retention layer can in some embodiments be similar to, and have dimensions as described above for the base layer with enough properties such that the base 270A and retention 270B, 270C layers produce an effective bond between the layers. In some cases, the retention layer(s) can be designed to offer a similar thickness as the base layer while other times it may be useful to have the retention layers slightly thicker than the base layer. Thicker base and/or retention layers can in some circumstances offer greater puncture resistance and increased durability of the balloon against potential puncturing from the metal interrupted scoring elements, any sharp edges from implants left in the body, or from sharp edges found in severely calcified disease vessels for example. In some embodiments, an outer slip layer 270D can also be present, above the retention layer(s) over the balloon and/or scoring elements. A variety of hydrophilic coatings are commercially available to reduce friction and offer increased navigation of balloons through tortuous and narrow anatomical features. In some embodiments, the balloon surface can be fully encased in a hydrophilic coating while in other embodiments the balloon can be coated after pleating or after pleating and crimping and therefore only surfaces that will typically be exposed during delivery are coated with the hydrophilic coat. Typical hydrophilic coats are a few microns thick and can be as thin as about 10 Angstroms in some embodiments.

In some embodiments, the adhesive can be applied separately to the balloon and to the strips and then both components are then bonded together. A template can be used to ensure proper positioning of the scoring elements along the surface of the balloon.

A retention polymer layer 270B, 270C can be typically similar to the base layer with enough properties such that the base and retention layers produce an effective bond between the layers. Sometimes the retention layer(s) can be designed to offer a similar thickness as the base layer while other times it may be useful to have the retention layers slightly thicker than the base layer, such as about or no more than about 20%, 15%, 10%, or 5% thicker in some cases. Thicker base and/or retention layers offer greater puncture resistance and increased durability of the balloon against potential puncturing from the metal interrupted scoring elements, any sharp edges from implants left in the body, or from sharp edges found in severely calcified disease vessels. In some embodiments with a plurality of retention layers 270B, 270C, the layers can be made of the same or differing materials.

A variety of hydrophilic coatings are commercially available to reduce friction and offer increased navigation of balloons through tortuous and narrow anatomical features. In some embodiments, layer 270D of FIG. 27 can be a hydrophilic slip layer. In one preferred embodiment the balloon surface can be fully incased in a hydrophilic coating while in other embodiments the balloon can be coated after pleating or after pleating and crimping and therefore only surfaces that will typically be exposed during delivery are coated with the hydrophilic coat. Typical hydrophilic coats are a few microns thick and can be as thin as, for example 10 Angstroms.

Figure 28:
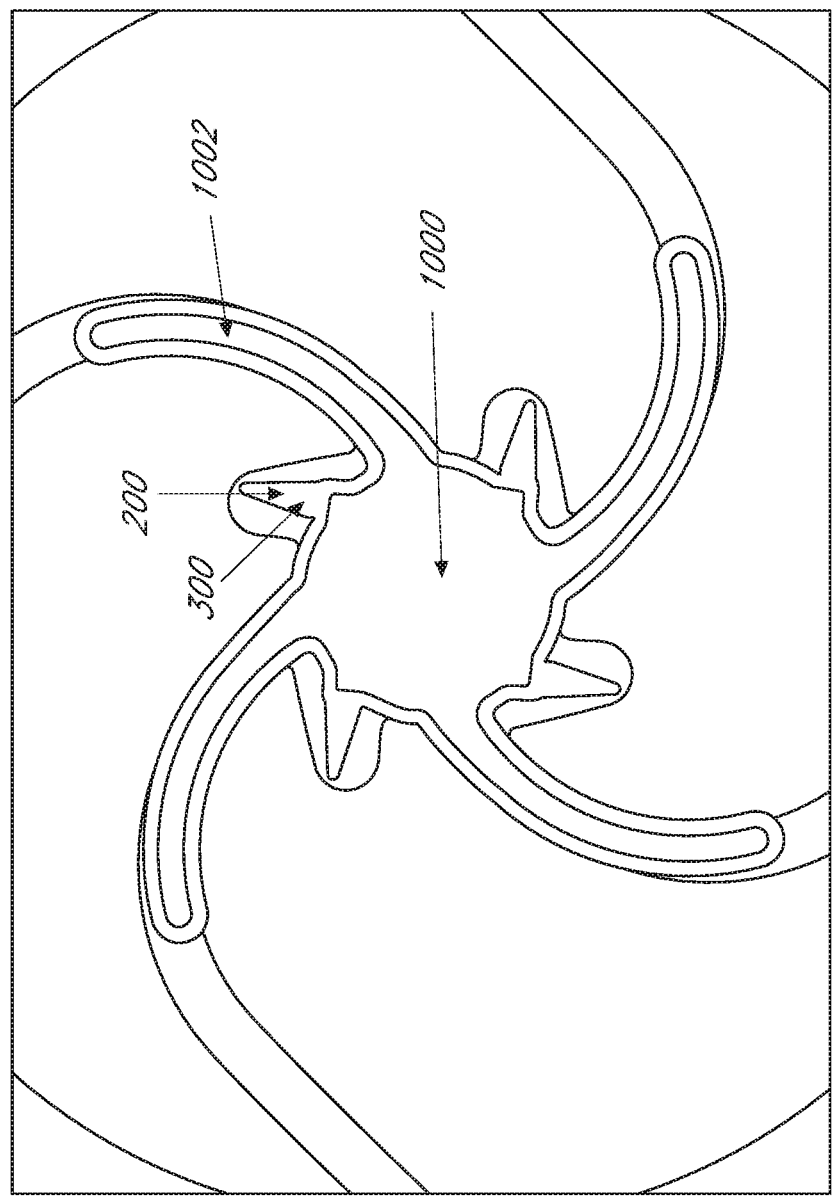
FIG. 28 illustrate an embodiment of a pleated balloon with strips and wedge dissectors in between pleats.

The height of the wedge dissectors, strips, and layers of the outer balloon encapsulation process can be viewed as a cage for use with an expandable member such as a medical balloon, such as an angioplasty balloon or as part of a medical procedure involving a medical balloon or other expandable member. In order to effectively perform key hole or catheter based surgery, the ability to fold the balloon to a fraction of the diameter of the intended inflation diameter can be of value. Therefore the balloon and in some cases the cage are typically folded where the profile of the folded balloon can be effectively used. In one such embodiment the cage is folded in a manner that offers orientation of the spikes such as to avoid puncturing the balloon or scraping the intima of the lumen during delivery and removal, as illustrated in FIG. 28. FIG. 28 illustrates the balloon 1000 with a plurality of pleats 1002, and strips 300 and associated wedge dissectors 200 in between the pleats, thus allowing a single strip 300 with its plurality of wedge dissectors 200 to lie between two pleats 1002. A pleating tool was designed that offers effective orientation of the spikes and splines. The pleating tool can have a series of pleating wedges where each wedge offers the ability of the crimp the balloon between the wedges as the wedge elements are closed down onto the balloon. Due to the bulk of the spline elements and desire to minimize contact, and potential damage to the wedge heads, the wedges are designed with a series of pockets that run the length of the wedge heads. The pockets in the wedge heads offer the ability of the spline features to rest within said pockets and limits the spline to wedge contact. The pockets can also offer the ability to aid in orientation of the spline and spike features such that the orientation of the features limits contact with the balloon, such as over folding, and limits orientation, such as perpendicular orientation to the balloon, that might produce scraping of the intima of the vessel during transport of the device on said balloon. One such orientation of the spikes might be at a tangential orientation, an apparent lying down, to the balloon surface as illustrated in FIG. 28.

Various other modifications, adaptations, and alternative designs are of course possible in light of the above teachings. Therefore, it should be understood at this time that within the scope of the appended claims the invention may be practiced otherwise than as specifically described herein. It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "creating microperforations in an arterial plaque" includes "instructing the creating of microperforations in an arterial plaque." The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A medical balloon catheter, comprising:
an elongate member comprising a lumen, the elongate member defining a longitudinal axis;
an expandable balloon connected to the elongate member proximate a distal end of the elongate member;
a plurality of strips, each strip of the plurality of strips including a plurality of wedge dissectors spaced apart along a surface of each strip, each strip extending longitudinally along an outer surface of the expandable balloon,
a ramp of material covering lateral ends of each of the strips, the material being relatively more flexible than that of each of the strips;
a base layer on the outer surface of the expandable balloon; and
a bonding layer on top of the base layer and on an underside of each of the plurality of strips;
wherein the wedge dissectors comprise a strip-facing base surface directly adjacent the surface of each of the strips, a radially outward facing surface having a length between a proximal edge of the radially outward facing surface and a distal edge of the radially outward facing surface and defining a height of each wedge dissector, and lateral surfaces between the strip-facing base surface and the radially outward facing surface, wherein the radially outward facing surface has a first width at the proximal edge, a second width smaller than the first width between the proximal edge and the distal edge, and a third width at the distal edge larger than the second width,
wherein the expandable balloon comprises a plurality of pleats extending from the outer surface and spaced apart from the plurality of strips, wherein the expandable balloon comprises a first reduced configuration in which the wedge dissectors of each strip lie between two adjacent pleats such that a longitudinal axis of each wedge dissector of each strip is in a tangential non-perpendicular orientation with respect to the outer surface of the expandable balloon directly below each wedge dissector of each strip, and wherein the expandable balloon comprises a second expanded configuration wherein the longitudinal axis of each wedge dissector of each strip is in a perpendicular orientation with respect to the outer surface of the expandable balloon directly below each wedge dissector of each strip,
wherein the ramp of material slopes from the outer surface of the balloon to the lateral ends of each of the strips.

2. The medical balloon catheter of claim 1, wherein the ramp of material comprises an adhesive.

3. The medical balloon catheter of claim 1, wherein each strip of the plurality of strips comprises a textured surface.

4. The medical balloon catheter of claim 1, further comprising a plurality of tabs on an inferior-facing surface of each of the plurality of strips opposite the wedge dissectors.

5. The medical balloon catheter of claim 1, further comprising a plurality of reliefs on each of the plurality of strips.

6. The medical balloon catheter of claim 1, wherein the base layer comprises a polymer.

7. The medical balloon catheter of claim 1, wherein the bonding layer comprises a cyanoacrylate.

8. The medical balloon catheter of claim 1, further comprising a first retention bonding layer and a second retention bonding layer on top of the bonding layer, wherein the first retention bonding layer and a second retention bonding layer comprise the same material.

9. A medical balloon catheter, comprising:
an elongate member comprising a lumen, the elongate member defining a longitudinal axis;
an expandable balloon connected to the elongate member proximate a distal end of the elongate member;
a plurality of strips, each strip of the plurality of strips including a plurality of wedge dissectors spaced apart along a surface of each strip, each strip extending longitudinally along an outer surface of the expandable balloon,
a ramp of material covering lateral ends of each of the strips, the material being relatively more flexible than that of each of the strips;
a base layer on the outer surface of the expandable balloon; and
a bonding layer on top of the base layer and on an underside of each of the plurality of strips; and
a first retention bonding layer and a second retention bonding layer on top of the bonding layer, wherein the first retention bonding layer and a second retention bonding layer comprise the same material,
wherein the wedge dissectors comprise a strip-facing base surface directly adjacent the surface of each of the strips, a radially outward facing surface having a length between a proximal edge of the radially outward facing surface and a distal edge of the radially outward facing surface and defining a height of each wedge dissector, and lateral surfaces between the strip-facing base surface and the radially outward facing surface,
wherein the expandable balloon comprises a plurality of pleats extending from the outer surface and spaced apart from the plurality of strips, wherein the expandable balloon comprises a first reduced configuration in which the wedge dissectors of each strip lie between two adjacent pleats such that a longitudinal axis of each wedge dissector of each strip is in a tangential non-perpendicular orientation with respect to the outer surface of the expandable balloon directly below each wedge dissector of each strip, and wherein the expandable balloon comprises a second expanded configuration wherein the longitudinal axis of each wedge dissector of each strip is in a perpendicular orientation with respect to the outer surface of the expandable balloon directly below each wedge dissector of each strip.

10. The medical balloon catheter of claim 9, wherein the ramp of material slopes from the outer surface of the balloon to the lateral ends of each of the strips.

11. The medical balloon catheter of claim 9, wherein the ramp of material comprises an adhesive.

12. The medical balloon catheter of claim 9, wherein each strip of the plurality of strips comprises a textured surface.

13. The medical balloon catheter of claim 9, further comprising a plurality of tabs on an inferior-facing surface of each of the plurality of strips opposite the wedge dissectors.

14. The medical balloon catheter of claim 9, further comprising a plurality of reliefs on each of the plurality of strips.

15. The medical balloon catheter of claim 9, wherein the base layer comprises a polymer.

16. The medical balloon catheter of claim 9, wherein the bonding layer comprises a cyanoacrylate.

* * * * *